(12) United States Patent
Jarrell et al.

(10) Patent No.: US 12,123,004 B2
(45) Date of Patent: Oct. 22, 2024

(54) GENERATION OF ACYL AMINO ACIDS

(71) Applicant: Modular Genetics, Inc., Woburn, MA (US)

(72) Inventors: Kevin A. Jarrell, Lincoln, MA (US); Michelle Pynn, Andover, MA (US)

(73) Assignee: Modular Genetics, Inc., Lincoln, MA (US)

( * ) Notice: Subject to any disclaimer, the term of this patent is extended or adjusted under 35 U.S.C. 154(b) by 875 days.

(21) Appl. No.: 17/260,984

(22) PCT Filed: Jul. 18, 2019

(86) PCT No.: PCT/US2019/042494
§ 371 (c)(1),
(2) Date: Jan. 15, 2021

(87) PCT Pub. No.: WO2020/018853
PCT Pub. Date: Jan. 23, 2020

(65) Prior Publication Data
US 2021/0292770 A1 Sep. 23, 2021

Related U.S. Application Data

(60) Provisional application No. 62/700,118, filed on Jul. 18, 2018.

(51) Int. Cl.
| | | |
|---|---|---|
| *C12N 15/52* | (2006.01) | |
| *C12N 1/20* | (2006.01) | |
| *C12N 9/02* | (2006.01) | |
| *C12N 9/10* | (2006.01) | |
| *C12N 9/90* | (2006.01) | |
| *C12P 13/14* | (2006.01) | |
| *C12R 1/125* | (2006.01) | |

(52) U.S. Cl.
CPC ............... *C12N 15/52* (2013.01); *C12N 1/20* (2013.01); *C12N 9/0071* (2013.01); *C12N 9/1007* (2013.01); *C12N 9/90* (2013.01); *C12P 13/14* (2013.01); *C12R 2001/125* (2021.05); *C12Y 502/01004* (2013.01)

(58) Field of Classification Search
CPC ........ C12N 15/52; C12N 1/20; C12N 9/0071; C12N 9/1007; C12N 9/90; C12P 13/14; C12P 7/6409; C12P 13/04; C12R 2001/125; C12Y 502/01004; C12Y 502/01008
See application file for complete search history.

(56) References Cited

U.S. PATENT DOCUMENTS

| | | | |
|---|---|---|---|
| 5,652,116 A | 7/1997 | Grandi et al. | |
| 5,795,738 A | 8/1998 | Grandi et al. | |
| 7,981,685 B2 * | 7/2011 | Jarrell | C12P 13/04 436/112 |
| 8,338,483 B2 | 12/2012 | Klug et al. | |
| 11,045,404 B2 * | 6/2021 | Su | A61K 8/4946 |
| 2009/0031454 A1 | 1/2009 | Meesapyodsuk et al. | |
| 2013/0089899 A1 | 4/2013 | Kurek et al. | |

FOREIGN PATENT DOCUMENTS

| | | |
|---|---|---|
| WO | WO-2008/131002 A2 | 10/2008 |
| WO | WO-2014/144649 A1 | 9/2014 |
| WO | WO-2015/176922 A1 | 11/2015 |
| WO | WO-2017/011592 A1 | 1/2017 |
| WO | WO-2020/018853 A2 | 1/2020 |
| WO | WO-2020/018853 A3 | 3/2020 |

OTHER PUBLICATIONS

Hannemann, Frank, et al. "Cytochrome P450 systems—biological variations of electron transport chains." Biochimica et Biophysica Acta (BBA)—General Subjects 1770.3 (2007): 330-344. (Year: 2007).*
Zhang, Meiling, David A. Case, and Jeffrey W. Peng. "Propagated perturbations from a peripheral mutation show interactions supporting WW domain thermostability." Structure 26.11 (2018): 1474-1485. (Year: 2018).*
K Singh, Raushan, et al. "Protein engineering approaches in the post-genomic era." Current Protein and Peptide Science 19.1 (2018): 5-15. (Year: 2018).*
Axarli, I. et al. Cytochrome P450 I 02A2 Catalyzes Efficient Oxidation of Sodium Dodecyl Sulphate: A Molecular Tool for Remediation., Enzyme Res., 2010: 125429 (2010).
Caboche, S. et al., NORINE: a database of nonribosomal peptides, Nucleic Acids Research, 36: D326-D33I (2008).
Coque, J. J. et al., The cephamycin biosynthetic genes pcbAB, encoding a large multidomain peptide synthetase, and pcbC of Nocardia lactamdurans are clustered together in an organization different from the same genes in Acremonium chrysogenum and Penicillium chrysogenum, Mal. Microbiol., 5(5):1125 (1991).
Cosmina, P. et al., Sequence and analysis of the genetic locus responsible for surfactin synthesis in Bacillus subtilis, Mol. Microbiol., 8(5):821-831 (1993).
Cryle, M. J. et al., Products of cytochrome P450(Biol) (CYP107HI)-catalyzed oxidation of fatty acids, Org Lett., 5(18):3341-4 (2003).
Cryle, M. J. et al., Structural and biochemical characterization of the cytochrome P450 CypX (CYP134AI) from Bacillus subtilis: a cyclo-Lleucyl-L-leucyl dipeptide oxidase., Biochemistry, 49(34):7282-96 (2010).

(Continued)

*Primary Examiner* — Paul J Holland
*Assistant Examiner* — Erica Nicole Jones-Foster
(74) *Attorney, Agent, or Firm* — Choate, Hall & Stewart LLP; Brenda Herschbach Jarrell; Rolando Medina

(57) ABSTRACT

Engineered polypeptides or engineered microbial cells useful in synthesizing acyl amino acids are provided. In some embodiments, engineered polypeptides or engineered microbial cells are useful in synthesizing acyl amino acids with one or more hydroxyl and/or methyl groups at one or more positions of the fatty acid portion of the acyl amino acid (e.g., at ω-1, ω-2, and/or ω-3 positions of the fatty acid portion of the acyl amino acid). Also provided are methods of making acyl amino acids using engineered polypeptides and/or engineered microbial cells.

14 Claims, 3 Drawing Sheets
Specification includes a Sequence Listing.

(56) References Cited

OTHER PUBLICATIONS

Diez, B. et al., The cluster of penicillin biosynthetic genes. Identification and characterization of the pcbAB gene encoding the alpha-aminoadipyl-cysteinyl-valine synthetase and linkage to the pcbC and penDE genes, J Biol. Chem., 265:16358 (1990).

Gustafsson, M. C. U. et al., Expression, purification, and characterization of Bacillus subtilis cytochromes P450 CYP102A2 and CYP102A3: flavocytochrome homologues of P450 BM3 from Bacillus megaterium, Biochemistry, 43: 5474-87 (2004).

International Preliminary Report on Patentability for PCT/US2019/042494, 9 pages (Jan. 19, 2021).

International Search Report for PCT/2019/042494, 5 pages (mailed Jan. 21, 2020).

Julotok, M. et al., Influence of fatty acid precursors, including food preservatives, on the growth and fatty acid composition of Listeria monocytogenes at 37 and 10degreesC, Appl. Environ Microbiol., 76(5):1423-32 (2010).

Kleinkauf, H and Dohren, H. V., Biosynthesis of peptide antibiotics, Annu. Rev. Microbiol., 41 :259-289 (1987).

Kratzxchmar, J. et al., Gramicidin S biosynthesis operon containing the structural genes grsA and grsB has an open reading frame encoding a protein homologous to fatty acid thioesterases, J. Bacteriol., 171:5422-5429 (1989).

Maccabe, A. P. et al., Delta-(L-alpha-aminoadipyl)-L-cysteinyl-D-valine synthetase from Aspergillus nidulans. Molecular characterization of the acvA gene encoding the first enzyme of the penicillin biosynthetic pathway, J Biol. Chem., 266(19):12646 (1991).

Meyers, E. W. and Miller, W., Optimal alignments in linear space, CABIOS, 4:11-17 (1988).

Nagai, S. et al., Study on surfactin, a cyclic depsipeptide. 2. Synthesis of surfactin B2 produced by Bacillus natto KMD 2311., Chem Pharm Bull, 44:5-10 (1996).

Reddick, J. J. et al., PksS from Bacillus subtilis is a cytochrome P450 involved in bacillaene metabolism, Biochem Biophys Res Commun., 358(1):363-7 (2007).

Reznik, G. O. et al., Use of sustainable chemistry to produce an acyl amino acid surfactant, Appl Microbiol Biotechnol., 86(5): 1387-97 (2010).

Richardt, A. et al., Ebony, a novel nonribosomal peptide synthetase for beta-alanine conjugation with biogenic amines in *Drosophila*, J. Biol. Chem., 278( 42):41160-6 (2003).

Smith, D. J. et al., Beta-lactam antibiotic biosynthetic genes have been conserved in clusters in prokaryotes and eukaryotes, EMBO J, 9:741 (1990).

Smith, D. J. et al., The multifunctional peptide synthetase performing the first step of penicillin biosynthesis in Penicillium chrysogenum is a 421,073 dalton protein similar to Bacillus brevis peptide antibiotic synthetases, EMBO J, 9:2743 (1990).

Sun, J. et al., Formation of hydroxylated and methoxylated polychlorinated biphenyls by Bacillus subtilis: New insights into microbial metabolism, Sci Total Environ., 613-614: 54-61 (2018).

Weckermann, R. et al., Complete nucleotide sequence of the tycA gene coding the tyrocidine synthetase 1 from Bacillus brevis, Nucl. Acid. Res., 16(24):11841-11843 (1988).

Written Opinion for PCT/2019/042494, 11 pages (mailed Jan. 21, 2020).

Zhang, A. et al. The crystal structure of the versatile cytochrome P450 enzyme Cyp 109B 1 from Bacillus subtilis, Mal Biosyst., 11(3):869-81 (2015).

* cited by examiner

GENERATION OF ACYL AMINO ACIDS

CROSS-REFERENCE TO RELATED APPLICATIONS

This application claims the benefit of U.S. Provisional Application No. 62/700,118 filed Jul. 18, 2018, the contents of which are hereby incorporated herein in its entirety.

BACKGROUND

Acyl amino acids are commercially important compounds. Many have advantageous characteristics and are sold as surfactants, antibiotics, anti-insect agents and as a variety of other important agents. Traditionally, acyl amino acids have been manufactured chemically. Such chemical manufacturing methods are hampered by a variety of shortcomings including the ease of obtaining and storing the starting materials, the necessity of using harsh and sometimes dangerous chemical reagents in the manufacturing process, the difficulty and efficiency of the synthesis itself, and/or the fiscal and environmental cost of disposing chemical by-products, etc.

SUMMARY

The present inventors have previously described engineered polypeptides or engineered cells (see, for example, WO2008/131002 and WO2014/144649) that can be useful, among other things, for generation for acyl amino acids. Attributes of these engineered polypeptides or engineered cells addressed one or more shortcomings associated with chemical manufacturing of acyl amino acids as discussed above.

The present disclosure provides certain further insights and developments including, among other things, that acyl amino acids produced in microbial cells such as *Bacillus* cells, can be modified, for example, by hydroxylation and/or methylation, and that generation of such modified acyl amino acids can be controlled by use of strain engineering. In particular, for example, the present disclosure demonstrates that inactivation of a fatty acid hydroxylase (e.g., by inactivating cypB gene) in acyl amino acid-producing cells can reduce or eliminate hydroxylation of a fatty acid portion of an acyl amino acid at one or more ω-n positions, where n≥1 (e.g., ω-1, ω-2, and/or ω-3 positions). Such engineered constructs can be useful, for example, in certain circumstances where fatty acid hydroxylation results in production of such hydroxylated products as by-products, the presence of which in turn lowers the yield of desired surfactants and/or fatty acids that do not comprise additional hydroxyl groups (except that in some embodiments, such desirable surfactants and/or fatty acid may have a β-hydroxyl group). The present disclosure also provides, among other things, insights that in certain circumstances where hydroxylation of a fatty acid portion of an acyl amino acid at one or more ω-n positions, where n≥1 (e.g., ω-1, ω-2, and/or ω-3 positions) is desirable, such products can be produced by engineering cells to activate or over-express a gene encoding a fatty acid hydroxylase. Thus, the present disclosure teaches engineering acyl amino acid-producing cells to comprise a modification that modulates hydroxylation and/or alkylation (e.g., methylation) of a fatty acid portion of an acyl amino acid. Such technologies can be useful in increasing yield of surfactants and/or fatty acids of interest (e.g., with or without ω-n hydroxyl groups, where n≥1).

In some aspects, provided herein are engineered cells (e.g., engineered microbial cells) that are capable of producing acyl amino acids and modulating hydroxylation and/or methylation of a fatty acid portion of such acyl amino acids. In some embodiments, such an engineered cell (e.g., microbial cell) is an acyl amino acid-producing cell, which comprises a modification (e.g., a genetic modification) that modulates hydroxylation and/or methylation of a fatty acid portion of an acyl amino acid. In some embodiments, such an engineered microbial cell expresses at least one peptide synthetase, which produces or synthesizes an acyl amino acid.

In some embodiments involving a modification that modulates hydroxylation and/or methylation of a fatty acid portion of an acyl amino acid, such a modification may result in an increase in the number of hydroxyl and/or alkyl (e.g., methyl) groups of a fatty acid portion of an acyl amino acid, as compared to that when the modification is absent. In alternative embodiments, such a modification may result in a reduction in the number of hydroxyl and/or alkyl (e.g., methyl) groups of a fatty acid portion of an acyl amino acid, as compared to that when the modification is absent.

In some embodiments, such a modification that modulates hydroxylation and/or methylation of a fatty acid portion of an acyl amino acid is or comprises a modification in a gene that encodes a fatty acid modifying enzyme. In some embodiments, such a modification that modulates hydroxylation and/or methylation of a fatty acid portion of an acyl amino acid is or comprises a modification in one or more regulatory elements operably linked to a gene that encodes a fatty acid modifying enzyme. Depending on desirable types of acyl amino acids to be generated (e.g., with or without ω-n hydroxyl groups, where n≥1), in some embodiments, such a modification may be engineered to increase expression and/or activity of a gene that encodes a fatty acid modifying enzyme, while, in some embodiments, such a modification may be engineered to decrease expression of a gene that encodes a fatty acid modifying enzyme.

In some embodiments, a fatty acid modifying enzyme can be or comprise a fatty acid hydroxylase and/or a fatty acid methylase. In some embodiments, a fatty acid modifying enzyme is or comprises a fatty acid hydroxylase. In some such embodiments, a fatty acid hydroxylase may hydroxylate a linear or unbranched fatty acid moiety, while in some such embodiments, a fatty acid hydroxylase may hydroxylate a branched fatty acid moiety. In some embodiments, a fatty acid hydroxylase may be selected to hydroxylate a specific fatty acid moiety, including, e.g., but not limited to caproic acid, caprylic acid, lauric acid, and myristic acid. Examples of a fatty acid hydroxylase that may be involved in generation of acyl amino acids can be encoded by a gene selected from the group consisting of bioI, cyp107h, cyp107J1, cyp134A1, cyp109B1, cyp152A1, cyp102A2, cyp102A3, cyp107K1, and combinations thereof.

Various fatty acid modifying enzymes (e.g., fatty acid hydroxylases and/or fatty acid methylases) may be involved in generation of different kinds of acyl amino acids, for example, depending on the types of the fatty acid and/or amino acid moieties of acyl amino acids to be generated. One of ordinary skill in the art reading the present disclosure will appreciate that a proper fatty acid modifying enzyme may be selected for modification to modulate hydroxylation and/or methylation of a particular fatty acid portion of an acyl amino acid accordingly.

In some embodiments involving a peptide synthetase as described and/or utilized herein, such a peptide synthetase may be endogenous to a host cell. In some embodiments, a peptide synthetase may be heterologous to a host cell. In some embodiments, a peptide synthetase may be an engineered peptide synthetase. In some embodiments, a cell (e.g., a microbial cell) can be engineered to express a peptide synthetase. For example, in some embodiments, a cell (e.g., a microbial cell) can be engineered to contain a polynucleotide encoding a peptide synthetase.

In some embodiments involving cells (e.g., engineered cells) as described and/or utilized herein, such cells may be *Bacillus* cells, e.g., *Bacillus subtilis* cells.

Engineered cells described and/or utilized herein are useful for making an acyl amino acid composition. Accordingly, some aspects of the present disclosure provide methods of making an acyl amino acid composition using such engineered cells. In some embodiments, such a method comprises a step of (a) culturing an engineered cell (e.g., ones as described and/or utilized herein) under conditions and for a time sufficient for an acyl amino acid composition to be made.

In some embodiments involving culturing, such culturing can comprise incubating an engineered cell (e.g., ones as described and/or utilized herein) in a culture medium that comprises one or more of a carbon source, a fatty acid, and an amino acid. In some embodiments, such a culture medium may comprise a carbon source, a fatty acid, and an amino acid. In some embodiments involving making an acyl glycinate composition, an amino acid present in a culture medium is or comprises glycine. In some embodiments involving making an acyl glutamate composition, an amino acid present in a culture medium is or comprises glutamic acid. In some embodiments involving making an acyl sarcosinate composition, an amino acid present in a culture medium is or comprises sarcosine. One of ordinary skill in the art reading the present disclosure will appreciate that other amino acids can be present in a culture medium for use in making other acyl amino acids.

In some embodiments involving engineered cells comprising a modification (e.g., a genetic modification) that reduces hydroxylation of a fatty acid portion of an acyl amino acid, less than 10%, less than 7.5%, less than 5%, less than 2.5%, less than 1%, less than 0.5%, less than 0.2%, or less than 0.1% of the acyl amino acid in an acyl amino acid composition is hydroxylated at one or more ω-n positons (e.g., ω-1, ω-2, and/or ω-3 positions) of the fatty acid portion of the acyl amino acid, as compared to an acyl amino composition made using cells without such a modification. In some such embodiments, an acyl amino acid composition is substantially free of acyl amino acids that are hydroxylated at one or more ω-n positions (e.g., ω-1, ω-2, and/or ω-3 positon) of the fatty acid portion of the acyl amino acid.

In some embodiments involving engineered cells comprising a modification that reduces methylation of a fatty acid portion of an acyl amino acid, less than 10%, less than 7.5%, less than 5%, less than 2.5%, less than 1%, less than 0.5%, less than 0.2%, or less than 0.1% of the acyl amino acid in an acyl amino acid composition is methylated at one or more ω-n positons (e.g., ω-1, ω-2, and/or ω-3 positions) of the fatty acid portion of the acyl amino acid, as compared to an acyl amino composition made using cells without such a modification. In some such embodiments, an acyl amino acid composition is substantially free of acyl amino acids that are methylated at one or more ω-n positions (e.g., ω-1, ω-2, and/or ω-3 positon) of the fatty acid portion of the acyl amino acid.

In some embodiments involving engineered cells comprising a modification that increases hydroxylation of a fatty acid portion of an acyl amino acid, greater than 70% or more, including, e.g., greater than 90%, greater than 95%, greater than 98%, or greater than 99% of the acyl amino acid in an acyl amino acid composition is hydroxylated at one or more ω-n positions (e.g., ω-1, ω-2, and/or ω-3 positon) of the fatty acid portion of the acyl amino acid, as compared to an acyl amino composition made using cells without such a modification. In some such embodiments, an acyl amino acid composition is substantially entirely of acyl amino acids that are hydroxylated at one or more ω-n positions (e.g., ω-1, ω-2, and/or ω-3 positon) of the fatty acid portion of the acyl amino acid.

In some embodiments involving engineered cells comprising a modification that increases methylation of a fatty acid portion of an acyl amino acid, greater than 70% or more, including, e.g., greater than 90%, greater than 95%, greater than 98%, greater than 99%, or more, of the acyl amino acid in an acyl amino acid composition is methylated at one or more ω-n positions (e.g., ω-1, ω-2, and/or ω-3 positon) of the fatty acid portion of the acyl amino acid, as compared to an acyl amino composition made using cells without such a modification. In some such embodiments, an acyl amino acid composition is substantially entirely of acyl amino acids that are methylated at one or more ω-n positions (e.g., ω-1, ω-2, and/or ω-3 positon) of the fatty acid portion of the acyl amino acid.

Technologies described and/or utilized herein are useful for generation of various acyl amino acids. In some embodiments, technologies provided herein can be useful for generation of acyl glycinate. In some embodiments, technologies provided herein can be useful for generation of acyl glutamate. In some embodiments, technologies provided herein can be useful for generation of acyl sarconsinate.

BRIEF DESCRIPTION OF THE DRAWING

In FIG. 2, the left-most rectangle represents a block of DNA that encodes an enzyme module, which catalyzes addition of a particular fatty acid (e.g., myristic acid (14 carbon)) onto a specific amino acid. When the "amino acid specifying" block of code is one particular sequence (e.g., glutamic acid), the fatty acids are linked to the amino acid glutamate. Acyl glutamate surfactant produced by such an engineered enzyme is referred to as FA-Glu (Fatty Acid linked to Glutamate, or AminoSurf-E). When the amino acid specifying block of code is a different sequence (e.g., glycine), the fatty acids are linked to the amino acid glycine. Acyl glycinate surfactant produced by such an engineered enzyme is referred to as FA-Gly (Fatty Acid linked to Glycine, or AminoSurf-G).

CERTAIN DEFINITIONS

Figure 1:
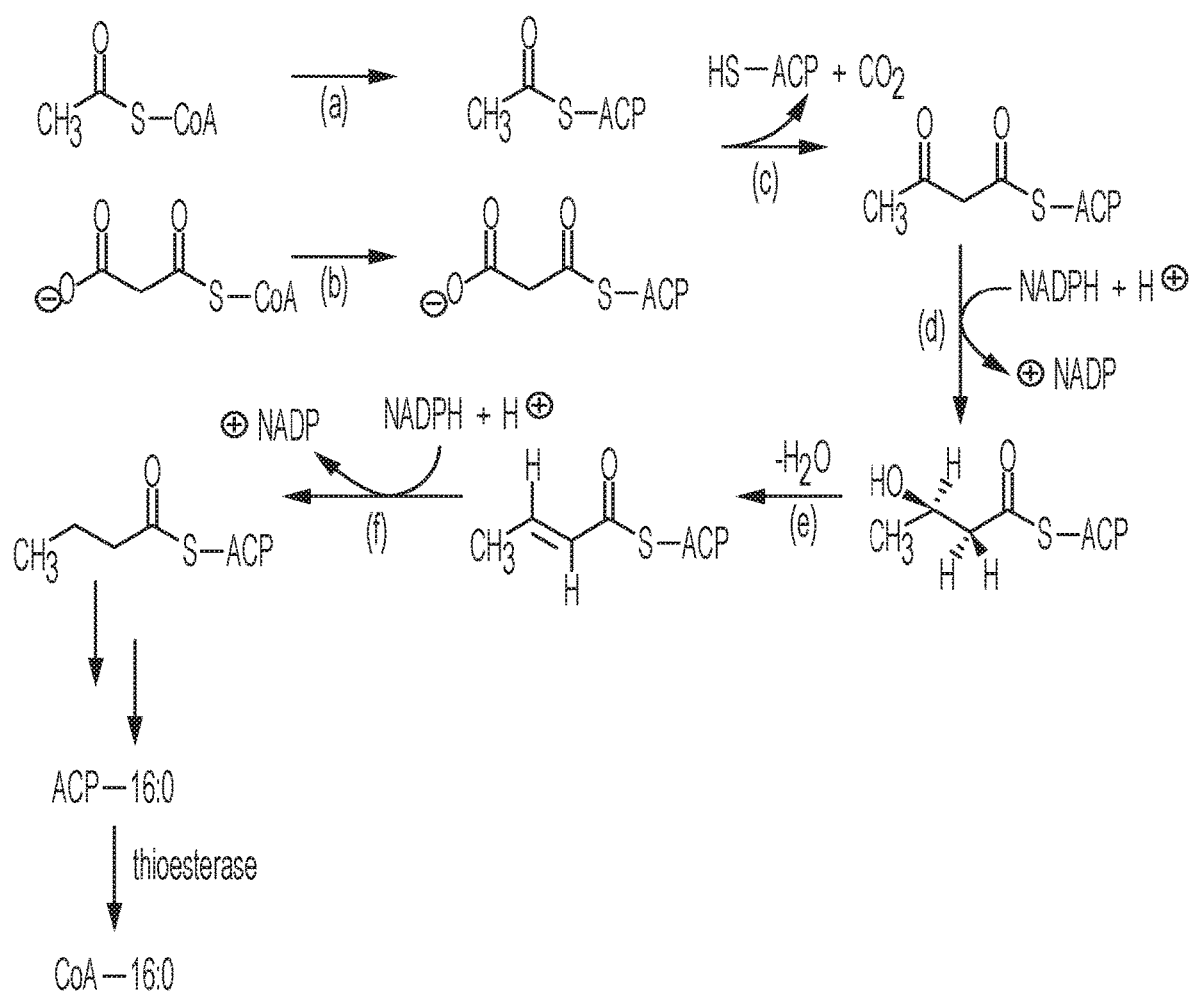
FIG. 1 presents a depiction of initial steps of fatty acid synthesis with an acetyl initiation moiety; the depicted steps achieve full saturation of the chain.

Acyl amino acid: The term "acyl amino acid" as used herein refers to an amino acid moiety that is covalently linked to a fatty acid moiety. In some embodiments, the amino acid and fatty acid moieties are covalently linked via an amide bond formed between a carboxylic acid group of a fatty acid and an amino group of an amino acid. In some embodiments, a fatty acid moiety or entity utilized or included in an acyl amino acid includes a β-hydroxyl group; in some embodiments, a fatty acid moiety or entity utilized or included in an acyl amino acid does not include a β-hydroxyl group. In some embodiments, a fatty acid moiety utilized or included in an acyl amino acid includes a β-amino group; in some embodiments, a fatty acid moiety or entity utilized or included in an acyl amino acid does not include a β-amino group. In some embodiments, a fatty acid moiety utilized or included in an acyl amino acid is unmodified at the β-position. In some embodiments, a fatty acid moiety utilized or included in an acyl amino acid is modified (e.g., by hydroxylation) at the β-position.

Acyl amino acid-producing cell: The term "acyl amino acid-producing cell" refers to a biological cell that produces or synthesizes an acyl amino acid (e.g., as described herein). In some embodiments, an acyl amino acid-producing cell expresses an enzyme that is capable of covalently associates a fatty acid with an amino acid. In some embodiments, such an enzyme may be an endogenous enzyme. In some embodiments, such an enzyme may be a heterologous enzyme. In some embodiments, such an enzyme may be an engineered enzyme. In some embodiments, such an enzyme may be or comprise a peptide synthetase (e.g., ones as described herein). In some embodiments, an acyl amino acid-producing cell may comprise a modification (e.g., a genetic modification) such that expression and/or activity of a fatty acid modifying enzyme is modulated (e.g., increased or reduced) in the acyl amino acid-producing cell, as compared to that of a fatty acid modifying enzyme without such a modification.

Amino acid: As used herein, the term "amino acid," in its broadest sense, refers to any compound and/or substance that can be utilized in peptide synthesis (e.g., ribosomal or non-ribosomal synthesis). In some embodiments, an amino acid is any compound and/or substance that can be incorporated into a polypeptide chain, e.g., through formation of one or more peptide bonds. In some embodiments, an amino acid is any compound and/or substance that is a substrate for a peptide synthetase; in some embodiments, an amino acid is any compound and/or substance onto which a peptide synthetase can link an acyl entity, for example through formation of an amide bond. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide or an acyl amino acid. In some embodiments, a "naturally occurring" amino acid is one of the standard group of twenty amino acids that are the building blocks of polypeptides of most organisms, including alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain embodiments a "naturally occurring" amino acid may be one of those amino acids that are used less frequently and are typically not included in this standard group of twenty but are nevertheless still used by one or more organisms and incorporated into certain polypeptides. For example, the codons UAG and UGA normally encode stop codons in most organisms. However, in some organisms the codons UAG and UGA encode the amino acids selenocysteine and pyrrolysine. Thus, in certain embodiments, selenocysteine and pyrrolysine are naturally occurring amino acids.

Associated with: Two events or entities are "associated" with one another, as that term is used herein, if the presence, level and/or form of one is correlated with that of the other. For example, a particular entity (e.g., gene) is considered to be associated with a biological characteristic and/or function, if its presence, level, activity, and/or form correlates with the presence, absence, and/or level of the biological characteristic and/or function. As another example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Beta-hydroxy fatty acid: The term "beta-hydroxy fatty acid" as used herein refers to a fatty acid moiety (e.g., as described herein) comprising a hydroxy group at the beta position of the fatty acid moiety. As is understood by those skilled in the art, the beta position corresponds to the third carbon of the fatty acid chain, the first carbon being the carbon of the carboxylate group. Thus, when used in reference to an acyl amino acid (e.g., ones as described herein), where an amide moiety is formed between the carboxylate moiety of a fatty acid moiety and the nitrogen of an amino acid moiety, the beta position corresponds to the third carbon of the fatty acid moiety, with the first carbon being the carbon of the amide moiety. A beta-hydroxy fatty acid for use in accordance with the present disclosure may contain a linear or straight carbon chain. Additionally or alternatively, a beta-hydroxy fatty acid for use in accordance with the present disclosure may be a branched-chain fatty acid. In some such embodiments, a beta-hydroxy fatty acid may be terminally branched (i.e., having a branched carbon chain at one end of the fatty acid). In some such embodiments, a beta-hydroxy fatty acid may be a branched fatty acid of an iso type. In some embodiments, a beta-hydroxy fatty acid may be a branched fatty acid of an anteiso type. In some embodiments, a beta-hydroxy fatty acid for use in accordance with the present disclosure may be a mono-unsaturated or poly-unsaturated fatty acid. Alternatively, a beta-hydroxy fatty acid for use in accordance with the present disclosure may be a saturated fatty acid. A beta-hydroxy fatty acid for use in accordance with the present disclosure may contain any number of carbon atoms in the fatty acid chain. As non-limiting examples, a beta-hydroxy fatty acid may contain 3, 4, 5, 6, 7, 8, 9, 10, 11, 12, 3, 14, 15, 15, 16, 17, 18, 19, 20, 21, 22, 23, 24, 25, 26, 27, 28, 29, 30 or more carbon atoms. In some embodiments, a beta-hydroxy fatty acid that may be used in accordance with the present disclosure contains 13 to 15 carbons in the fatty acid chain. In some embodiments, a beta-hydroxy fatty acid is or comprises a saturated or unsaturated long-chain fatty acid with a 14-carbon backbone. In some embodiments, a beta-hydroxy fatty acid is or comprises myristic acid. Those of ordinary skill in the art will be aware of various beta-hydroxy fatty acids that can be used in accordance with the present disclosure.

Beta-hydroxy fatty acid linkage domain: The term "beta-hydroxy fatty acid linkage domain" as used herein refers to a domain (e.g., a polypeptide domain) that covalently links a beta-hydroxy fatty acid to an amino acid to form an acyl amino acid. A variety of beta-hydroxy fatty acid linkage domains are known to those skilled in the art. As will be understood by those skilled in the art, various beta-hydroxy fatty acid linkage domains typically exhibit specificity for one or more beta-hydroxy fatty acids. As one non-limiting example, a beta-hydroxy fatty acid linkage domain from surfactin synthetase is specific for beta-hydroxy myristic acid. Thus, in some embodiments, a beta-hydroxy fatty acid linkage domain from surfactin synthetase can be used in accordance with the present disclosure to construct an engineered polypeptide useful in the generation of an acyl amino acid in which beta-hydroxy myristic acid constitutes the fatty acid moiety or portion of the acyl amino acid. Different beta-hydroxy fatty acid linkage domains that exhibit specificity for other beta-hydroxy fatty acids (e.g., naturally or non-naturally occurring beta-hydroxy fatty acids) may be used in accordance with the present disclosure to generate any acyl amino acid of the practitioner's choosing.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Comparable: The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Corresponding to: As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, activity of linking two entities together etc.). In some embodiments, a domain can be an engineered domain. For example, in some embodiments, an engineered domain may refer to an engineered polypeptide moiety that correspond and/or show significant homology and/or identity to a naturally occurring polypeptide moiety, or to a reference polypeptide moiety. In some such embodiments, an engineered domain may share a characteristic structure (e.g., primary structure such as the amino acid sequence of a domain, and/or secondary, tertiary, quaternary, etc. structures); alternatively or additionally, such an engineered domain may exhibit one or more distinct functions that it shares with a reference polypeptide moiety. As will be understood by those skilled in the art, in many cases polypeptides are modular and may comprise one or more polypeptide domains; in some such embodiments, each domain can exhibit one or more distinct functions or characteristics of a polypeptide; or in some such embodiments, a plurality of domains may contribute to the overall function of a polypeptide. In some embodiments, the structure and/or function of many such domains are known to those skilled in the art.

Endogenous: As used herein, the term "endogenous" refers to a substance or process that is present or occurs naturally, e.g., in a non-recombinant host cell.

Engineered: Those of ordinary skill in the art, reading the present disclosure, will appreciate that the term "engineered", as used herein, refers to an aspect of having been manipulated and altered by the hand of man. For example, an engineered cell (e.g., an engineered microbial cell) refers to a cell that has been subjected to a manipulation, so that its genetic, epigenetic, and/or phenotypic identity is altered relative to an appropriate reference cell such as otherwise identical cell that has not been so manipulated. In some embodiments, the manipulation is or comprises a genetic manipulation. In some embodiments, an engineered cell is one that has been manipulated so that it contains and/or expresses a particular agent of interest (e.g., a protein, a nucleic acid, and/or a particular form thereof) in an altered amount and/or according to altered timing relative to such an appropriate reference cell. In reference to a polypeptide, an "engineered polypeptide" refers to a polypeptide that has been designed and/or produced by the hand of man. In some embodiments, an engineered polypeptide has an amino acid sequence that includes one or more sequence elements that do(es) not occur in nature. In some embodiments, an engineered polypeptide has an amino acid sequence that includes one or more sequence elements that does occur in nature, but that is present in the engineered polypeptide in a different sequence context (e.g., separated from at least one sequence to which it is linked in nature and/or linked with at least one sequence element to which it is not linked in nature) from that in which it occurs in nature. In some embodiments, an engineered polypeptide is one in which naturally-occurring sequence element(s) is/are separated from at least one sequence with which they/it is associated (e.g., linked) in nature and/or is otherwise manipulated to comprise a polypeptide that does not exist in nature. In various embodiments, an engineered polypeptide comprises two or more covalently linked polypeptide domains. Typically such domains may be linked via peptide bonds or other covalent linkages known to those skilled in the art. One or more covalently linked polypeptide domains of engineered polypeptides may be naturally occurring. Thus, in certain embodiments, engineered polypeptides described herein may comprise two or more covalently linked domains, at least one of which is naturally occurring. In certain embodiments, two or more naturally occurring polypeptide domains are covalently linked to generate an engineered polypeptide. For example, naturally occurring polypeptide domains from two or more different polypeptides may be covalently linked to generate an engineered polypeptide. In certain embodiments, naturally occurring polypeptide domains of an engineered polypeptide are covalently linked in nature, but are covalently linked in the engineered polypeptide in a way that is different from the way the domains are linked nature. For example, two polypeptide domains that naturally occur in the same polypeptide but which are separated by one or more intervening amino acid residues may be directly covalently linked (e.g., by removing the intervening amino acid residues) to generate an engineered polypeptide. Additionally or alternatively, two polypeptide domains that naturally occur in the same polypeptide which are directly covalently linked together (e.g., not separated by one or more intervening amino acid residues) may be indirectly covalently linked (e.g., by inserting one or more intervening amino acid residues) to generate an engineered polypeptide. In certain embodiments, one or more covalently linked polypeptide domains of an engineered polypeptide may not exist naturally. For example, such polypeptide domains may be engineered themselves.

Enriched: As used herein, the term "enriched" refers to an increase in the proportion of one or more components of a composition. For examples, in some embodiments, an acyl amino acid composition produced by technologies described herein may comprise a plurality of distinct acyl amino acids but is enriched in one or a few acyl amino acid (e.g., of a certain carbon length of a fatty acid portion), as compared to a reference product (e.g., an acyl amino acid composition that is not produced by technologies described herein). In some such embodiments, an acyl amino acid composition produced by technologies described herein contains a higher proportion of an acyl amino acid having a particular carbon length of a fatty acid portion (e.g., C14 for a fatty acid portion) than that of a reference product (e.g., an acyl amino acid composition that is not produced by technologies described herein), for example, by at least 10%, including, e.g., at least 20%, at least 30%, at least 40%, at least 50%, at least 60%, at least 70%, at least 80%, at least 90%, or more.

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Fatty acid: As used herein, the term "fatty acid" refers to a moiety having a carboxylic acid or carboxyl moiety with an aliphatic tail, e.g., in some embodiments, from 3 to 30 carbon atoms long. As will be understood by one of skill in the art, the carbon next to the carboxylic acid moiety is designated as $\alpha$; the next one is $\beta$, and so forth, while the carbon at the tail of a fatty acid (i.e., the carbon that is most distant from the carboxylic acid moiety of a fatty acid) is designated as $\omega$. Typically, carbon atoms that are close to the $\omega$ carbon are designated in relation to the $\omega$ carbon. For example, the third carbon starting from the $\omega$ carbon is designated as $\omega$-3 carbon. Accordingly, a carbon atom at a ($\omega$-n) position of a fatty acid refers to the $n^{th}$ carbon atom starting from the $\omega$ carbon, wherein n is 2 or higher (up to the length of the carbon chain), e.g., n is 2, 3, 4, 5, 6, etc. Fatty acids can be saturated, mono-unsaturated or poly-unsaturated. Fatty acids can be straight chain or branched (e.g., iso or anteiso). In some embodiments, a fatty acid may include one or more hydroxyl group. In some such embodiments, a fatty acid may be or comprises a beta-hydroxy fatty acid as described herein. Examples of fatty acids useful in the disclosure, include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linolenic acid (C18), gamma-linolenic acid (C18), arachidic acid (C20), gadoleic acid (C20), arachidonic acid (C20), eicosapentaenoic acid (C20), behenic acid (C22), crude acid (C22), docosahexaenoic acid (C22), lignoceric acid (C24) and hexacosanoic acid (C26). One of skill in the art will appreciate that other fatty acids may be useful for technologies described herein. In some aspects, a fatty acid may refer to a fatty acid portion of an acyl amino acid.

Fatty acid hydroxylase: As used herein, the term "fatty acid hydroxylase" generally refers to an enzyme or a functional domain thereof that adds a hydroxyl group to at least one carbon within the backbone of a fatty acid moiety. In some embodiments, a fatty acid hydroxylase may have specificity for a fatty acid of a particular structure (e.g., a branched fatty acid vs. a linear or straight fatty acid). In some embodiments, a fatty acid hydroxylase may have specificity for a fatty acid of a specific carbon length. For example, in some embodiments, a fatty acid hydroxylase may have specificity for a fatty acid having a carbon length of at least 3 or more, including, e.g., at least 4, at least 5, at least 6, at least 7, at least 8, at least 9, at least 10, at least 11, at least 12, at least 13, at least 14, at least 15, at least 16, at least 17, at least 18, at least 19, at least 20, or more. In some embodiments, a fatty acid hydroxylase may have specificity for adding a hydroxyl group to the carbon atom at one or more particular positions within the backbone of a fatty acid moiety. For example, in some embodiments, a fatty acid hydroxylase may have specificity for adding a hydroxyl group to the carbon atom at $\omega$-1, $\omega$-2, and/or $\omega$-3 position of a fatty acid moiety.

Fatty acid linkage domain: The term "fatty acid linkage domain" as used herein refers to a domain (e.g., a polypeptide domain) that covalently links a fatty acid to an amino acid to form an acyl amino acid. In some embodiments, a fatty acid linkage domain is or comprises a condensation domain; in some embodiments such a fatty acid linkage domain is part of a single polypeptide or a polypeptide complex with at least or only an adenylation domain, a thiolation domain, or both. A variety of fatty acid linkage domains are known in the art, such as for example, fatty acid linkage domains that are present in various peptide synthetase complexes that produce lipopeptides. In certain embodiments, a fatty acid linkage domain is or comprises a beta-hydroxy fatty acid linkage domain as described herein, e.g., linking a beta-hydroxy fatty acid to an amino acid. In some embodiments, a fatty acid linkage domain links a beta-amino fatty acid to an amino acid. In some embodiments, a fatty acid linkage domain links a fatty acid that is not modified at the beta position to an amino acid. In some embodiments, a fatty acid linkage domain links a fatty acid that does not have a hydroxyl group at the beta position to an amino acid. In some embodiments, a fatty acid linkage domain catalyzes condensation of a fatty acid and an amino acid so that an amide bond is formed, for example between a carboxylic acid moiety on a fatty acid and an amino moiety on an amino acid. In some embodiments, a fatty acid linkage domain is or comprises a domain that is at least 70% or more, including, e.g., at least 75%, at least 80%, at least 85%, at least 90%, at least 95% or higher (and up to 100%), identical at the amino acid level to that found in *Bacillus subtilis*'s surfactin synthetase SrfA protein.

Fatty acid methylase: As used herein, the term "fatty acid methylase" generally refers to an enzyme or a functional domain thereof that adds a methyl group to at least one carbon within the backbone of a fatty acid moiety. In some embodiments, a fatty acid methylase may have specificity for a fatty acid of a particular structure (e.g., a branched fatty acid vs. a linear or straight fatty acid). In some embodiments, a fatty acid methylase may have specificity for a fatty acid of a specific carbon length. For example, in some embodiments, a fatty acid methylase may have specificity for a fatty acid having a carbon length of at least 3 or more, including, e.g., at least 4, at least 5, at least 6, at least 7, at least 8, at least 9, at least 10, at least 11, at least 12, at least 13, at least 14, at least 15, at least 16, at least 17, at least 18, at least 19, at least 20, or more. In some embodiments, a fatty acid methylase may have specificity for adding a methyl group to the carbon atom at one or more particular positions within the backbone of a fatty acid moiety. For example, in some embodiments, a fatty acid methylase may have specificity for adding a methyl group to the carbon atom at $\omega$-1, $\omega$-2, and/or $\omega$-3 position of a fatty acid moiety.

Fatty acid modifying enzyme: As used herein, the term "fatty acid modifying enzyme" refers to an enzyme or a functional domain thereof that is capable of modifying one or more structural features of a fatty acid moiety (e.g., a fatty acid portion, such as a fatty acid backbone portion, of an acyl amino acid). Examples of such structural modifications include, but are not limited to hydroxylation and/or alkylation (e.g., methylation) of one or more carbon atoms within the backbone chain of a fatty acid moiety. In some embodiments, a fatty acid modifying enzyme may link a hydroxyl group to one or more carbon atoms of a fatty acid backbone chain. In some such embodiments, a fatty acid modifying enzyme may link a hydroxyl group to one or carbon atoms at the $\omega$-n position (e.g., $\omega$-1 position, $\omega$-2 position, $\omega$-3 position, etc.) of a fatty acid moiety (e.g., a fatty acid portion of an acyl amino acid). In some embodiments, a fatty acid modifying enzyme may link an alkyl group (e.g., C1-C5 such as a methyl group) to one or more carbon atoms of a fatty acid backbone chain. In some such embodiments, a fatty acid modifying enzyme may link an alkyl group (e.g., C1-C5 such as a methyl group) to one or carbon atoms at the $\omega$-n position (e.g., $\omega$-1 position, $\omega$-2 position, $\omega$-3 position, etc.) of a fatty acid moiety (e.g., a fatty acid portion of an acyl amino acid). In some embodiments, a fatty acid modifying enzyme may have specificity for a fatty acid of a particular structure (e.g., a branched fatty acid vs. a linear or straight fatty acid). In some embodiments, a fatty acid modifying enzyme may have specificity for a fatty acid of a specific carbon length. For example, in some embodiments, a fatty acid modifying enzyme may have specificity for a fatty acid having a carbon length of at least 3 or more, including, e.g., at least 4, at least 5, at least 6, at least 7, at least 8, at least 9, at least 10, at least 11, at least 12, at least 13, at least 14, at least 15, at least 16, at least 17, at least 18, at least 19, at least 20, or more. In some embodiments, a fatty acid modifying enzyme may have specificity for introduction of a modification (e.g., hydroxylation or methylation) to the carbon atom at one or more particular positions within the backbone of a fatty acid moiety. For example, in some embodiments, a fatty acid modifying enzyme may have specificity for introduction of a modification (e.g., hydroxylation or methylation) to the carbon atom at $\omega$-1, $\omega$-2, and/or $\omega$-3 position of a fatty acid moiety.

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequences. In some embodiments, a gene may include one or more regulatory elements that, for example, may control or impact one or more aspects of gene expression (e.g., cell-type-specific expression, inducible expression, etc.).

Genetic modification: As used herein, the term "genetic modification" refers to stable or transient alteration of expression and/or activity of a gene by introduction of exogenous DNA into a host cell. Exogenous DNA may be synthetic, or naturally derived, and may contain one or more genes, portions of one or more genes, or other useful DNA sequences. Exogenous DNA may be introduced to a cell by methods known in the art; one of ordinary skill in the art will appreciate that in some embodiments, viral vectors (e.g., retrovirus, modified herpes viral, herpes-viral, adenovirus, adeno-associated virus, and the like) may be used to introduce exogenous DNA into a host cell, or in some embodiments, direct DNA transfection (e.g., lipofection, calcium phosphate transfection, DEAE-dextran, electroporation, and the like) may be used. Other gene editing methods that are known in the art can also be used to carry out genetic modification. In some embodiments, a genetic modification can comprise an insertion of one or more nucleotides, a deletion of one or more nucleotides, a substitution of one or more nucleotides, a knockout, a knockin, a point mutation, a replacement of an endogenous nucleic acid sequence with a homologous, heterologous, or orthologous nucleic acid sequence, or a combination thereof.

Heterologous: As used herein, the term "heterologous" as used herein refers to a entity (e.g., nucleic acid or polypeptide) wherein at least one of the following is true: (a) the entity (e.g., nucleic acid or polypeptide) is foreign ("exogenous") to (that is, not naturally found in) a given host cell; (b) the entity (e.g., nucleic acid or polypeptide) comprises a nucleotide sequence that is naturally found in (that is, is "endogenous to") a given host cell, but the nucleotide sequence is produced in an unnatural (for example, greater than expected or greater than naturally found) amount in the cell; (c) the entity (e.g., nucleic acid or polypeptide) comprises a sequence that differs in sequence from an endogenous sequence, but the sequence encodes the same protein (having the same or substantially the same amino acid sequence) and is produced in an unnatural (for example, greater than expected or greater than naturally found) amount in the cell; or (d) the entity (e.g., nucleic acid or polypeptide) comprises two or more sequences that are not found in the same relationship to each other in nature (for example, the sequence is recombinant).

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Host cell: As used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, a host cell is a microbial cell such as, e.g., a bacterial cell.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

Increased or reduced: As used herein, these terms, or grammatically comparable comparative terms, indicate values that are relative to a comparable reference measurement. For example, in some embodiments, an assessed value achieved with an agent of interest may be "increased" relative to that obtained with a comparable reference agent. Alternatively or additionally, in some embodiments, an assessed value achieved in a subject or system of interest may be "increased" relative to that obtained in the same subject or system under different conditions (e.g., in the presence or absence of an agent of interest), or in a different, comparable subject or system (e.g., in a comparable subject or system that differs from the subject or system of interest in presence or absence of an agent of interest). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Moiety: Those skilled in the art will appreciate that a "moiety" is a defined chemical group or entity with a particular structure and/or or activity, as described herein.

Modulate: As used herein, the term "modulate" means either to cause a change in level and/or nature of an activity of interest. In some embodiments, modulation may refer to an increase in the level of an activity of interest, as compared to a reference level. In some embodiments, modulate may refer to a reduction in the level of an activity of interest, as compared to a reference level.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced. In some embodiments, isolation involves or requires disruption of covalent bonds (e.g., to isolate a polypeptide domain from a longer polypeptide and/or to isolate a nucleotide sequence element from a longer oligonucleotide or nucleic acid).

Naturally occurring: The term "naturally occurring", as used herein, refers to an agent or entity that is known to exist in nature.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present disclosure. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Operably linked: as used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

Peptide synthetase: The term "peptide synthetase", as used interchangeably with the term "peptide synthetase complex", refers to an enzyme that catalyzes the non-ribosomal production of peptides. As will be appreciated by those of ordinary skill in the art, peptide synthetase complexes are modular, and comprise individual peptide synthetase modules that perform different steps in the synthesis of the ultimate peptide; typically, each module performs one step (e.g., adds a single amino acid). A peptide synthetase complex may comprise a single enzymatic subunit (e.g., a single polypeptide), or may comprise two or more enzymatic subunits (e.g., two or more polypeptides). In some embodiments, a peptide synthetase complex may comprise at least one peptide synthetase domain, and may further comprise one or more additional domains such as for example, a fatty acid linkage domain, a thioesterase domain, a reductase domain, etc. In some embodiments, a peptide synthetase domain of a peptide synthetase complex may comprise two or more enzymatic subunits, with two or more peptide synthetase domains present in a given enzymatic subunit. For example the surfactin peptide synthetase complex (also referred to herein simply as "surfactin synthetase complex") comprises three distinct polypeptide enzymatic subunits: the first two subunits comprise three peptide synthetase domains, while the third subunit comprises a single peptide synthetase domain.

Peptide synthetase domain: The term "peptide synthetase domain" as used herein refers to a domain of a peptide synthetase. In some embodiments, a peptide synthetase domain minimally comprises three domains: an adenylation (A) domain (which is capable of selectively recognizing and activating a specific amino acid), a thiolation (T) domain (which is capable of tethering an activated amino acid to a cofactor via thioester linkage), and a condensation (C) domain (which is capable of linking one or more amino acids to successive units of a peptide synthetase through formation of amide bonds. A peptide synthetase domain typically recognizes and activates a single, specific amino acid, and in certain situations where the peptide synthetase domain is not the first domain in a peptide synthesis pathway, links the specific amino acid to the growing peptide chain. In some embodiments, a peptide synthetase domain may be or comprise a domain that is at least 70% or more, including, e.g., at least 75%, at least 80%, at least 85%, at least 90%, at least 95% or higher (and up to 100%), identical at the amino acid level to *Bacillus subtilis*'s surfactin synthetase complex SrfA-A polypeptide subunit's first peptide synthetase domain.

Polypeptide: The term "polypeptide" as used herein refers to a polymer of at least three amino acid residues. In some embodiments, a "polypeptide" has a structure as achieved through synthesis by ribosomal machinery in naturally occurring organisms. In some embodiments a "polypeptide" has a structure as achieved through chemical synthesis (e.g., in vitro). In some embodiments, a "polypeptide" has a structure as achieved through joining of a series of amino acids joined together by non-ribosomal machinery, such as by way of non-limiting example, polypeptides synthesized by peptide synthetases. Such non-ribosomally produced polypeptides exhibit a greater diversity in covalent linkages than polypeptides synthesized by ribosomes (although those skilled in the art will understand that the amino acids of ribosomally-produced polypeptides may also be linked by covalent bonds that are not peptide bonds, such as the linkage of cystines via disulfide bonds). In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Reductase Domain: The term "reductase domain" as used herein refers to a domain (e.g., polypeptide domain) that catalyzes release of an acyl amino acid produced by a peptide synthetase complex from the peptide synthetase complex. In certain embodiments, a reductase domain is covalently linked to a peptide synthetase domain and a fatty acid linkage domain such as a beta-hydroxy fatty acid linkage domain to generate an engineered polypeptide useful in the synthesis of an acyl amino acid. A variety of reductase domains are found in nature in nonribosomal peptide synthetase complexes from a variety of species. A non-limiting example of a reductase domain that may be used in accordance with the present disclosure includes the reductase domain from linear gramicidin (ATCC8185). However, a reductase domain that releases an acyl amino acid produced by a peptide synthetase complex from the peptide synthetase complex may be used in accordance with the present disclosure. In some embodiments, reductase domains are characterized by the presence of the consensus sequence: [LIVS-PADNK]-x(9)-{P}-x(2)-Y-[PSTAGNCV]-[STAGNQCIVM]-[STAGC]-K-{PC}-[SAGFYR]-[LIVMSTAGD]-x-{K}-[LIVMFYW]-{D}-x-{YR}-[LIVMFYWGAPTHQ]-[GSACQRHM], where square brackets ("[ ]") indicate amino acids that are typically present at that position, squiggly brackets ("{ }") indicate amino acids that amino acids that are typically not present at that position, and "x" denotes any amino acid or a gap. X(9) for example denotes any amino acids or gaps for nine consecutive positions. Those skilled in the art will be aware of methods to determine whether a give polypeptide domain is a reductase domain. In some embodiments, a reductase domain is or comprises a domain that is at least 70% or more, including, e.g., at least 75%, at least 80%, at least 85%, at least 90%, at least 95%, or more (and up to 100%), identical at the amino acid level to that found in *Bacillus brevis*'s linear gramicidin synthetase complex.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Regulatory element: As used herein, the term "regulatory element" refers to an entity (e.g., a polynucleotide entity) having gene regulatory activity, i.e. one that has the ability to affect the transcription or translation of an operably linked polynucleotide molecule (e.g., a gene encoding a polypeptide of interest). Regulatory elements including, e.g., but not limited to promoters, leaders, introns, and transcription termination regions, are molecules having gene regulatory activity which play an integral part in the overall expression of genes in biological cells. In some embodiments, by "regulatory element" it is intended to mean a series of nucleotides that determines if, when, and at what level a particular gene is expressed. The regulatory DNA sequences specifically interact with regulatory proteins or other proteins.

Specific: The term "specific" or "specificity" when used herein with reference to an entity having an activity, is understood by those skilled in the art to mean that the entity discriminates between potential target entities or states. For example, in some embodiments, a fatty acid linkage domain that is said to link a "specific" fatty acid to an amino acid if it links preferentially that target fatty acid to an amino acid in the presence of one or more competing alternative fatty acids. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of a domain for one or more other potential target entities (e.g., competitors). In some embodiments, specificity is evaluated relative to that of a reference specific domain. In some embodiments specificity is evaluated relative to that of a reference non-specific domain.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present disclosure, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Surfactin: Surfactin is cyclic lipopeptide that is naturally produced by certain bacteria, including the Gram-positive endospore-forming bacteria *Bacillus subtilis*. Surfactin is an amphiphilic molecule (having both hydrophobic and hydrophilic properties) and is thus soluble in both organic solvents and water. Surfactin exhibits exceptional surfactant properties, making it a commercially valuable molecule. Due to its surfactant properties, surfactin also functions as an antibiotic. For example, surfactin is known to be effective as an anti-bacterial, anti-viral, anti-fungal, anti-*mycoplasma* and hemolytic compound. Surfactin is capable of penetrating the cell membranes of all types of bacteria, including both Gram-negative and Gram-positive bacteria, which differ in the composition of their membrane. Gram-positive bacteria have a thick peptidoglycan layer on the outside of their phospholipid bilayer. In contrast, Gram-negative bacteria have a thinner peptidoglycan layer on the outside of their phospholipid bilayer, and further contain an additional outer lipopolysaccharide membrane. Surfactin's surfactant activity permits it to create a permeable environment for the lipid bilayer and causes disruption that solubilizes the membrane of both types of bacteria. In order for surfactin to carry out minimal antibacterial effects, the minimum inhibitory concentration (MIC) is in the range of 12-50 µg/ml. In addition to its antibacterial properties, surfactin also exhibits antiviral properties, and its known to disrupt enveloped viruses such as HIV and HSV. Surfactin not only disrupts the lipid envelope of viruses, but also their capsids through ion channel formations. Surfactin isoforms containing fatty acid chains with 14 or 15 carbon atoms exhibited improved viral inactivation, thought to be due to improved disruption of the viral envelope. Surfactin consists of a seven amino acid peptide loop, and a hydrophobic fatty acid chain (beta-hydroxy myristic acid) that is thirteen to fifteen carbons long. The fatty acid chain allows permits surfactin to penetrate cellular membranes. The peptide loop comprises the amino acids L-asparagine, L-leucine, glycine, L-leucine, L-valine and two D-leucines. Glycine and asparagine residues at positions 1 and 6 respectively, constitute a minor polar domain. On the opposite side, valine residue at position 4 extends down facing the fatty acid chain, making up a major hydrophobic domain. Surfactin is synthesized by the surfactin synthetase complex, which comprises the three surfactin synthetase polypeptide subunits SrfA-A, SrfA-B, and SrfA-C. The surfactin synthetase polypeptide subunits SrfA-A and SrfA-B each comprise three peptide synthetase domains, each of which adds a single amino acid to the growing surfactin peptide, while the monomodular surfactin synthetase polypeptide subunit SrfA-C comprises a single peptide synthetase domain and adds the last amino acid residue to the heptapeptide. Additionally the SrfA-C subunit comprises a thioesterase domain, which catalyzes the release of the product via a nucleophilic attack of the beta-hydroxy of the fatty acid on the carbonyl of the C-terminal Leu of the peptide, cyclizing the molecule via formation of an ester. The spectrum of the beta-hydroxy fatty acids was elucidated as iso, anteiso C13, iso, normal C14 and iso, anteiso C15, and a recent study has indicated that surfactin retains an R configuration at C-beta (Nagai et al., Study on surfactin, a cyclic depsipeptide. 2. Synthesis of surfactin B2 produced by *Bacillus* natto KMD 2311. *Chem Pharm Bull* (Tokyo) 44: 5-10, 1996).

Surfactin is a lipopeptide synthesized by the surfactin synthetase complex. Surfactin comprises seven amino acids, which are initially joined by peptide bonds, as well as a beta-hydroxy fatty acid covalently linked to the first amino acid, glutamate. However, upon addition the final amino acid (leucine), the polypeptide is released and the thioesterase domain of the SRFC protein catalyzes the release of the product via a nucleophilic attack of the beta-hydroxy of the fatty acid on the carbonyl of the C-terminal Leu of the peptide, cyclizing the molecule via formation of an ester, resulting in the C-terminus carboxyl group of leucine attached via a lactone bond to the b-hydroxyl group of the fatty acid.

Thioesterase domain: The term "thioesterase domain" as used herein refers to a polypeptide domain that catalyzes release of an acyl amino acid produced by a peptide synthetase complex from the peptide synthetase complex. A variety of thioesterase domains are found in nature in nonribosomal peptide synthetase complexes from a variety of species. A non-limiting example of a thioesterase domain that may be useful in technologies provided herein includes the thioesterase domain from the *Bacillus subtilis* surfactin synthetase complex, present in Srf-C subunit. However, any thioesterase domain that releases an acyl amino acid produced by a peptide synthetase complex from the peptide synthetase complex may be used in accordance with the present disclosure. In some embodiments, thioesterase domains are characterized by the presence of the consensus sequence: [LIV]-{KG}-[LIVFY]-[LIVMST]-G-[HYWV]-S-{YAG}-G-[GSTAC], where square brackets ("[ ]") indicate amino acids that are typically present at that position, and squiggly brackets ("{ }") indicate amino acids that amino acids that are typically not present at that position. Those skilled in the art will be aware of methods to determine whether a give polypeptide domain is a thioesterase domain. In some embodiments, a thioesterase domain is or comprises a domain that is at least 70% or more including, e.g., at least 75%, at least 80%, at least 85%, at least 90%, at least 95% or more (and up 100%), identical at the amino acid level to that found in *Bacillus subtilis*'s surfactin synthetase complex's SrfC subunit.

Vector: as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The forego-ing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

The present disclosure, among other things, provides technologies relating to generation of acyl amino acids and/or to improving yield of desirable acyl amino acids.

In some embodiments, provided technologies are particularly useful for making an acyl amino acid composition that is low in and/or is substantially free of acyl amino acids that are hydroxylated and/or methylated at one or more of the $\omega$-n positions (e.g., $\omega$-1, $\omega$-2, and/or $\omega$-3 positions) of a fatty acid portion of an acyl amino acid. In some embodiments, provided technologies are particularly useful for making an acyl amino acid composition that is enriched in and/or is substantially entirely of acyl amino acids that are hydroxylated and/or methylated at one or more of the $\omega$-n positions (e.g., $\omega$-1, $\omega$-2, and/or $\omega$-3 positions) of a fatty acid portion of an acyl amino acid. In some embodiments involving acyl amino acids produced by technologies described and/or utilized herein, such acyl amino acids comprise a beta-hydroxyl group.

In some embodiments, the present disclosure provides insights that a fatty acid portion of acyl amino acids produced in microbial cells such as *Bacillus* cells, are typically modified, for example, by hydroxylation and/or methylation, and that generation of such modified acyl amino acids can be controlled by use of strain engineering. In particular, the present inventors have demonstrated that modulating the level and/or activity of one or more fatty acid modifying enzymes (e.g., one or more fatty acid hydroxylases) present in microbial cells can increase or decrease modification (e.g., hydroxylation) of a fatty acid portion of an acyl amino acid at one or more $\omega$-n positions, where n≥1 (e.g., $\omega$-1, $\omega$-2, and/or $\omega$-3 positions). In some embodiments, such constructs can be engineered to increase modifications (e.g., hydroxylation) of a fatty acid portion of an acyl amino acid at one or more $\omega$-n positions, where n≥1 (e.g., $\omega$-1, $\omega$-2, and/or $\omega$-3 positions). In some embodiments, such constructs can be engineered to decrease modifications (e.g., hydroxylation) of a fatty acid portion of an acyl amino acid at one or more $\omega$-n positions, where n≥1 (e.g., $\omega$-1, $\omega$-2, and/or $\omega$-3 positions). Thus, the present disclosure teaches engineering acyl amino acid-producing cells to comprise a modification (e.g., a genetic modification) that modulates modification (e.g., hydroxylation and/or alkylation such as methylation) of a fatty acid portion of an acyl amino acid. In some embodiments, the present disclosure teaches engineering acyl amino acid-producing cells to comprise a genetic modification such that expression and/or activity of a fatty acid modifying enzyme is modulated. Such technologies can be useful in increasing yield of surfactants and/or fatty acids of interest (e.g., with or without $\omega$-n hydroxyl groups, where n≥1).

I. Fatty Acid Synthesis

Those skilled in the art are aware that fatty acid synthesis involves serial extension of an initiator moiety through addition of acetyl moieties (i.e., —$CH_2$—C(O)—) transferred from a malonate entity onto the growing fatty acid chain. The process can be conceptualized as involving several steps; FIG. 1 provides a visual depiction of exemplary such steps, using an acetyl initiation moiety):

1. Loading: each of the initiation moiety and the malonyl group is loaded (see arrows labeled (a) and (b) in FIG. 1) onto carrier proteins, so that an initiation entity and the malonate entity are generated;
2. Condensation: a 2-carbon acetyl moiety is transferred from the malonyl entity onto the initiation moiety in a reaction that releases the initiation moiety from its association with its carrier protein and also releases $CO_2$ from the malonate (see arrow (c) in FIG. 1);
3. Carbonyl Reduction: NADPH is used to reduce the carbonyl of the initiation moiety to an —OH group (see arrow (d) in FIG. 1);
4. Dehydration: removal of H2O removes the —OH group and generates a double bond (see arrow (e) in FIG. 1); and
5. Double Bond Reduction: in synthesis of saturated fatty acids, a second NADPH is used to reduce the generated double bond.

Repeating these steps extends the fatty acid chain, each time by two carbons. The terminal carbon in the fatty acid chain, which terminal carbon is contributed by the initiation moiety, is known as the "omega" ($\omega$) carbon.

In the particular example depicted in FIG. 1, the initiation moiety is an acetyl moiety, which has two carbons, so that fatty acid chains synthesized on such an acetyl initiation moiety typically will have an even number of carbons. Those skilled in the art are aware that fatty acids can be synthesized on any of a variety of initiation moieties, so that either even-numbered or odd-numbered fatty acid chains can be generated.

Furthermore, those skilled in the art are aware that certain possible initiation moieties may include one or more branches (e.g., may contain one or more pendant alkyl moieties, such as one or more methyl, ethyl, propyl, butyl, pentyl, hexyl, heptyl, octyl, nonyl, decyl, undecyl, dodecyl, or longer, moieties, which themselves may be branched or linear). See, for example, Julotok et al. *Appl. Environ Microbiol.* 76:1423, March 2010, which includes certain "potential fatty acid precursors" (i.e., sources of initiation moieties as described herein), including as depicted in its FIG. 1, which includes certain branched-chain amino acids (e.g., isoleucine, valine, leucine), branched-chain $\alpha$-keto acids (e.g., $\alpha$-keto-methylvalerate, $\alpha$-keto-isovalerate, $\alpha$-keto-isocaproate), short-branched-chain carboxylic acids (e.g., 2-methylbutyrate, isobutyrate, isovalerate), branched-chain C6-fatty acid isomers (e.g., 2-ethylbutyrate, 2-methylpentanoate, 3-methylpentanoate), short-chain carboxylic acids (e.g., acetate, propionate, pyruvate, lactate, butyrate, sodium diacetate), medium-chain carboxylic acids, pentanoate, hexanoate, heptanoate, octanoate, decanoate).

Still further, those skilled in the art will be aware that many or most (or all) microbial cells include enzymes that select initiation moieties and/or associate them with an appropriate carrier protein. Technologies have been developed to modify such enzymes (see, for example, WO2014/144649 which, among other things, describes engineering microbes so that altered fatty acid branching patterns are achieved, e.g., through altered selection and/or relative utilization of certain branched vs linear initiation moieties; in some embodiments, cells are engineered so that their ability to synthesize and/or utilize one or more natural initiation moieties or entities is reduced or abolished so that, in some embodiments, selection and/or use of initiation moieties or entities is dependent upon feeding relevant precursor(s) to the cells). In some embodiments, the present disclosure may utilize (e.g., further engineer) microbial cells with such altered ability to synthesize, select, and/or utilize one or more particular initiation moieties or entities.

II. Exemplary Engineered Cells for Generation of Acyl Amino Acids

In some aspects, provided are engineered cells that are capable of producing acyl amino acids and modulating hydroxylation and/or methylation of a fatty acid portion of such acyl amino acids. In some embodiments, such an engineered cell is an acyl amino acid-producing cell, which comprises a modification (e.g., a genetic modification) that modulates hydroxylation and/or methylation of a fatty acid portion of an acyl amino acid. In some embodiments, such an engineered cell expresses at least one peptide synthetase, which produces or synthesizes an acyl amino acid. In some embodiments, a cell that is engineered as described herein is one that contains one or more additional modifications relative to a reference (e.g., its parent) strain with respect to fatty acid synthesis. For example, in some embodiments a utilized cell may be one containing one or more modifications of fatty acid precursor metabolism, so that its ability to, and/or the frequency or efficiency with which it does, synthesize, select, and/or utilize a particular fatty acid precursor (e.g., fatty acid synthesis initiation moiety or entity) is altered relative to the reference strain. To give but a couple of examples, in some embodiments, a microbial cell that is engineered as described herein is one that lacks (e.g., has been engineered to lack, or otherwise lacks) one or more (e.g., all) $\alpha$-keto acid dehydrogenase activities, and/or expresses a $\beta$-ketoacyl ACP synthase activity.

a. Modification of a Fatty Acid Portion of an Acyl Amino Acid

In some embodiments involving a modification (e.g., a genetic modification) that modulates hydroxylation and/or methylation of a fatty acid portion of an acyl amino acid, such a modification may result in an increase in the number of hydroxyl and/or alkyl (e.g., methyl) groups of a fatty acid portion (e.g., a fatty acid backbone portion) of an acyl amino acid by at least 10% or more, including, e.g., at least 20%, at least 30%, at least 40%, at least 50%, at least 60%, at least 70%, at least 80%, at least 90%, at least 95%, or more, as compared to that when the modification is absent. In alternative embodiments, such a modification (e.g., a genetic modification) may result in a reduction in the number of hydroxyl and/or alkyl (e.g., methyl) groups of a fatty acid portion (e.g., a fatty acid backbone portion) of an acyl amino acid by at least 10% or more, including, e.g., at least 20%, at least 30%, at least 40%, at least 50%, at least 60%, at least 70%, at least 80%, at least 90%, at least 95%, or more, as compared to that when the modification is absent.

In some embodiments, a modification (e.g., genetic modification) that modulates hydroxylation and/or methylation of a fatty acid portion (e.g., a fatty acid backbone portion) of an acyl amino acid is or comprises a genetic modification such that expression and/or activity of a fatty acid modifying enzyme is modulated. For example, in some embodiments, such a genetic modification may result in an increase in expression and/or activity of a fatty acid modifying enzyme by at least 10% or more, including, e.g., at least 20%, at least 30%, at least 40%, at least 50%, at least 60%, at least 70%, at least 80%, at least 90%, at least 95%, or more, as compared to that when the modification is absent. For example, in some embodiments, such a genetic modification may result in a reduction in expression and/or activity of a fatty acid modifying enzyme by at least 10% or more, including, e.g., at least 20%, at least 30%, at least 40%, at least 50%, at least 60%, at least 70%, at least 80%, at least 90%, at least 95%, or more, as compared to that when the modification is absent. In some embodiments, expression and/or activity of a fatty acid modifying enzyme may be modulated (e.g., increased or reduced) by modifying a gene that encodes a fatty acid modifying enzyme, which includes, e.g., but are not limited to a genetic modification (e.g., as described and/or utilized herein) of a gene sequence that encodes a fatty acid modifying enzyme. In some embodiments, expression and/or activity of a fatty acid modifying enzyme may be modulated (e.g., increased or reduced) by modifying one or more regulatory elements that are operably linked to a gene that encodes a fatty acid modifying enzyme, which includes, e.g., a genetic modification (e.g., as described and/or utilized herein) of one or more such regulatory elements.

In some embodiments, a fatty acid modifying enzyme may be endogenous to an acyl amino acid-producing cell to be engineered. In some embodiments, a fatty acid modifying enzyme may be heterologous to an acyl amino acid-producing cell to be engineered. In some embodiments, a fatty acid modifying enzyme may be or comprise a fatty acid modifying enzyme from a *Bacillus* cell (e.g., a *Bacillus subtilis* cell). In some embodiments, a fatty acid modifying enzyme may be or comprise one or more cytochrome P450 enzymes, for example, from a *Bacillus* cell (e.g., a *Bacillus subtilis* cell). Table 1 shows corresponding genes encoding eight cytochrome P450 enzymes present in a *Bacillus* cell (e.g., a *Bacillus subtilis* cell). See, e.g., "Respiratory Cytochromes, Other Heme Proteins, and Heme Biosynthesis." Von Wachenfeldt and Hederstedt (2002) in *Bacillus subtilis* and its closest relatives, edited by Sonenshein, Hoch and Losick.

TABLE 1

Cytochrome P450 enzymes present in *Bacillus* cells
(e.g., *Bacillus subtilis* cells)

| Gene | Function |
| --- | --- |
| bioI | Putative fatty acid hydroxylase |
| cyp107J1 | unknown |
| cyp134A1 | unknown |
| cyp109B1 | unknown |
| cyp152A1 | Fatty acid hydroxylase |
| cyp102A2 | Fatty acid hydroxylase |
| cyp102A3 | Fatty acid hydroxylase |
| cyp107K1 | unknown |

In some embodiments, a fatty acid modifying enzyme in which expression and/or activity is modulated may be encoded by a gene listed in Table 1 above.

In some embodiments, a fatty acid modifying enzyme, in which expression and/or activity is modulated, is encoded by CYP107H (also called BioI). In some embodiments, such an enzyme is typically involved in biotin synthesis and/or hydroxylates myristic acid. See, e.g., Cryle et al., "Products of cytochrome P450(BioI) (CYP107H1)-catalyzed oxidation of fatty acids." *Org Lett*. (2003) 5(18):3341-4. In some embodiments, an exemplary amino acid sequence of such a fatty acid modifying enzyme encoded by CYP107H is set forth in SEQ ID NO: 3 (GenBank accession number CAB14997.1) as provided in the section entitled "Listing of Certain Sequences" below.

In some embodiments, a fatty acid modifying enzyme, in which expression and/or activity is modulated, is encoded by CYP107J1 (also called CypA). In some embodiments, expression of such an enzyme can increase when one or more polychlorinated biphenyls are fed to *Bacillus* cells, e.g., *Bacillus subtilis* cells—BioI increases in expression as well. See, e.g., Sun et al. "Formation of hydroxylated and methoxylated polychlorinated biphenyls by *Bacillus subtilis*: New insights into microbial metabolism" *Sci Total Environ*. (2018) 613-614: 54-61. In some embodiments, an increase in expression of such an enzyme can correlate with hydroxylation of one or more polychlorinated biphenyls, followed by subsequent methylation to create O-methyl modified polychlorinated biphenyls. In some embodiments, an exemplary amino acid sequence of such a fatty acid modifying enzyme encoded by CYP107J1 (GenBank accession number CAB14615.1) is set forth in SEQ ID NO: 4 as provided in the section entitled "Listing of Certain Sequences" below.

In some embodiments, a fatty acid modifying enzyme, in which expression and/or activity is modulated, is encoded by CYP134A1 (also called cyclo-L-leucyl-L-leucyl dipeptide oxidase, pulcheriminic synthase). In some embodiments, such an enzyme can participate in production of pulcheriminic acid. See, e.g., Cryle et al. "Structural and biochemical characterization of the cytochrome P450 CypX (CYP134A1) from *Bacillus subtilis*: a cyclo-L-leucyl-L-leucyl dipeptide oxidase." *Biochemistry*. (2010) 49(34): 7282-96. In some embodiments, an exemplary amino acid sequence of such a fatty acid modifying enzyme encoded by CYP134A1 is set forth in SEQ ID NO: 7 (GenBank accession number CAB15511.1) as provided in the section entitled "Listing of Certain Sequences" below.

In some embodiments, a fatty acid modifying enzyme, in which expression and/or activity is modulated, is encoded by CYP109B1. In some embodiments, such an enzyme can hydroxylate both α- and β-ionone in vivo and in vitro. See, e.g., Zhang et al. "The crystal structure of the versatile cytochrome P450 enzyme CYP109B1 from *Bacillus subtilis*" *Mol Biosyst*. (2015)11(3):869-81. In some embodiments, an exemplary amino acid sequence of such a fatty acid modifying enzyme encoded by CYP109B1 is set forth in SEQ ID NO: 6 (GenBank accession number CAB13078.1) as provided in the section entitled "Listing of Certain Sequences" below.

In some embodiments, a fatty acid modifying enzyme, in which expression and/or activity is modulated, is encoded by CYP152A1 (also called fatty acid b-hydroxylating cytochrome P450). In some embodiments, such an enzyme can catalyze hydrogen peroxide dependent hydroxylation of long chain fatty acids, producing α- and β-hydroxylated derivatives of myristic acid. See, e.g., Zhang et al. "The crystal structure of the versatile cytochrome P450 enzyme CYP109B1 from *Bacillus subtilis*" *Mol Biosyst*. (2015)11 (3):869-81. In some embodiments, an exemplary amino acid sequence of such a fatty acid modifying enzyme encoded by CYP152A1 is set forth in SEQ ID NO: 8 (GenBank accession number CAB12004.1) as provided in the section entitled "Listing of Certain Sequences" below.

In some embodiments, a fatty acid modifying enzyme, in which expression and/or activity is modulated, is encoded by CYP102A2. In some embodiments, CYP102A2 is a homolog of CYP102A3. See, e.g., Gustafsson et al. "Expression, purification, and characterization of *Bacillus subtilis* cytochromes P450 CYP102A2 and CYP102A3: flavocytochrome homologues of P450 BM3 from *Bacillus megaterium*" *Biochemistry* (2004) 43: 5474-87. In some embodiments, such an enzyme can hydroxylate myristic acid at the ω-1, ω-2 and ω-3 positions (e.g., 20%, 61% and 17%, respectively). In some embodiments, a fatty acid modifying enzyme encoded by CYP102A2 enzyme may prefer shorter unbranched fatty acids (e.g., lauric acid>myristic acid) and/ or branched myristic acid. See, e.g., id. In some embodiments, CYP102A2 can hydroxylate surfactant sodium dodecyl sulphate (SDS). See, e.g., Axarli et al. "Cytochrome P450 102A2 Catalyzes Efficient Oxidation of Sodium Dodecyl Sulphate: A Molecular Tool for Remediation." *Enzyme Res*. (2010) 2010:125429. In some embodiments, an exemplary amino acid sequence of such a fatty acid modifying enzyme encoded by CYP102A2 is set forth in SEQ ID NO: 1 (GenBank accession number CAB12544.1) as provided in the section entitled "Listing of Certain Sequences" below.

In some embodiments, a fatty acid modifying enzyme, in which expression and/or activity is modulated, is encoded by CYP102A3 (as known as cypB). In some embodiments, such an enzyme can hydroxylate myristic acid at the ω-1, ω-2 and ω-3 positions (e.g., 10%, 46% and 42%, respectively). In some embodiments, such an enzyme may prefer branched myristic acid relative to unbranched lauric or myristic acid. See, e.g., "Expression, purification, and characterization of *Bacillus subtilis* cytochromes P450 CYP102A2 and CYP102A3: flavocytochrome homologues of P450 BM3 from *Bacillus megaterium*" *Biochemistry* (2004) 43: 5474-87. In some embodiments, an exemplary amino acid sequence of such a fatty acid modifying enzyme encoded by CYP102A3 is set forth in SEQ ID NO: 2 (GenBank accession number CAB14658.1) as provided in the section entitled "Listing of Certain Sequences" below.

In some embodiments, a fatty acid modifying enzyme, in which expression and/or activity is modulated, is encoded by CYP107K1 (also known as polyketide biosynthesis cytochrome P450 PksS). In some embodiments, such an enzyme is involved in synthesis of bacillaene and the natural substrate of such an enzyme is or comprises dihydrobacillaene. In some embodiments, a CYP107K1 gene is located in the pksX cluster. In some embodiments, a CYP107K1 gene may be involved in reducing a particular double bond. See, e.g., Reddick et al. "PksS from *Bacillus subtilis* is a cytochrome P450 involved in bacillaene metabolism" *Biochem Biophys Res Commun*. (2007) 358(1):363-7. In some embodiments, an exemplary amino acid sequence of such a fatty acid modifying enzyme encoded by CYP107K1 is set forth in SEQ ID NO: 5 (GenBank accession number ABQ22962.1) as provided in the section entitled "Listing of Certain Sequences" below.

In some embodiments, a fatty acid modifying enzyme can be or comprise a fatty acid hydroxylase and/or a fatty acid methylase. In some embodiments, a fatty acid modifying enzyme is or comprises a fatty acid hydroxylase. In some such embodiments, a fatty acid hydroxylase may hydroxylate a linear or unbranched fatty acid, while in some such embodiments, a fatty acid hydroxylase may hydroxylate a branched fatty acid. In some embodiments, a fatty acid hydroxylase may be selected to hydroxylate a specific fatty acid, including, e.g., but not limited to caproic acid, caprylic acid, lauric acid, and myristic acid. In some embodiments, a fatty acid hydroxylase may be selected to hydroxylate a fatty acid as listed in Table 2 below. Examples of a fatty acid hydroxylase that may be involved in generation of acyl amino acids can be encoded by a gene selected from the group consisting of biol, cyp107h, cyp107J1, cyp134A1, cyp109B1, cyp152A1, cyp102A2, cyp102A3, cyp107K1, and combinations thereof. Various fatty acid modifying enzymes (e.g., fatty acid hydroxylases and/or fatty acid methylases) may be involved in generation of different kinds of acyl amino acids, for example, depending on the types of the fatty acid and/or amino acid moieties of acyl amino acids to be generated. One of ordinary skill in the art reading the present disclosure will appreciate that a proper fatty acid modifying enzyme may be selected for modification to modulate hydroxylation and/or methylation of a particular fatty acid portion of an acyl amino acid accordingly.

b. Peptide Synthetases

In some embodiments, an acyl amino acid-producing cell to be engineered may comprise a peptide synthetase (e.g., ones as described and/or utilized herein). In some embodiments, such a peptide synthetase may be endogenous to a host cell. In some such embodiments, a peptide synthetase may be heterologous to a host cell. In some embodiments, a peptide synthetase may be an engineered peptide synthetase. In some embodiments, a cell (e.g., a microbial cell) can be engineered to express a peptide synthetase. For example, in some embodiments, a cell (e.g., a microbial cell) can be engineered to contain a polynucleotide encoding a peptide synthetase.

In some embodiments, a peptide synthetase comprises a fatty acid linkage domain, a peptide synthetase domain; and a thioesterase domain. In some embodiments, a peptide synthetase comprises a fatty acid linkage domain, a peptide synthetase domain, and a reductase domain. In some embodiments, a peptide synthetase may be a peptide synthetase complex as described in WO2008/131002, the contents of which are incorporated herein by reference in their entirety for the purposes described herein. In some embodiments, one or more of a fatty acid linkage domain, a peptide synthetase domain, a thioesterase domain, and a reductase domain (e.g., ones as described in WO2008/131002, the contents of which are incorporated herein by reference in their entirety for the purposes described herein) may be used in a peptide synthetase. In some embodiments, a fatty acid linkage domain for use in a peptide synthetase is or comprises a domain that is at least 70% or more, including, e.g., at least 75%, at least 80%, at least 85%, at least 90%, at least 95% or higher (and up to 100%), identical at the amino acid level to that found in *Bacillus subtilis*'s surfactin synthetase SrfA protein. In some embodiments, a peptide synthetase domain for use in a peptide synthetase is or comprises a domain that is at least 70% or more, including, e.g., at least 75%, at least 80%, at least 85%, at least 90%, at least 95% or higher (and up to 100%), identical at the amino acid level to *Bacillus subtilis*'s surfactin synthetase complex SrfA-A polypeptide subunit's first peptide synthetase domain. In some embodiments, a reductase domain for use in a peptide synthetase is or comprises a domain that is at least 70% or more, including, e.g., at least 75%, at least 80%, at least 85%, at least 90%, at least 95%, or more (and up to 100%), identical at the amino acid level to that found in *Bacillus brevis*'s linear gramicidin synthetase complex. In some embodiments, a thioesterase domain is or comprises a domain that is at least 70% or more including, e.g., at least 75%, at least 80%, at least 85%, at least 90%, at least 95% or more (and up 100%), identical at the amino acid level to that found in *Bacillus subtilis*'s surfactin synthetase complex's SrfC subunit.

In some embodiments, a peptide synthetase may be or comprise a single peptide synthetase domain, not associated (e.g., not associated covalently and/or not otherwise associated) with, for example, another domain typically found in a peptide synthetase complex (e.g., a fatty acid linkage domain, a thioesterase domain, a reductase domain, etc. and/or a combination thereof). In some embodiments, such a single peptide synthetase domain (e.g., as described in WO2014/144649, the contents of which are incorporated herein by reference in their entirety for the purposes described herein) may be used in a peptide synthetase.

In some embodiments, peptide synthetase domains useful for the production of acyl amino acids as described herein, correspond and/or show significant homology and/or identity to a first peptide synthetase domain found in a naturally-occurring peptide synthetase complex. That is, as is known in the art, some peptide synthetase domains (i.e., some polypeptides comprising adenylation (A), thiolation (T), and condensation (C) domains) catalyze condensation of a fatty acid with an amino acid, and some catalyze condensation of two amino acids with one another. In some embodiments, peptide synthetase domains useful for the production of acyl amino acids as described herein are those that catalyze condensation of an amino acid with a fatty acid; such peptide synthetase domains are typically utilized herein in a form (e.g., as part of a polypeptide) that is separated from and/or does not include another peptide synthetase domain.

Many naturally-occurring peptide synthetase domains are found in nature within peptide synthetase complexes that synthesize lipopeptides. Such peptide synthetase complexes are multi-enzymatic complexes found in both prokaryotes and eukaryotes, and comprising one or more enzymatic subunits that catalyze the non-ribosomal production of a variety of peptides (see, for example, Kleinkauf et al., *Annu. Rev. Microbiol.* 41:259-289, 1987; see also U.S. Pat. Nos. 5,652,116 and 5,795,738). Non-ribosomal synthesis is also known as thiotemplate synthesis (see e.g., Kleinkauf et al.). Peptide synthetase complexes typically include one or more peptide synthetase domains that recognize specific amino acids and are responsible for catalyzing addition of the amino acid to the polypeptide chain.

The catalytic steps in the addition of amino acids typically include: recognition of an amino acid by the peptide synthetase domain, activation of the amino acid (formation of an amino-acyladenylate), binding of the activated amino acid to the enzyme via a thioester bond between the carboxylic group of the amino acid and an SH group of an enzymatic co-factor, which cofactor is itself bound to the enzyme inside each peptide synthetase domain, and formation of the peptide bonds among the amino acids.

A peptide synthetase domain comprises subdomains that carry out specific roles in these steps to form the peptide product. One subdomain, the adenylation (A) domain, is responsible for selectively recognizing and activating the amino acid that is to be incorporated by a particular unit of the peptide synthetase. The activated amino acid is joined to the peptide synthetase through the enzymatic action of another subdomain, the thiolation (T) domain, that is generally located adjacent to the A domain. Amino acids joined to successive units of the peptide synthetase are subsequently linked together by the formation of amide bonds catalyzed by another subdomain, the condensation (C) domain.

Peptide synthetase domains that catalyze the addition of D-amino acids often also have the ability to catalyze the recemization of L-amino acids to D-amino acids. Peptide synthetase complexes also typically include a conserved thioesterase domain that terminates the growing amino acid chain and releases the product.

The genes that encode peptide synthetase complexes have a modular structure that parallels the functional domain structure of the complexes (see, for example, Cosmina et al., *Mol. Microbiol.* 8:821, 1993; Kratzxchmar et al., *J. Bacteriol.* 171:5422, 1989; Weckermann et al., *Nuc. Acids res.* 16:11841, 1988; Smith et al., *EMBO J.* 9:741, 1990; Smith et al., *EMBO J.* 9:2743, 1990; MacCabe et al., *J. Biol. Chem.* 266:12646, 1991; Coque et al., *Mol. Microbiol.* 5:1125, 1991; Diez et al., *J. Biol. Chem.* 265:16358, 1990).

Hundreds of peptides are known to be produced by peptide synthetase complexes. Such nonribosomally-produced peptides often have non-linear structures, including cyclic structures exemplified by the peptides surfactin, cyclosporin, tyrocidin, and mycobacillin, or branched cyclic structures exemplified by the peptides polymyxin and bacitracin. Moreover, such nonribosomally-produced peptides may contain amino acids not usually present in ribosomally-produced polypeptides such as for example norleucine, beta-alanine and/or ornithine, as well as D-amino acids. Additionally or alternatively, such nonribosomally-produced peptides may comprise one or more non-peptide moieties that are covalently linked to the peptide. As one non-limiting example, surfactin is a cyclic lipopeptide that comprises a beta-hydroxy fatty acid covalently linked to the first glutamate of the lipopeptide. Other non-peptide moieties that are covalently linked to peptides produced by peptide synthetase complexes are known to those skilled in the art, including for example sugars, chlorine or other halogen groups, N-methyl and N-formyl groups, glycosyl groups, acetyl groups, etc.

Typically, each amino acid of the non ribosomally-produced peptide is specified by a distinct peptide synthetase domain. For example, the surfactin synthetase complex which catalyzes the polymerization of the lipopeptide surfactin consists of three enzymatic subunits. The first two subunits each comprise three peptide synthetase domains, whereas the third has only one. These seven peptide synthetase domains are responsible for the recognition, activation, binding and polymerization of L-Glu, L-Leu, D-Leu, L-Val, L-Asp, D-Leu and L-Leu, the amino acids present in surfactin.

A similar organization in discrete, repeated peptide synthetase domains occurs in various peptide synthetase genes in a variety of species, including bacteria and fungi, for example srfA (Cosmina et al., Mol. Microbiol. 8, 821-831, 1993), grsA and grsB (Kratzxchmar et al., J. Bacterial. 171, 5422-5429, 1989) tycA and tycB (Weckermann et al., Nucl. Acid. Res. 16, 11841-11843, 1988) and ACV from various fungal species (Smith et al., EMBO J. 9, 741-747, 1990; Smith et al., EMBO J. 9, 2743-2750, 1990; MacCabe et al., J. Biol. Chem. 266, 12646-12654, 1991; Coque et al., Mol. Microbiol. 5, 1125-1133, 1991; Diez et al., J. Biol. Chem. 265, 16358-16365, 1990). The peptide synthetase domains of even distant species contain sequence regions with high homology, some of which are conserved and specific for all the peptide synthetases. Additionally, certain sequence regions within peptide synthetase domains are even more highly conserved among peptide synthetase domains which recognize the same amino acid (Cosmina et al., Mol. Microbiol. 8, 821-831, 1992).

Exemplary lipopeptides synthesized by peptide synthetase complexes in nature are listed below in Table 2 (See also the NORINE database, which provides access to information on peptides and lipopeptides that are known to be, or in some cases believed to be, produced by peptide synthetase enzymes; still further, see Segolene et al. (Segolene et al., "NORINE: a database of nonribosomal peptides." *Nucleic Acids Research*, 36: D327-D331, 2008.)).

TABLE 2

Exemplary Lipopeptides Synthesized by Peptide Synthetases

| Lipopeptide Name | Fatty Acid Component | Fatty Acid Component name |
|---|---|---|
| [Ala4]surfactin aC15 | aC15:0-OH(3) | 3-hydroxy-12-methyl-tetradecanoic acid |

TABLE 2-continued

Exemplary Lipopeptides Synthesized by Peptide Synthetases

| Lipopeptide Name | Fatty Acid Component | Fatty Acid Component name |
|---|---|---|
| [Ala4]surfactin iC14 | iC14:0-OH(3) | 3-hydroxy-12-methyl-tridecanoic acid |
| [Ala4]surfactin iC15 | iC15:0-OH(3) | 3-hydroxy-13-methyl-tetradecanoic acid |
| [Ala4]surfactin nC14 | C14:0-OH(3) | 3-hydroxy-tetradecanoic acid |
| [Ala4]surfactin nC15 | C15:0-OH(3) | 3-hydroxy-pentadecanoic acid |
| [Gln1]surfactin | C15:0-OH(3) | 3-hydroxy-pentadecanoic acid |
| [Gln1]surfactin aC15 | aC15:0-OH(3) | 3-hydroxy-12-methyl-tetradecanoic acid |
| [Gln1]surfactin iC15 | iC15:0-OH(3) | 3-hydroxy-13-methyl-tetradecanoic acid |
| [Ile2.4.7]surfactin | aC15:0-OH(3) | 3-hydroxy-12-methyl-tetradecanoic acid |
| [Ile4.7]surfactin | aC15:0-OH(3) | 3-hydroxy-12-methyl-tetradecanoic acid |
| [Ile4]surfactin | aC15:0-OH(3) | 3-hydroxy-12-methyl-tetradecanoic acid |
| [Ile7]surfactin | aC15:0-OH(3) | 3-hydroxy-12-methyl-tetradecanoic acid |
| [Leu4]surfactin | aC15:0-OH(3) | 3-hydroxy-12-methyl-tetradecanoic acid |
| [Phe25] syringopeptin 25A | C10:0-OH(3) | 3-hydroxy-decanoic acid |
| [Val7]surfactin | aC15:0-OH(3) | 3-hydroxy-12-methyl-tetradecanoic acid |
| A21978C1 | aC11:0 | 8-methyldecanoic acid |
| A21978C2 | iC12:0 | 10-methylundecanoic acid |
| A21978C3 | aC13:0 | 10-methyldodecanoic acid |
| A54145 A | iC10:0 | decanoic acid |
| A54145 A1 | C10:0 | decanoic acid |
| A54145 B | C10:0 | decanoic acid |
| A54145 B1 | iC10:0 | decanoic acid |
| A54145 C | aC11:0 | 8-methyldecanoic acid |
| A54145 D | aC11:0 | 8-methyldecanoic acid |
| A54145 E | aC11:0 | 8-methyldecanoic acid |
| A54145 F | iC10:0 | decanoic acid |
| amphibactin B | C14:0-OH(3) | 3-hydroxy-tetradecanoic acid |
| amphibactin C | C16:1(9)-OH(3) | 3-hydroxy-9-hexadecenoic acid |
| amphibactin D | C14:0 | tetradecanoic acid |
| amphibactin E | C16:1(9) | 9-hexadecenoic acid |
| amphibactin F | C16:0-OH(3) | 3-hydroxy-hexadecanoic acid |
| amphibactin G | C18:1(9)-OH(3) | 3-hydroxy-9-octadecenoic acid |
| amphibactin H | C16:0 | hexadecanoic acid |
| amphibactin I | C18:1(9) | 9-octadecenoic acid |
| amphisin | C10:0-OH(3) | 3-hydroxy-decanoic acid |
| amphomycin A1437 A | iC13:1(3) | 11-methyl-3-dodecenoic acid |
| amphomycin A1437 B | iC14:1(3) | 12-methyl-3-tridecenoic acid |
| amphomycin A1437 D | aC15:1(3) | 12-methyl-3-tetradecenoic acid |
| amphomycin A1437 E | aC13:1(3) | 10-methyl-3-dodecenoic acid |
| apramide A | C8:0:1(7)-Me(2) | 2-methylact-7-ynoic acid |
| apramide B | C8:0:1(7) | oct-7-ynoic acid |
| apramide C | C9:1(8)-Me(2) | 2-methyl-8-nonenoic acid |
| apramide D | C8:0:1(7)-Me(2) | 2-methylact-7-ynoic acid |
| apramide E | C8:0:1(7) | oct-7-ynoic acid |
| apramide F | C9:1(8)-Me(2) | 2-methyl-8-nonenoic acid |
| apramide G | C8:0:1(7)-Me(2) | 2-methylact-7-ynoic acid |
| aquachelin A | C12:1(5) | 2-methyl-5-dodecenoic acid |
| aquachelin B | C12:0 | dodecanoic acid |
| aquachelin C | C14:1(7) | 7-tetradecenoic acid |
| aquachelin D | C14:0 | tetradecanoic acid |
| arthrofactin | C10:0-OH(3) | 3-hydroxy-decanoic acid |
| arylomycin A1 | iC11:0 | 9-methyldecanoic acid |
| arylomycin A2 | iC12:0 | 10-methylundecanoic acid |
| arylomycin A3 | C12:0 | dodecanoic acid |
| arylomycin A4 | aC13:0 | 10-methyldodecanoic acid |
| arylomycin A5 | iC14:0 | 12-methyl-tridecanoic acid |
| arylomycin B1 | iC11:0 | 9-methyldecanoic acid |
| arylomycin B2 | iC12:0 | 10-methylundecanoic acid |
| arylomycin B3 | C12:0 | dodecanoic acid |
| arylomycin B4 | aC13:0 | 10-methyldodecanoic acid |
| arylomycin B5 | iC13:0 | 11-methyldodecanoic acid |
| arylomycin B6 | iC14:0 | 12-methyl-tridecanoic acid |
| arylomycin B7 | aC15:0 | 12-methyltetradecanoic acid |
| bacillomycin D-1 | C14:0-NH2(3) | 3-amino-tetradecanoic acid |
| bacillomycin D-2 | iC15:0-NH2(3) | 3-amino-13-methyl-tetradecanoic acid |
| bacillomycin D-3 | aC15:0-NH2(3) | 3-amino-12-methyl-tetradecanoic acid |
| bacillomycin D-4 | C16:0-NH2(3) | 3-amino-hexadecanoic acid |
| bacillomycin D-5 | iC16:0-NH2(3) | 3-amino-14-methyl-pentadecanoic acid |
| bacillomycin F-1 | iC15:0-NH2(3) | 3-amino-13-methyl-tetradecanoic acid |
| bacillomycin F-2 | aC15:0-NH2(3) | 3-amino-12-methyl-tetradecanoic acid |
| bacillomycin F-3 | iC16:0-NH2(3) | 3-amino-14-methyl-pentadecanoic acid |
| bacillomycin F-4 | C16:0-NH2(3) | 3-amino-hexadecanoic acid |
| bacillomycin F-5 | iC17:0-NH2(3) | 3-amino-15-methyl-hexadecanoic acid |
| bacillomycin F-6 | aC17:0-NH2(3) | 3-amino-14-methyl-hexadecanoic acid |
| bacillomycin L-1 | C14:0-NH2(3) | 3-amino-tetradecanoic acid |
| bacillomycin L-2 | iC15:0-NH2(3) | 3-amino-13-methyl-tetradecanoic acid |
| bacillomycin L-3 | aC15:0-NH2(3) | 3-amino-12-methyl-tetradecanoic acid |
| bacillomycin L-4 | C16:0-NH2(3) | 3-amino-hexadecanoic acid |
| bacillomycin L-5 | iC16:0-NH2(3) | 3-amino-14-methyl-pentadecanoic acid |
| beauverolide A | C10:0-Me(4)-OH(3) | 3-hydroxy-4-methyl-decanoic acid |
| beauverolide B | C10:0-Me(4)-OH(3) | 3-hydroxy-4-methyl-decanoic acid |
| beauverolide Ba | C10:0-Me(4)-OH(3) | 3-hydroxy-4-methyl-decanoic acid |
| beauverolide C | C10:0-Me(4)-OH(3) | 3-hydroxy-4-methyl-decanoic acid |
| beauverolide Ca | C10:0-Me(4)-OH(3) | 3-hydroxy-4-methyl-decanoic acid |
| beauverolide D | C8:0-Me(4)-OH(3) | 4-methyl-3-hydroxy-octanoic acid |
| beauverolide E | C8:0-Me(4)-OH(3) | 4-methyl-3-hydroxy-octanoic acid |
| beauverolide Ea | C8:0-Me(4)-OH(3) | 4-methyl-3-hydroxy-octanoic acid |
| beauverolide F | C8:0-Me(4)-OH(3) | 4-methyl-3-hydroxy-octanoic acid |
| beauverolide Fa | C8:0-Me(4)-OH(3) | 4-methyl-3-hydroxy-octanoic acid |
| beauverolide H | C9:0-OH(3) | 3-hydroxy-nonanoic acid |
| beauverolide I | C8:0-Me(4)-OH(3) | 4-methyl-3-hydroxy-octanoic acid |
| beauverolide II | C10:0-Me(4)-OH(3) | 3-hydroxy-4-methyl-decanoic acid |
| beauverolide III | C8:0-Me(4)-OH(3) | 4-methyl-3-hydroxy-octanoic acid |
| beauverolide IV | C8:0-Me(4)-OH(3) | 4-methyl-3-hydroxy-octanoic acid |
| beauverolide Ja | C8:0-Me(4)-OH(3) | 4-methyl-3-hydroxy-octanoic acid |
| beauverolide Ka | C10:0-Me(4)-OH(3) | 3-hydroxy-4-methyl-decanoic acid |
| beauverolide L | C10:0-Me(4)-OH(3) | 3-hydroxy-4-methyl-decanoic acid |
| beauverolide La | C10:0-Me(4)-OH(3) | 3-hydroxy-4-methyl-decanoic acid |
| beauverolide M | C8:0-Me(4)-OH(3) | 4-methyl-3-hydroxy-octanoic acid |
| beauverolide N | C8:0-Me(4)-OH(3) | 4-methyl-3-hydroxy-octanoic acid |
| beauverolide V | C8:0-Me(4)-OH(3) | 4-methyl-3-hydroxy-octanoic acid |

TABLE 2-continued

Exemplary Lipopeptides Synthesized by Peptide Synthetases

| Lipopeptide Name | Fatty Acid Component | Fatty Acid Component name |
|---|---|---|
| beauverolide VI | C8:0-Me(4)-OH(3) | 4-methyl-3-hydroxy-octanoic acid |
| beauverolide VII | C8:0-Me(4)-OH(3) | 4-methyl-3-hydroxy-octanoic acid |
| beauverolide VIII | C10:0-Me(4)-OH(3) | 3-hydroxy-4-methyl-decanoic acid |
| callipeltin A | iC8:0-Me(2.4)-OH(3) | 2,4,6-trimethyl-3-hydroxy-heptanoic acid |
| callipeltin C | iC8:0-Me(2.4)-OH(3) | 2,4,6-trimethyl-3-hydroxy-heptanoic acid |
| callipeltin D | iC8:0-Me(2.4)-OH(3) | 2,4,6-trimethyl-3-hydroxy-heptanoic acid |
| callipeltin F | iC8:0-Me(2.4)-OH(3) | 2,4,6-trimethyl-3-hydroxy-heptanoic acid |
| callipeltin G | iC8:0-Me(2.4)-OH(3) | 2,4,6-trimethyl-3-hydroxy-heptanoic acid |
| callipeltin H | iC8:0-Me(2.4)-OH(3) | 2,4,6-trimethyl-3-hydroxy-heptanoic acid |
| callipeltin I | iC8:0-Me(2.4)-OH(3) | 2,4,6-trimethyl-3-hydroxy-heptanoic acid |
| callipeltin J | iC8:0-Me(2.4)-OH(3) | 2,4,6-trimethyl-3-hydroxy-heptanoic acid |
| callipeltin K | iC8:0-Me(2.4)-OH(3) | 2,4,6-trimethyl-3-hydroxy-heptanoic acid |
| callipeltin L | iC8:0-Me(2.4)-OH(3) | 2,4,6-trimethyl-3-hydroxy-heptanoic acid |
| carmabin A | C10:0:1(9)-Me(2.4) | 2,4-dimethyl-dec-9-ynoic acid |
| carmabin B | C10:0-Me(2.4)-oxo(9) | 9-oxo-2,4-dimethyldecanoic acid |
| CDA1b | C6:0-Ep(2) | 2-epoxy-hexanoic acid |
| CDA2a | C6:0-Ep(2) | 2-epoxy-hexanoic acid |
| CDA2b | C6:0-Ep(2) | 2-epoxy-hexanoic acid |
| CDA2d | C6:0-Ep(2) | 2-epoxy-hexanoic acid |
| CDA2fa | C6:0-Ep(2) | 2-epoxy-hexanoic acid |
| CDA2fb | C6:0-Ep(2) | 2-epoxy-hexanoic acid |
| CDA3a | C6:0-Ep(2) | 2-epoxy-hexanoic acid |
| CDA3b | C6:0-Ep(2) | 2-epoxy-hexanoic acid |
| CDA4a | C6:0-Ep(2) | 2-epoxy-hexanoic acid |
| CDA4b | C6:0-Ep(2) | 2-epoxy-hexanoic acid |
| cormycin A | C16:0-OH(3.4) | 3,4-dihydroxy-hexadecanoic acid |
| corpeptin A | C10:0-OH(3) | 3-hydroxy-decanoic acid |
| corpeptin B | C12:1(5)-OH(3) | 3-hydroxy-5-dodecenoic acid |
| corrugatin | C8:0 | octanoic acid |
| daptomycin | C10:0 | decanoic acid |
| enduracidin A | iC12:2(2.t4) | 10-methyl-2,trans-4-undecanoic acid |
| enduracidin B | aC13:2(2.t4) | 10-methyl-2,trans4-dodecenoic acid |
| fengycin A | C16:0-OH(3) | 3-hydroxy-hexadecanoic acid |
| fengycin B | C16:0-OH(3) | 3-hydroxy-hexadecanoic acid |
| friulimicin A | iC13:1(3) | 11-methyl-3-dodecenoic acid |
| friulimicin B | iC14:1(3) | 12-methyl-3-tridecenoic acid |
| friulimicin C | aC13:1(3) | 10-methyl-3-dodecenoic acid |
| friulimicin D | aC15:1(3) | 12-methyl-3-tetradecenoic acid |
| fuscopeptin A | C8:0-OH(3) | 3-hydroxy-octanoic acid |
| fuscopeptin B | C10:0-OH(3) | 3-hydroxy-decanoic acid |
| Ile-polymyxin B1 | aC9:0 | 6-methyloctanoic acid |
| Ile-polymyxin E1 | aC9:0 | 6-methyloctanoic acid |
| Ile-polymyxin E2 | iC8:0 | 6-methylheptanoic acid |
| Ile-polymyxin E8 | aC10:0 | 8-methyldecanoic acid |
| iturin A-1 | C13:0-NH2(3) | 3-amino-tridecanoic acid |
| iturin A-2 | C14:0-NH2(3) | 3-amino-tetradecanoic acid |
| iturin A-3 | aC15:0-NH2(3) | 3-amino-12-methyl-tetradecanoic acid |
| iturin A-4 | iC15:0-NH2(3) | 3-amino-13-methyl-tetradecanoic acid |
| iturin A-5 | C15:0-NH2(3) | 3-amino-pentadecanoic acid |
| iturin A-6 | iC16:0-NH2(3) | 3-amino-14-methyl-pentadecanoic acid |
| iturin A-7 | C16:0-NH2(3) | 3-amino-hexadecanoic acid |
| iturin A-8 | aC17:0-NH2(3) | 3-amino-14-methyl-hexadecanoic acid |
| iturin C-1 | iC14:0-NH2(3) | 3-amino-12-methyl-tridecanoic acid |
| iturin C-2 | aC15:0-NH2(3) | 3-amino-12-methyl-tetradecanoic acid |
| iturin C-3 | iC16:0-NH2(3) | 3-amino-14-methyl-pentadecanoic acid |
| iturin C-4 | aC17:0-NH2(3) | 3-amino-14-methyl-hexadecanoic acid |
| kulomo opunalide 1 | C8:0:1(7)-Me(2)-OH(3) | 2-methyl-3-hydroxy-7-octynoic acid |
| kulomo opunalide 2 | C8:0:1(7)-Me(2)-OH(3) | 2-methyl-3-hydroxy-7-octynoic acid |
| lichenysin A aC13 | aC13:0-OH(3) | 3-hydroxy-10-methyl-dodecanoic acid |
| lichenysin A aC15 | aC15:0-OH(3) | 3-hydroxy-12-methyl-tetradecanoic acid |
| lichenysin A aC17 | aC17:0-OH(3) | 3-hydroxy-14-methyl-hexadecanoic acid |
| lichenysin A iC12 | iC12:0-OH(3) | 3-hydroxy-10-methyl-undecanoic acid |
| lichenysin A iC13 | iC13:0-OH(3) | 3-hydroxy-11-methyl-dodecanoic acid |
| lichenysin A iC14 | iC14:0-OH(3) | 3-hydroxy-12-methyl-tridecanoic acid |
| lichenysin A iC15 | iC15:0-OH(3) | 3-hydroxy-13-methyl-tetradecanoic acid |
| lichenysin A iC16 | iC16:0-OH(3) | 3-hydroxy-14-methyl-pentadecanoic acid |
| lichenysin A iC17 | iC17:0-OH(3) | 3-hydroxy-15-methyl-hexadecanoic acid |
| lichenysin A nC12 | C12:0-OH(3) | 3-hydroxy-dodecanoic acid |
| lichenysin A nC13 | C13:0-OH(3) | 3-hydroxy-tridecanoic acid |
| lichenysin A nC14 | C14:0-OH(3) | 3-hydroxy-tetradecanoic acid |
| lichenysin A nC15 | C15:0-OH(3) | 3-hydroxy-pentadecanoic acid |
| lichenysin A nC16 | C16:0-OH(3) | 3-hydroxy-hexadecanoic acid |
| lokisin | C10:0-OH(3) | 3-hydroxy-decanoic acid |
| marinobactin A | C12:0 | dodecanoic acid |
| marinobactin B | C14:1(7) | 7-tetradecenoic acid |
| marinobactin C | C14:0 | tetradecanoic acid |
| marinobactin D1 | C16:1(9) | 9-hexadecenoic acid |
| marinobactin D2 | C16:1(7) | 7-hexadecenoic acid |
| marinobactin E | C16:0 | hexadecanoic acid |
| massetolide A | C10:0-OH(3) | 3-hydroxy-decanoic acid |
| massetolide B | C11:0-OH(3) | 3-hydroxy-undecanoic acid |
| massetolide C | C12:0-OH(3) | 3-hydroxy-dodecanoic acid |
| massetolide D | C10:0-OH(3) | 3-hydroxy-decanoic acid |
| massetolide E | C10:0-OH(3) | 3-hydroxy-decanoic acid |
| massetolide F | C10:0-OH(3) | 3-hydroxy-decanoic acid |
| massetolide G | C11:0-OH(3) | 3-hydroxy-undecanoic acid |
| massetolide H | C12:0-OH(3) | 3-hydroxy-dodecanoic acid |
| massetolide L | C10:0-OH(3) | 3-hydroxy-decanoic acid |
| mycosubtilin 1 | C16:0-NH2(3) | 3-amino-hexadecanoic acid |
| mycosubtilin 2 | iC16:0-NH2(3) | 3-amino-14-methyl-pentadecanoic acid |
| mycosubtilin 3 | iC17:0-NH2(3) | 3-amino-15-methyl-hexadecanoic acid |
| mycosubtilin 4 | aC17:0-NH2(3) | 3-amino-14-methyl-hexadecanoic acid |
| neamphamide A | iC8:0-Me(2.4)-OH(3) | 2,4,6-trimethyl-3-hydroxy-heptanoic acid |
| Nva-polymyxin E1 | aC9:0 | 6-methyloctanoic acid |
| papuamide A | aC11:2(4.6)-Me(2.6)-OH(2.3) | 2,3-dihydroxy-2,6,8-trimethyldeca-(4Z,6E)-dienoic acid |
| papuamide B | aC11:2(4.6)-Me(2.6)-OH(2.3) | 2,3-dihydroxy-2,6,8-trimethyldeca-(4Z,6E)-dienoic acid |
| papuamide C | aC11:2(4.6)-Me(2.6)-OH(2.3) | 2,3-dihydroxy-2,6,8-trimethyldeca-(4Z,6E)-dienoic acid |
| papuamide D | aC11:2(4.6)-Me(2.6)-OH(2.3) | 2,3-dihydroxy-2,6,8-trimethyldeca-(4Z,6E)-dienoic acid |
| pholipeptin | C10:0-OH(3) | 3-hydroxy-decanoic acid |
| plusbacin A1 | C14:0-OH(3) | 3-hydroxy-tetradecanoic acid |

TABLE 2-continued

Exemplary Lipopeptides Synthesized by Peptide Synthetases

| Lipopeptide Name | Fatty Acid Component | Fatty Acid Component name |
|---|---|---|
| plusbacin A2 | iC15:0-OH(3) | 3-hydroxy-13-methyl-tetradecanoic acid |
| plusbacin A3 | iC16:0-OH(3) | 3-hydroxy-14-methyl-pentadecanoic acid |
| plusbacin A4 | C16:0-OH(3) | 3-hydroxy-hexadecanoic acid |
| plusbacin B1 | C14:0-OH(3) | 3-hydroxy-tetradecanoic acid |
| plusbacin B2 | iC15:0-OH(3) | 3-hydroxy-13-methyl-tetradecanoic acid |
| plusbacin B3 | iC16:0-OH(3) | 3-hydroxy-14-methyl-pentadecanoic acid |
| plusbacin B4 | C16:0-OH(3) | 3-hydroxy-hexadecanoic acid |
| polymyxin B1 | aC9:0 | 6-methyloctanoic acid |
| polymyxin B2 | iC8:0 | 6-methylheptanoic acid |
| polymyxin B3 | C8:0 | octanoic acid |
| polymyxin B4 | C7:0 | heptanoic acid |
| polymyxin B5 | C9:0 | nonanoic acid |
| polymyxin B6 | aC9:0-OH(3) | 3-hydroxy-6-methyloctanoic acid |
| polymyxin E1 | aC9:0 | 6-methyloctanoic acid |
| polymyxin E2 | iC8:0 | 6-methylheptanoic acid |
| polymyxin E3 | C8:0 | octanoic acid |
| polymyxin E4 | C7:0 | heptanoic acid |
| polymyxin E7 | iC9:0 | 7-methyloctanoic acid |
| polymyxin M | aC9:0 | 6-methyloctanoic acid |
| pseudomycin A | C14:0-OH(3,4) | 3,4-dihydroxy-tetradecanoic acid |
| pseudomycin B | C14:0-OH(3) | 3-hydroxy-tetradecanoic acid |
| pseudomycin C | C16:0-OH(3,4) | 3,4-dihydroxy-hexadecanoic acid |
| pseudomycin C2 | C16:0-OH(3) | 3-hydroxy-hexadecanoic acid |
| pseudophomin A | C10:0-OH(3) | 3-hydroxy-decanoic acid |
| pseudophomin B | C12:0-OH(3) | 3-hydroxy-dodecanoic acid |
| putisolvin I | C6:0 | hexanoic acid |
| putisolvin II | C6:0 | hexanoic acid |
| putisolvin III | C6:0 | hexanoic acid |
| ramoplanin A1 | C8:2(2.t4) | 2,trans4-octenoic acid |
| ramoplanin A2 | iC9:2(2.t4) | 2,trans4-7-methyl-octenoic acid |
| ramoplanin A3 | iC10:2(2.t4) | 2,trans4-8-methyl-noneoic acid |
| serrawettin W1 | C10:0-OH(3) | 3-hydroxy-decanoic acid |
| serrawettin W2 | C10:0-OH(3) | 3-hydroxy-decanoic acid |
| surfactin aC13 | aC13:0-OH(3) | 3-hydroxy-10-methyl-dodecanoic acid |
| surfactin aC15 | aC15:0-OH(3) | 3-hydroxy-12-methyl-tetradecanoic acid |
| surfactin iC12 | iC12:0-OH(3) | 3-hydroxy-10-methyl-undecanoic acid |
| surfactin iC14 | iC14:0-OH(3) | 3-hydroxy-12-methyl-tridecanoic acid |
| surfactin iC15 | iC15:0-OH(3) | 3-hydroxy-13-methyl-tetradecanoic acid |
| surfactin iC16 | iC16:0-OH(3) | 3-hydroxy-14-methyl-pentadecanoic acid |
| surfactin nC13 | C13:0-OH(3) | 3-hydroxy-tridecanoic acid |
| surfactin nC14 | C14:0-OH(3) | 3-hydroxy-tetradecanoic acid |
| surfactin nC15 | C15:0-OH(3) | 3-hydroxy-pentadecanoic acid |
| syringafactin A | C10:0-OH(3) | 3-hydroxy-decanoic acid |
| syringafactin B | C10:0-OH(3) | 3-hydroxy-decanoic acid |
| syringafactin C | C10:0-OH(3) | 3-hydroxy-decanoic acid |
| syringafactin D | C12:0-OH(3) | 3-hydroxy-dodecanoic acid |
| syringafactin E | C12:0-OH(3) | 3-hydroxy-dodecanoic acid |
| syringafactin F | C12:0-OH(3) | 3-hydroxy-dodecanoic acid |
| syringomycin A1 | C10:0-OH(3) | 3-hydroxy-decanoic acid |
| syringomycin E | C12:0-OH(3) | 3-hydroxy-dodecanoic acid |
| syringomycin G | C14:0-OH(3) | 3-hydroxy-tetradecanoic acid |
| syringopeptin 22 PhvA | C10:0-OH(3) | 3-hydroxy-decanoic acid |
| syringopeptin 22 PhvB | C12:0-OH(3) | 3-hydroxy-dodecanoic acid |
| syringopeptin 22A | C10:0-OH(3) | 3-hydroxy-decanoic acid |
| syringopeptin 22B | C12:0-OH(3) | 3-hydroxy-dodecanoic acid |
| syringopeptin 25A | C10:0-OH(3) | 3-hydroxy-decanoic acid |
| syringopeptin 25B | C12:0-OH(3) | 3-hydroxy-dodecanoic acid |
| syringopeptin 508A | C12:0-OH(3) | 3-hydroxy-dodecanoic acid |
| syringopeptin 508B | C14:0-OH(3) | 3-hydroxy-tetradecanoic acid |
| syringopeptin SC 1 | C10:0-OH(3) | 3-hydroxy-decanoic acid |
| syringopeptin SC 2 | C12:0-OH(3) | 3-hydroxy-dodecanoic acid |
| syringostatin A | C14:0-OH(3) | 3-hydroxy-tetradecanoic acid |
| syringostatin B | C14:0-OH(3,4) | 3,4-dihydroxy-tetradecanoic acid |
| syringotoxin B | C14:0-OH(3) | 3-hydroxy-tetradecanoic acid |
| tensin | C10:0-OH(3) | 3-hydroxy-decanoic acid |
| tolaasin A | Pda | pentanedioic acid |
| tolaasin B | C8:0-OH(3) | 3-hydroxy-octanoic acid |
| tolaasin C | C8:0-OH(3) | 3-hydroxy-octanoic acid |
| tolaasin D | C8:0-OH(3) | 3-hydroxy-octanoic acid |
| tolaasin E | C8:0-OH(3) | 3-hydroxy-octanoic acid |
| tolaasin I | C8:0-OH(3) | 3-hydroxy-octanoic acid |
| tolaasin II | C8:0-OH(3) | 3-hydroxy-octanoic acid |
| tripropeptin A | iC13:0-OH(3) | 3-hydroxy-11-methyl-dodecanoic acid |
| tripropeptin B | iC14:0-OH(3) | 3-hydroxy-12-methyl-tridecanoic acid |
| tripropeptin C | iC15:0-OH(3) | 3-hydroxy-13-methyl-tetradecanoic acid |
| tripropeptin D | iC16:0-OH(3) | 3-hydroxy-14-methyl-pentadecanoic acid |
| tripropeptin E | iC17:0-OH(3) | 3-hydroxy-15-methyl-hexadecanoic acid |
| tripropeptin Z | iC12:0-OH(3) | 3-hydroxy-10-methyl-undecanoic acid |
| Val-polymyxin E1 | aC9:0 | 6-methyloctanoic acid |
| Val-polymyxin E2 | iC8:0 | 6-methylheptanoic acid |
| viscosin | C10:0-OH(3) | 3-hydroxy-decanoic acid |
| viscosinamide | C10:0-OH(3) | 3-hydroxy-decanoic acid |
| White Line Inducing Principle | C10:0-OH(3) | 3-hydroxy-decanoic acid |

Non-limiting examples of peptide synthetase complexes that may contain peptide synthetase domains useful in the identification, selection, design, and/or production of engineered peptide synthetases as described herein include, for example, surfactin synthetase, fengycin synthetase, arthrofactin synthetase, lichenysin synthetase, syringomycin synthetase, syringopeptin synthetase, saframycin synthetase, gramicidin synthetase, cyclosporin synthetase, tyrocidin synthetase, mycobacillin synthetase, polymyxin synthetase, bacitracin synthetase, and combinations thereof.

In some embodiments, an engineered peptide synthetase, peptide synthetase domain, or component thereof contains insertions, deletions, substitutions or inversions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acids as compared to its relevant reference.

In certain embodiments, such amino acid substitutions result in a peptide synthetase that comprises an amino acid whose side chain contains a structurally similar side chain as compared to the corresponding amino acid in the relevant reference. For example, amino acids with aliphatic side chains, including glycine, alanine, valine, leucine, and isoleucine, may be substituted for each other; amino acids having aliphatic-hydroxyl side chains, including serine and threonine, may be substituted for each other; amino acids having amide-containing side chains, including asparagine and glutamine, may be substituted for each other; amino acids having aromatic side chains, including phenylalanine, tyrosine, and tryptophan, may be substituted for each other; amino acids having basic side chains, including lysine, arginine, and histidine, may be substituted for each other; and amino acids having sulfur-containing side chains, including cysteine and methionine, may be substituted for each other.

In certain embodiments, amino acid substitutions result in a peptide synthetase that comprises an amino acid whose side chain exhibits similar chemical properties to a corresponding amino acid present in a relevant reference. For example, in certain embodiments, amino acids that comprise hydrophobic side chains may be substituted for each other. In some embodiments, amino acids may be substituted for each other if their side chains are of similar molecular weight or bulk. For example, an amino acid in a peptide synthetase may be substituted for an amino acid present in the relevant reference if its side chains exhibits a minimum/maximum molecular weight or takes up a minimum/maximum amount of space.

In certain embodiments, a peptide synthetase shows at least about 50, 55, 60, 65, 70, 75, 80, 85, 90, 91, 92, 93, 94, 95, 96, 97, 98, or 99% homology or identity with a relevant reference (e.g., over a portion that spans at least 5, 6, 7, 8, 9, 10, 15, 20, 25, 30, 35, 40, 45, 50, 60, 70, 80, 90, 100, 200, 300, 400, 500, 600, 700, 800, 900, 1000 or more amino acids).

c. Host Cells

In some embodiments, engineered polypeptides (e.g., an engineered polypeptide for modulation of hydroxylation and/or methylation of a fatty acid portion of an acyl amino acid, and/or an engineered peptide synthetase) are introduced in host cells for the production of acyl amino acids. As will be understood by those skilled in the art, in some embodiments, such engineered polypeptides are typically introduced into a host cell using an expression vector. Those skilled in the art reading the present disclosure will appreciate that various host cells may be used, and in some embodiments, a host cell is capable of receiving and propagating such an expression vector, and is capable of expressing the engineered polypeptide. In some embodiments, a host cell may be capable of producing an acyl amino acid. In some such embodiments, a host cell has been engineered to produce an acyl amino acid. An engineered polypeptide (e.g., an engineered polypeptide for modulation of hydroxylation and/or methylation of a fatty acid portion of an acyl amino acid, and/or an engineered peptide synthetase) may be transiently or stably introduced into a host cell of interest. For example, an engineered polypeptide (e.g., an engineered polypeptide for modulation of hydroxylation and/or methylation of a fatty acid portion of an acyl amino acid, and/or an engineered peptide synthetase) may be stably introduced by integrating the engineered polypeptide into the chromosome of a host cell. Additionally or alternatively, an engineered polypeptide (e.g., an engineered polypeptide for modulation of hydroxylation and/or methylation of a fatty acid portion of an acyl amino acid, and/or an engineered peptide synthetase) may be transiently introduced by introducing a vector comprising the engineered polypeptide into a host cell, which vector is not integrated into the genome of the host cell.

In certain embodiments, a host cell to be engineered is a microbial cell. In certain embodiments, a host cell to be engineered is a bacterium. Non-limiting examples of bacteria that are useful as host cells for technologies described and/or utilized herein include bacteria of the genera *Escherichia, Streptococcus, Bacillus*, and a variety of other genera known to those skilled in the art. In certain embodiments, an engineered polypeptide (e.g., an engineered polypeptide for modulation of hydroxylation and/or methylation of a fatty acid portion of an acyl amino acid, and/or an engineered peptide synthetase) is introduced into a host cell of the species *Bacillus subtilis*.

In some embodiments, microbial host cells (e.g., bacterial host cells) may be wild type. In some embodiments, microbial host cells (e.g., bacterial host cells) may comprise one or more genetic changes as compared to wild type species. In certain embodiments, such genetic changes are useful to production of acyl amino acids in a host cell. For example, such genetic changes may various advantages useful in production of acyl amino acids (e.g., increased viability, ability to utilize alternative energy sources, ability to make different acyl amino acids etc.).

In certain embodiments, a host cell to be engineered is a plant cell. Those skilled in the art are aware of standard techniques for introducing one or more engineered polypeptides (e.g., an engineered polypeptide such as ones described herein for modulation of hydroxylation and/or methylation of a fatty acid portion of an acyl amino acid, and/or an engineered peptide synthetase such as ones as described herein) into a plant cell of interest such as, without limitation, gold bombardment and *agrobacterium* transformation. In certain embodiments, the present disclosure provides a transgenic plant that comprises an engineered polypeptide (e.g., ones as described herein) that produces an acyl amino acid of interest (e.g., an acyl amino acid with or without a hydroxyl group at one or more ω-n C positions, where n≥1 (e.g., ω-1, ω-2, and/or ω-3 positions) of a fatty acid portion of the acyl amino acid). Any of a variety of plants species may be made transgenic by introduction of one or more engineered polypeptides (e.g., an engineered polypeptide such as ones described herein for modulation of hydroxylation and/or methylation of a fatty acid portion of an acyl amino acid, and/or an engineered peptide synthetase such as ones as described herein), such that the one or more engineered polypeptides are expressed in the plant and produces an acyl amino acid of interest (e.g., an acyl amino acid with or without a hydroxyl group at one or more ω-n C positions (e.g., ω-1, ω-2, and/or ω-3 positions) of a fatty acid portion of the acyl amino acid). In some embodiments, such one or more engineered polypeptides (e.g., ones as described herein) may be expressed in transgenic plants systemically (e.g. in each tissue at all times) or only in localized tissues and/or during certain periods of time. Those skilled in the art will be aware of various promoters, enhancers, etc. that may be employed to control when and where one or more engineered polypeptides (e.g., ones as described herein) are expressed.

Insects, including insects that are threats to agriculture crops, can produce acyl amino acids that are likely to be important or essential for insect physiology. For example, an enzyme related to peptide synthetases produces the product of the *Drosophila* Ebony genes, which product is important for proper pigmentation of the fly, but is also important for proper function of the nervous system (see e.g., Richardt et al., Ebony, a novel nonribosomal peptide synthetase for beta-alanine conjugation with biogenic amines in *Drosophila*, J. Biol. Chem., 278(42):41160-6, 2003). Acyl amino acids are also produced by certain Lepidoptera species that are a threat to crops. Thus, technologies provided herein may be used to produce transgenic plants that produce an acyl amino acid of interest that kills such insects or otherwise disrupts their adverse effects on crops. For example, an engineered polypeptide that produces an acyl amino acid that is toxic to a given insect species may be introduced into a plant such that insects that infest such a plant are killed. Additionally or alternatively, an engineered polypeptide that produces an acyl amino acid that disrupts an essential activity of the insect (e.g., feeding, mating, etc.) may be introduced into a plant such that the commercially adverse effects of insect infestation are minimized or eliminated. In certain embodiments, an acyl amino acid that mitigates an insect's adverse effects on a plant is an acyl amino acid that is naturally produced by such an insect. In certain embodiments, an acyl amino acid that mitigates an insect's adverse effects on a plant is a structural analog of an acyl amino acid that is naturally produced by such an insect. In some embodiments, technologies provided herein can be useful in allowing the construction of engineered polypeptides that produce any of a variety of acyl amino acids, which acyl amino acids can be used in controlling or eliminating harmful insect infestation of one or more plant species.

III. Exemplary Compositions

Technologies described and/or utilized herein are useful for making an acyl amino acid composition and/or a fatty acid composition. Thus, in some embodiments, the present disclosure provides engineered cells and/or methods of using such cells to produce compositions as described herein (e.g., that are or comprise particular acyl amino acids and/or fatty acids, optionally together with or isolated from one or more bacterial components and/or one or more enzymatic components).

a. Acyl Amino Acid Compositions and Methods of Generating and/or Isolating the Same Some aspects of the present disclosure provides compositions comprising acyl amino acids produced by engineered cells (e.g., ones as described herein). In some embodiments, such compositions comprise a collection of individual acyl amino acid molecules, that are related to one another in that they are each synthesized by provided engineered cells and together represent a distribution of chemical entities, varied in precise chemical structure (e.g., due to varying length and/or composition of acyl chains, linkages within such acyl chains and/or between an acyl chain and the amino acid, etc), that are synthesized by certain relevant peptide synthetase(s), under the conditions of synthesis (e.g., in vivo or in vitro). In some embodiments, a provided composition includes straight-chain acyl moieties, branched acyl moieties, and/or combinations thereof.

In some embodiments where an acyl amino acid composition is produced by engineered cells (e.g., ones as described herein) comprising a modification (e.g., a genetic modification) such that expression and/or activity of a fatty acid modifying enzyme (e.g., a fatty acid hydroxylase) is reduced and thereby reduce hydroxylation of a fatty acid portion of an acyl amino acid (e.g., reduce hydroxylation of carbon at one or more ω-n position, where n≥1 (e.g., ω-1, ω-2, and/or ω-3 positions) of a fatty acid portion of an acyl amino acid), less than 10%, less than 7.5%, less than 5%, less than 2.5%, less than 1%, less than 0.5%, less than 0.2%, or less than 0.1% of a fatty acid portion of an acyl amino acid in an acyl amino acid composition is hydroxylated (e.g., at one or more ω-n positons, where n≥1 (e.g., ω-1, ω-2, and/or ω-3 positions) of the fatty acid portion of the acyl amino acid), as compared to an acyl amino composition made using cells without such a modification. In some such embodiments, an acyl amino acid composition is substantially free of acyl amino acids that are hydroxylated at one or more ω-n positions, where n≥1 (e.g., ω-1, ω-2, and/or ω-3 positon) of the fatty acid portion of the acyl amino acid. In some embodiments, at least a fraction (e.g., at least 10% or more, including, e.g., at least 20%, at least 30%, at least 40%, at least 50%, at least 60%, at least 70%, at least 80%, at least 90%, at least 95%, or more and up to 100%) of acyl amino acid in such compositions provided herein may have a beta-hydroxyl group.

In some embodiments where an acyl amino acid composition is produced by engineered cells (e.g., ones as described herein) comprising a modification (e.g., a genetic modification) such that expression and/or activity of a fatty acid modifying enzyme (e.g., a fatty acid methylase) is reduced and thereby reduce methylation of a fatty acid portion of an acyl amino acid (e.g., reduce methylation of carbon at one or more ω-n position, where n≥1 (e.g., ω-1, ω-2, and/or ω-3 positions) of a fatty acid portion of an acyl amino acid), less than 10%, less than 7.5%, less than 5%, less than 2.5%, less than 1%, less than 0.5%, less than 0.2%, or less than 0.1% of a fatty acid portion of an acyl amino acid in an acyl amino acid composition is methylated (e.g., at one or more ω-n positons, where n≥1 (e.g., ω-1, ω-2, and/or ω-3 positions) of the fatty acid portion of the acyl amino acid), as compared to an acyl amino composition made using cells without such a modification. In some such embodiments, an acyl amino acid composition is substantially free of acyl amino acids that are methylated at one or more ω-n positions, where n≥1 (e.g., ω-1, ω-2, and/or ω-3 positon) of the fatty acid portion of the acyl amino acid. In some embodiments, at least a fraction (e.g., at least 10% or more, including, e.g., at least 20%, at least 30%, at least 40%, at least 50%, at least 60%, at least 70%, at least 80%, at least 90%, at least 95%, or more and up to 100%) of acyl amino acid in such compositions provided herein may have a beta-hydroxyl group.

In some embodiments where an acyl amino acid composition is produced by engineered cells (e.g., ones as described herein) comprising a modification (e.g., a genetic modification) such that expression and/or activity of a fatty acid modifying enzyme (e.g., a fatty acid hydroxylase) is increased and thereby increase hydroxylation of a fatty acid portion of an acyl amino acid (e.g., increase hydroxylation of carbon at one or more ω-n position, where n≥1 (e.g., ω-1, ω-2, and/or ω-3 positions) of a fatty acid portion of an acyl amino acid), greater than 60%, including, e.g., greater than 70%, greater than 80%, greater than 90%, greater than 95%, greater than 98%, or greater than 99% (and up to ~100%) of a fatty acid portion of an acyl amino acid in an acyl amino acid composition is hydroxylated (e.g., at one or more ω-n positons, where n≥1 (e.g., ω-1, ω-2, and/or ω-3 positions) of the fatty acid portion of the acyl amino acid), as compared to an acyl amino composition made using cells without such a modification. In some such embodiments, an acyl amino acid composition is substantially entirely of acyl amino acids that are hydroxylated at one or more ω-n positions, where n≥1 (e.g., ω-1, ω-2, and/or ω-3 positon) of the fatty acid portion of the acyl amino acid. In some such embodiments, at least a fraction (e.g., at least 10% or more, including, e.g., at least 20%, at least 30%, at least 40%, at least 50%, at least 60%, at least 70%, at least 80%, at least 90%, at least 95%, or more and up to 100%) of acyl amino acid in such compositions provided herein may have a beta-hydroxyl group.

In some embodiments where an acyl amino acid composition is produced by engineered cells (e.g., ones as described herein) comprising a modification (e.g., a genetic modification) such that expression and/or activity of a fatty acid modifying enzyme (e.g., a fatty acid methylase) is increased and thereby increase methylation of a fatty acid portion of an acyl amino acid (e.g., increase methylation of carbon at one or more ω-n position, where n≥1 (e.g., ω-1, ω-2, and/or ω-3 positions) of a fatty acid portion of an acyl amino acid), greater than 60%, including, e.g., greater than 70%, greater than 80%, greater than 90%, greater than 95%, greater than 98%, or greater than 99% (and up to ~100%) of a fatty acid portion of an acyl amino acid in an acyl amino acid composition is methylated (e.g., at one or more ω-n positons, where n≥1 (e.g., ω-1, ω-2, and/or ω-3 positions) of the fatty acid portion of the acyl amino acid), as compared to an acyl amino composition made using cells without such a modification. In some such embodiments, an acyl amino acid composition is substantially entirely of acyl amino acids that are methylated at one or more ω-n positions, where n≥1 (e.g., ω-1, ω-2, and/or ω-3 positon) of the fatty acid portion of the acyl amino acid. In some such embodiments, at least a fraction (e.g., at least 10% or more, including, e.g., at least 20%, at least 30%, at least 40%, at least 50%, at least 60%, at least 70%, at least 80%, at least 90%, at least 95%, or more and up to 100%) of acyl amino acid in such compositions provided herein may have a beta-hydroxyl group.

It will be appreciated by those skilled in the art that, in some embodiments, one feature of engineered production of acyl amino acids is that such engineered cells (e.g., as described herein) may not generate pure populations of single chemical entities. Thus, as noted above, in some embodiments, provided herein are acyl amino acid compositions comprising distributions of chemical entities. In some embodiments, provided herein are acyl amino acid compositions in which substantially all acyl amino acids comprise the same amino acid moiety, but the composition includes a distribution of acyl moieties. For examples, in some embodiments, an acyl amino acid composition produced by technologies described herein may comprise a plurality of distinct acyl amino acids, each having the same amino acid moiety, but is enriched in one or a few (e.g., 1, 2, or 3) acyl amino acid (e.g., of a certain carbon length of a fatty acid portion), as compared to a reference product (e.g., an acyl amino acid composition that is not produced by technologies described herein). In some such embodiments, an acyl amino acid composition produced by technologies described herein may contain a higher proportion of an acyl amino acid having a particular carbon length of a fatty acid portion (e.g., C14 for a fatty acid portion) than that of a reference product (e.g., an acyl amino acid composition that is not produced by technologies described herein), for example, by at least 10%, including, e.g., at least 20%, at least 30%, at least 40%, at least 50%, at least 60%, at least 70%, at least 80%, at least 90%, or more. In some embodiments, an acyl amino acid composition produced by technologies described herein may contain at least 70% or more (including, e.g., at least 80%, at least 90%, at least 95% or more) of an acyl amino acid having a particular carbon length of a fatty acid portion (e.g., C14 for a fatty acid portion), based on the total acyl amino acid molecules present in the composition.

Technologies provided herein can be used to produce a wide variety of acyl amino acids and compositions. In some embodiments, the amino acid moiety of acyl amino acids and compositions is or comprises one found in an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and/or valine. Alternatively or additionally, in some embodiments, the amino acid moiety of acyl amino acids and compositions is or comprises one found in an amino acid selected from the group consisting of selenocysteine and/or pyrrolysine. In some embodiments, the amino acid moiety of acyl amino acids and compositions is or comprises one found in an amino acid selected from the group consisting of norleucine, beta-alanine and/or ornithine. In some embodiments, the amino acid moiety of acyl amino acids and compositions is or comprises one found in an amino acid selected from the group consisting of L-amino acids. In some embodiments, the amino acid moiety of acyl amino acids and compositions is or comprises one found in an amino acid selected from the group consisting of D-amino acids. In some embodiments, the amino acid moiety of acyl amino acids and compositions is or comprises or comprises one found in an amino acid D-glu or D-diaminopropionic acid. Those skilled in the art will be aware of appropriate amino acid substrates, usable by acyl amino acid-producing cells as described herein (and, for example, by engineered peptide synthetases as described herein) to generate acyl amino acids containing such amino acid moieties. In some embodiments, the amino acid substrate is or comprises the recited amino acid. In some embodiments, the acyl moiety (or the fatty acid moiety) of acyl amino acids and compositions is or comprises a saturated fatty acid such as butyric acid, caproic acid, caprylic acid, capric acid, lauric acid, myristic acid, palmitic acid, stearic arachidic acid, behenic acid, and/or lignoceric acid. In some embodiments, the acyl moiety (or the fatty acid moiety) of acyl amino acids and compositions is or comprises an unsaturated fatty acid such as, without limitation, myristoleic acid, palmitoleic acid, oliec acid, linoleic acid, alpha-linolenic acid, arachidonic acid, eicosapentaenoic acid, erucic acid, and/or docosahexaenoic acid. Other saturated and unsaturated fatty acids whose acyl moieties may be used in accordance with the present disclosure. In certain embodiments, acyl amino acids and compositions produced by technologies provided herein may comprise beta-hydroxy fatty acids as the acyl moiety (or fatty acid moiety) of acyl amino acid. As is understood by those of ordinary skill in the art, beta-hydroxy fatty acids comprise a hydroxy group attached to the β carbon of the fatty acid chain.

In some embodiments, the present disclosure provides acyl amino acids and compositions in which the acyl group comprises or consists of fatty acid chains with a length within a range bounded by a shorter length selected from the group consisting of C2, C3, C4, C5, C6, C7, C8, C9, C10, C11, C12, C13, C14, C15, C16, C17, C18, C19, C20, C21, C22, C23, C24, C25, C26, C27, C28, C29, C30, and an upper length selected from the group consisting of C30, C29, C28, C27, C26, C25, C24, C23, C22, C21, C20, C19, C18, C17, C16, C15, C14, C13, C12, C11, C10, C9, C8, C7, C6, C5, C4, C3, C2, and C1, wherein the upper length is the same as or larger than the lower length. In some particular embodiments, the present disclosure provides acyl amino acids and compositions in which the acyl group comprises or consists of C10-C14 fatty acid chains, C13-16 fatty acid chains, C13-15 fatty acid chains, C16-24 fatty acid chains, C18-22 fatty acid chains, C18-24 fatty acid chains, C8-C16 fatty acid chains. In some embodiments, the present disclosure provides acyl amino acids and compositions in which the acyl group comprises, consists predominantly of, or consists of C5, C6, C7, C8, C9, C10, C11, C12, C13, C14, C15, C16, C17, C18, C19, and/or C20 fatty acid chains. In some embodiments, the present disclosure provides acyl amino acids and compositions in which the acyl group comprises, consists predominantly of, or consists of comprises, consists predominantly of, or consists of C8, C9, C10, C11, C12, C13, C14, C15, and/or C16 fatty acid chains. In some embodiments, the present disclosure provides acyl amino acids and compositions in which the acyl group comprises, consists predominantly of, or consists of comprises, consists predominantly of, or consists of C12, C13, C14, C15, and/or C16 fatty acid chains.

In some embodiments, the present disclosure provides acyl amino acid compositions in which all acyl amino acids comprise the same amino acid moiety or comprise an amino acid moiety from the same amino acid.

In some embodiments, the present disclosure provides acyl amino acid compositions in which different acyl amino acids within the composition have different acyl moieties (e.g., acyl moieties that differ, in composition, structure, branching, and/or length (of one or more chains). In some embodiments, such compositions predominantly include acyl moieties of a length (or within a range of lengths) as set forth above. In some such embodiments, such predominant acyl moieties are present in the composition at a level of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%<98%, or 99%.

In certain embodiments, technologies described and/or provided herein are useful in large-scale production of acyl amino acids. In certain embodiments, acyl amino acids are produced in commercially viable quantities using engineered cells, compositions, and/or methods as described and/or utilized herein. For example, engineered cells (e.g., ones as described and/or utilized herein) may be used to produce acyl amino acids to a level of at least 5, 6, 7, 8, 9, 10, 11, 12, 13, 14, 15, 16, 17, 18, 19, 20, 30, 40, 50, 60, 70, 80, 90, 100, 110, 120, 130, 140, 150, 150, 200, 250, 300, 400, 500, 600, 700, 800, 900, 1000 mg/L or higher. As will be appreciated by those skilled in the art, biological production of acyl amino acids using technologies provided herein achieves certain advantages over other methods of producing acyl amino acids. For example, as compared to chemical production methods, production of acyl amino acids using technologies provided herein may reduce downstream purification, which, for example, can increase yield of desirable products. In some embodiments, production of acyl amino acids using technologies provided herein may utilize more readily available and starting materials that are easier to store, reduce the necessity of using harsh and sometimes dangerous chemical reagents in the manufacturing process, reduce the difficulty and efficiency of the synthesis itself by utilizing host cells as bioreactors, and/or reduce the fiscal and environmental cost of disposing of chemical by-products. Other advantages will be clear to practitioners who utilize technologies provided herein.

Accordingly, some aspects of the present disclosure provide methods of making an acyl amino acid composition using such engineered cells. In some embodiments, such a method comprises a step of (a) culturing an engineered cell (e.g., ones as described and/or utilized herein) under conditions and for a time sufficient for an acyl amino acid composition to be made.

In some embodiments involving culturing, such culturing can comprise incubating an engineered cell (e.g., ones as described and/or utilized herein) in a culture medium that comprises one or more of a carbon source, a fatty acid, and an amino acid. In some embodiments, such a culture medium may comprise a carbon source, a fatty acid, and an amino acid. In some embodiments involving making an acyl glycinate composition, an amino acid present in a culture medium is or comprises glycine. In some embodiments involving making an acyl glutamate composition, an amino acid present in a culture medium is or comprises glutamic acid. In some embodiments involving making an acyl sarcosinate composition, an amino acid present in a culture medium is or comprises sarcosine. One of ordinary skill in the art reading the present disclosure will appreciate that other amino acids can be present in a culture medium for use in making other acyl amino acids.

In some embodiments, engineered cells and/or methods described and/or utilized herein produce acyl amino acid compositions that contain at least 50% or more, including, e.g., at least 60%, at least 70%, at least 80%, at least 90%, at least 95%, or more, of acyl amino acid molecules having a linear or straight-chain fatty acid portion.

In some embodiments, engineered cells and/or methods described and/or utilized herein produce acyl amino acid compositions that contain at least 50% or more, including, e.g., at least 60%, at least 70%, at least 80%, at least 90%, at least 95%, or more, of acyl amino acid molecules having a branched fatty acid portion. For example, in some embodiments where engineered cells (e.g., ones as described herein) comprising a genetic modification that reduces expression and/or activity of α-keto acid dehydrogenase (e.g., by knocking out bkdAA and bkdAB) are cultured in a culture medium comprising particular organic acids to initiate fatty acid synthesis, acyl amino acid with different branching patterns may be obtained by varying an organic acid substrate that is fed to such engineered cells. In some embodiments, when such engineered cells are cultured in a culture medium comprising isobutyrate, at least 50% or more, including, e.g., at least 60%, at least 70%, at least 80%, at least 90%, at least 95%, or more, of acyl amino acid molecules in a composition have an iso-branched fatty acid portion. In some such embodiments, at least 50% or more, including, e.g., at least 60%, at least 70%, at least 80%, at least 90%, at least 95%, or more, of acyl amino acid molecules in a composition may have a fatty acid chain length of about 10-20, or about 12-18, or about 13-15. In some such embodiments, at least 50% or more, including, e.g., at least 60%, at least 70%, at least 80%, at least 90%, at least 95%, or more, of acyl amino acid molecules in a composition have a fatty acid chain length of 14.

In some embodiments, when such engineered cells (e.g., comprising a genetic modification that reduces expression and/or activity of α-keto acid dehydrogenase (e.g., by knocking out bkdAA and bkdAB)) are cultured in a culture medium comprising 2-methylburic acid or 2-methylbutyrate, at least 50% or more, including, e.g., at least 60%, at least 70%, at least 80%, at least 90%, at least 95%, or more, of acyl amino acid molecules in a composition have a fatty acid portion with anteiso-branching. In some such embodiments, at least 50% or more, including, e.g., at least 60%, at least 70%, at least 80%, at least 90%, at least 95%, or more, of acyl amino acid molecules in a composition may have an odd-numbered chain length, e.g., in some embodiments, a fatty acid chain length of 11, 13, 15, 17, or 19. In some such embodiments, at least 50% or more, including, e.g., at least 60%, at least 70%, at least 80%, at least 90%, at least 95%, or more, of acyl amino acid molecules in a composition may have a fatty acid chain length of 13 or 15.

In some embodiments, when such engineered cells (e.g., comprising a genetic modification that reduces expression and/or activity of α-keto acid dehydrogenase (e.g., by knocking out bkdAA and bkdAB)) are cultured in a culture medium comprising isovaleric acid or isovalerate, at least 50% or more, including, e.g., at least 60%, at least 70%, at least 80%, at least 90%, at least 95%, or more, of acyl amino acid molecules in a composition have a fatty acid portion with iso-branching. In some such embodiments, at least 50% or more, including, e.g., at least 60%, at least 70%, at least 80%, at least 90%, at least 95%, or more, of acyl amino acid molecules in a composition may have an odd-numbered chain length, e.g., in some embodiments, a fatty acid chain length of 11, 13, 15, 17, or 19. In some such embodiments, at least 50% or more, including, e.g., at least 60%, at least 70%, at least 80%, at least 90%, at least 95%, or more, of acyl amino acid molecules in a composition may have a fatty acid chain length of 13 or 15.

In some embodiments, acyl amino acids are produced in association with one or more components of a cell and/or with a peptide synthetase. In some embodiments, acyl amino acid compositions are subjected to one or more isolation procedures, for example as is known in the art, e.g., to separate produced acyl amino acid compounds from one or more components of their production system (e.g., from a peptide synthetase or component or domain thereof, and/or from one or more components of a cell such as an engineered cell.

b. Generation of Fatty Acids from Acyl Amino Acids

In some embodiments, acyl amino acids produced by technologies provided herein can be cleaved to generate free fatty acids (e.g., branched or linear fatty acids, and/or hydroxylated fatty acids) and amino acids. For example, in some embodiments, acyl amino acids produced by technologies provided herein can be treated with an acid and/or heat to break the amide bond that links the fatty acid moiety to the amino acid moiety, thereby generating free fatty acids and amino acids. In some embodiments, acyl amino acids produced by technologies provided herein can be cleaved to generate free fatty acid molecules and amino acid molecules using acylases. Exemplary methods for generating fatty acids from acyl amino acids are described in WO 2017/011592, the contents of which are incorporated herein by reference in its entirety for the purposes described herein. Those skilled in the art will appreciate that acyl amino acids produced by technologies provided herein can be cleaved to generate fatty acids using methods known in the art, e.g., as described in Examples 3 and 4 of WO 2017/011592.

Such free fatty acids generated from acyl amino acids can be used in various applications, e.g., directly as personal care products, and/or subject to further processing to make derivative products, such as surfactants that have new head groups different from the head group (amino acid) that was connected to the fatty acid in which it was originally produced.

c. Characterization, Formulation, and/or Incorporation of Acyl Amino Acid and/or Fatty Acids Those skilled in the art, reading the present disclosure, will appreciate that acyl amino acids, fatty acids, and/or other entities generated in accordance with the present disclosure may be characterized and/or assessed for one or more attributes (e.g., desirable attributes), including for suitability in one or more particular commercial applications. Acyl amino acids can be assessed for their usefulness as surfactants, therapeutics (e.g., signaling molecules), anti-microbials, preservatives, anti-wrinkle agents, anti-acne agents and skin moisturizing agents, and other uses.

Those skilled in the art, reading the present disclosure will further appreciate that, in some embodiments, compositions as provided herein (e.g., that are or comprise acyl amino acids, fatty acids, and/or engineered cells or components thereof, etc.) can be utilized in particular commercial contexts, included by being formulated and/or otherwise incorporated into products such as, for example, acyl amino acids in personal care product, home care products, cosmetics, detergents, fabric softeners, oil field, agricultural and food products, and in the production and care of textiles; and fatty acids for use as polyols for manufacturing of polyurethanes and other polymers, anti-corrosives, lubricants, polishes, textile additives, soaps, shaving products, emollients and hydrocarbon fuels.

EXEMPLIFICATION

Figure 2:
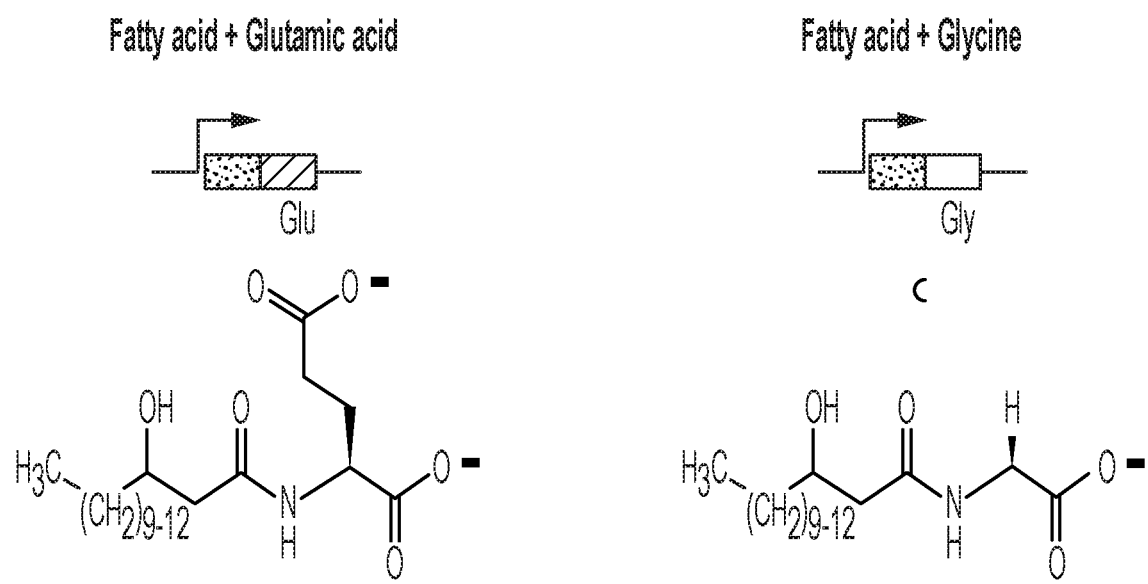
FIG. 2 depicts exemplary acyl amino acids produced by engineered enzymes and/or microbial cells described and/or utilized herein. The present inventors have previously developed engineered enzymes and/or microbial cells that catalyze production of an acyl amino acid (for example, β-hydroxy myristoyl glutamate), which engineered enzymes and/or microbial cells comprise at least one domain that is specific for a particular fatty acid and at least one domain that is specific for a particular amino acid. Such engineered enzymes are modular.

Example 1: Characterization of Acyl Amino Acids Produced by Existing Fermentation Methods The present inventors have previously engineered peptide synthetase enzymes to produce acyl amino acid surfactants. See, e.g., Reznik et al., *Appl Microbiol Biotechnol* (2010) 86(5): 1387-97. The present inventors have found that a significant fraction of acyl glutamate (e.g., one having a structure as shown in FIG. 2) produced by previously-engineered peptide synthetase enzymes (see, for example, as shown in FIG. 2) has a mass of about 16 Dalton greater than the expected mass (approximately 300.42 Dalton), as determined by liquid chromatograph-mass spectrometry (LC-MS), which is commonly to measure the quantity of acyl amino acids produced by engineered microbial strains. The additional mass of about 16 Dalton suggests that a hydrogen of an acyl glutamate has been replaced with a hydroxyl.

Significantly, the same phenomenon (a fraction of an acyl amino acid composition is 16 Dalton larger than expected) was observed regardless of whether the amino acid component of the acyl amino acid is glutamate or glycine. This observation indicates that a modification occurs on the fatty acid portion of an acyl amino acid, rather than on the amino acid portion.

Under certain growth conditions, the side-product with a greater mass can be as much as 99% of the total acyl amino acid composition. While the level of production of such a side-product can be reduced by controlling fermentation conditions, the present inventors have discovered use of strain engineering to reduce or completely eliminate production of the side-product. See, e.g., Example 2. In some circumstances where it is desirable to produce an acyl amino acid composition that is substantially free of acyl amino acids that have a hydroxyl group, e.g., at the ω-n position (where n≥1) of a fatty acid portion of the acyl amino acid, reducing or eliminating undesirable hydroxylation of a fatty acid portion of an acyl amino acid can be advantageous because modified molecules do not have the same physical properties as those of acyl amino acids without undesirable hydroxylation in some circumstances, and removing such modified molecules may reduce yield of desirable acyl amino acids. For example, in some embodiments, acid precipitation may be used as part of a purification protocol, and however, modified molecules do not precipitate efficiently, thereby reducing yield of desirable acyl amino acids.

Example 2: Engineering of Microbial Cells to Comprise a Modification that Modulates Hydroxylation of a Fatty Acid Portion of an Acyl Amino Acid The present Example describes construction and characterization of microbial cells that are engineered to produce acyl amino acids and to modulate hydroxylation of a fatty acid portion of the produced acyl amino acids. While this study assessed a reduction of hydroxylation of a fatty acid portion of an acyl amino acid when a gene associated with fatty acid hydroxylation is inactivated, those skilled in the art reading the present disclosure will also appreciate that hydroxylation of a fatty acid portion of an acyl amino acid can also be increased when a gene associated with fatty acid hydroxylation is activated or over-expressed. Further, those skilled in the art reading the present disclosure will also appreciate that technologies provided herein can be used to produce different acyl amino acids.

In this Example, microbial cells that produce acyl amino acids were engineered to inactivate a gene encoding a fatty acid hydroxylase (e.g., cypB). Accordingly, the present Example describes, for example, engineering a CypB-Upp-Kan construct. For example, genomic DNA from OKB105Δ (upp)Spect$^R$FA-GLU-TE-MG that encodes the cypB gene was amplified, for example, using primers:

```
55748:
5'-AAACTAAAAAAGGGTAGCCTAAAAA-3' and

55749:
5'-AAAGAAGTTTTAGCTATAGGAGATTCC-3'.
```

The cypB gene and flanking sequence were amplified, for example, via nested PCR using primers:

55789: 5'-GATTGTACTGAGAGTGCAC-CATAtGCTTGCATTAAGAGAAATTTACA-3'; and

55790: 5'-GCGGTATTTCACACCGcAGGGAATA-CAAGTCTTTTAATCAG-3'. Such a fragment was annealed to a PCR product obtained from a template vector pUC19 amplified, for example, with primers 50348 (5'-GCGGTGTGAAATACCGcACA-GATGCGTAAGGAGAAAA-3') and 50349 (5'-ATATGGTGCACTCTCAGTACAATCTGCTCT-GATGCCGCA-3'). The annealed mixture was transformed into cells (e.g., AbleK cells) to produce the plasmid cypB-bs168-inter-1-pUC19c, the nucleotide sequence of which is shown below:

| | cypB-bs168-inter-1-pUC19c | |
|---:|---|---:|
| 1 | TCGCGCGTTTCGGTGATGACGGTGAAAACCTCTGACACATGCAGCTCCCG | 50 |
| 51 | GAGACGGTCACAGCTTGTCTGTAAGCGGATGCCGGGAGCAGACAAGCCCG | 100 |
| 101 | TCAGGGCGCGTCAGCGGGTGTTGGCGGGTGTCGGGGCTGGCTTAACTATG | 150 |
| 151 | CGGCATCAGAGCAGATTGTACTGAGAGTGCACCATATGCTTGCATTAAGA | 200 |
| 201 | GAAATTTACAGGGTGCTTCAAATTGACGGCCGGTTTTATATCAGTATTGA | 250 |
| 251 | CACAAATACCGGTGAAAAAGAGAAAACGTATATTCAACTGCTGAAAGACC | 300 |
| 301 | AGCATTTCAGGGATCTTTCTGTTATCAGGCGTGCTTCCTGTCTATGTATT | 350 |
| 351 | GTGGCTGTTAAATAAAAAATTTCTCGGGAAATATATCCAAGATCCTCGTA | 400 |
| 401 | TTAGGATTTGGGTATATTTTCTTAATTTTTTATTTTTTGCATATACTTTA | 450 |
| 451 | TATTAAAAAAAGTTTTTTTCATATAAACTTATAACAGAAGAAAGAACAAA | 500 |
| 501 | GAGGTGATATCAGACAGGGCAGACATTCTTTGTGAACAAAAGGAATGAAT | 550 |
| 551 | ATTCATTCCGTAAACGAATCGGAGGTTGTCAGATTACATGATATCCGCAT | 600 |
| 601 | CCAGCAGTAAATACGACATGATTATGAAAGCGTCAGTCTCACTTTTTACG | 650 |
| 651 | GAAAGGGGTTTTGACGCTACCACTATTCCTATGATAGCTGAACGTGCTCA | 700 |
| 701 | TGTAGGGACAGGAACGATCTATCGTTATTTTGACAGCAAAGAAACACTCG | 750 |
| 751 | TTAACGTACTGTTTCAAGAAAGCATCCAGCGATTTACGGAAAAACTGAAG | 800 |
| 801 | CAAGACGTTTCAGAATTGCCTGTCAGAGAAGGCTTTCACCACGTATTTTG | 850 |
| 851 | CTGTCTCGTTCAGTTTACGAAAGAGAGCGACTATGCGCTTTTTTTCTTG | 900 |
| 901 | AAACCAAAAAAGACGCTCATTACTTAAATCATACAAGCAAAAAAATGATA | 950 |
| 951 | GAAAATCTGACTCAAATGCTTGATGACTATTTTAATAAGGGAAAAGCGGA | 1000 |
| 1001 | AGGCGTGATTCGCAGCCTGCCCTCTAATGTGTTAATTGCGATTGTATTAG | 1050 |
| 1051 | GGGCGTTTCTCAAGATATATCAGCTCGTTCAAACAGGTGATATAGAGATG | 1100 |
| 1101 | GACACTGATTTAATTACTGAATTGGAACAATGCTGCTGGGACGCCATTAA | 1150 |
| 1151 | GCTTCATTCATCACAAAAATAGGAAAGGGAGATGTTAATGAAACAGGCAA | 200 |
| 1201 | GCGCAATACCTCAGCCCAAAACATACGGACCTTTAAAAAATCTTCCGCAT | 1250 |
| 1251 | CTGGAAAAAGAACAGCTTTCTCAATCCTTATGGCGGATAGCTGATGAATT | 1300 |
| 1301 | GGGACCGATTTTCCGTTTTGATTTTCCGGGAGTATCCAGTGTTTTTGTGT | 1350 |
| 1351 | CCGGCCACAATCTTGTGGCTGAAGTGTGTGATGAAAAACGCTTTGACAAG | 1400 |
| 1401 | AACCTTGGCAAAGGCTTGCAAAAGGTGCGTGAGTTCGGGGGAGATGGCTT | 1450 |

-continued

| cypB-bs168-inter-1-pUC19c |
|---|

```
1451  ATTTACAAGCTGGACGCACGAACCGAACTGGCAAAAAGCCCACCGCATTT  1500
1501  TGCTGCCGAGTTTTAGTCAAAAAGCGATGAAAGGCTATCATTCTATGATG  1550
1551  CTGGATATCGCAACCCAGCTGATTCAAAAGTGGAGCCGGTTAAACCCTAA  1600
1601  TGAAGAAATTGATGTAGCGGACGATATGACACGTCTGACGCTTGATACGA  1650
1651  TTGGGTTATGCGGGTTTAACTATCGATTCAACAGCTTTTACCGTGATTCA  1700
1701  CAGCATCCGTTTATCACCAGTATGCTCCGTGCCTTAAAAGAGGCGATGAA  1750
1751  TCAATCGAAAAGACTGGGCCTGCAAGATAAAATGATGGTGAAAACGAAGC  1800
1801  TGCAGTTCCAAAAGGATATAGAAGTCATGAACTCCCTGGTTGATAGAATG  1850
1851  ATAGCGGAGCGAAAGGCGAATCCGGATGAAAACATTAAGGATCTCTTGTC  1900
1901  TCTCATGCTTTATGCCAAAGATCCAGTAACGGGTGAAACGCTGGATGACG  1950
1951  AAAACATTCGATACCAAATCATCACATTTTTAATTGCTGGACATGAGACA  2000
2001  ACAAGCGGGTTGCTATCCTTTGCGATTTATTGTCTGCTTACACATCCGGA  2050
2051  AAAACTGAAAAAAGCTCAGGAGGAAGCGGATCGCGTGTTAACGGATGACA  2100
2101  CGCCTGAATATAAACAAATCCAGCAGCTCAAATACATTCGGATGGTTTTA  2150
2151  AATGAAACCCTCAGACTGTATCCAACAGCTCCGGCTTTTTCTCTATATGC  2200
2201  GAAGGAGGATACTGTTCTAGGCGGGGAATATCCGATCAGCAAAGGGCAGC  2250
2251  CAGTCACTGTTTTAATTCCAAAACTGCACCGGGATCAAAACGCTTGGGGA  2300
2301  CCGGATGCGGAAGATTTCCGTCCGGAACGGTTTGAGGATCCTTCAAGTAT  2350
2351  CCCTCACCATGCGTATAAGCCGTTTGGAAACGGACAGCGCGCTTGTATTG  2400
2401  GCATGCAGTTTGCTCTTCAAGAAGCGACAATGGTTCTCGGTCTTGTATTA  2450
2451  AAGCATTTTGAATTGATAAACCATACTGGCTACGAACTAAAAATCAAAGA  2500
2501  AGCATTAACGATCAAGCCGGATGATTTTAAAATTACTGTGAAACCGCGAA  2550
2551  AAACAGCGGCAATCAATGTACAGAGAAAAGAACAGGCAGACATCAAAGCA  2600
2601  GAAACAAAGCCAAAAGAAACCAAACCTAAACACGGCACACCTTTACTTGT  2650
2651  TCTTTTTGGTTCAAATCTTGGGACAGCTGAGGGAATAGCCGGTGAACTGG  2700
2701  CTGCTCAAGGCCGCCAGATGGGCTTTACAGCTGAAACGGCTCCGCTTGAT  2750
2751  GATTATATCGGCAAGCTCCCTGAAGAAGGGGCAGTCGTCATTGTAACGGC  2800
2801  TTCTTATAATGGGGCGCCGCCTGATAATGCTGCCGGATTTGTAGAGTGGC  2850
2851  TGAAAGAGCTTGAGGAAGGCCAATTGAAAGGTGTTTCCTATGCGGTATTC  2900
2901  GGCTGCGGAAACCGGAGCTGGGCCAGCACGTATCAGCGGATTCCCCGCCT  2950
2951  GATTGATGACATGATGAAAGCAAAGGGGCATCGCGTTTAACAGCGATTG  3000
3001  GGGAAGGTGACGCCGCCGATGATTTTGAAAGCCACCGCGAGTCTTGGGAA  3050
3051  AACCGCTTCTGGAAGGAAACGATGGACGCATTTGATATTAACGAAATAGC  3100
3101  CCAGAAAGAAGACAGGCCTTCATTATCGATTACTTTTCTCAGTGAAGCGA  3150
3151  CGGAAACGCCGGTTGCTAAAGCATATGGCGCGTTTGAAGGGATTGTGTTA  3200
3201  GAGAATCGAGAACTCCAGACAGCTGCCAGCACGCGTTCAACCCGCCATAT  3250
3251  TGAATTGGAAATTCCGGCTGGTAAAACATATAAAGAAGGCGATCATATCG  3300
3301  GAATCCTGCCAAAGAACAGCAGGGAGCTTGTTCAGCGGGTTCTCAGCCGA  3350
3351  TTCGGTTTGCAGTCCAATCATGTGATAAAAGTAAGCGGAAGCGCTCATAT  3400
```

-continued

| cypB-bs168-inter-1-pUC19c |
|---|

| 3401 | GGCTCATCTGCCGATGGATCGGCCAATCAAAGTAGTGGATTTATTGTCGT | 3450 |
| 3451 | CCTATGTAGAGCTGCAGGAACCGGCATCAAGGCTTCAGCTTCGGGAGCTG | 3500 |
| 3501 | GCCTCTTATACAGTTTGTCCGCCGCATCAAAAAGAGCTGGAACAGCTCGT | 3550 |
| 3551 | TTCAGATGATGGCATTTACAAAGAGCAGGTACTTGCAAAACGTCTTACCA | 3600 |
| 3601 | TGCTTGATTTTTTAGAGGATTATCCTGCTTGCGAAATGCCGTTTGAACGG | 3650 |
| 3651 | TTTTTAGCACTTTTGCCATCACTAAAACCGAGATACTATTCCATTTCAAG | 3700 |
| 3701 | CTCACCGAAAGTTCATGCAAATATCGTGAGCATGACGGTAGGAGTTGTGA | 3750 |
| 3751 | AAGCCTCAGCATGGAGCGGCCGAGGTGAATACCGGGGTGTCGCCTCTAAT | 3800 |
| 3801 | TATTTAGCAGAATTGAATACAGGTGATGCAGCAGCTTGCTTCATTCGTAC | 3850 |
| 3851 | GCCGCAGTCCGGATTTCAGATGCCGAATGATCCTGAAACGCCTATGATTA | 3900 |
| 3901 | TGGTCGGGCCGGGCACAGGAATTGCGCCATTCAGAGGCTTTATTCAGGCA | 3950 |
| 3951 | AGATCGGTTTTGAAGAAGGAAGGAAGCACCCTTGGTGAAGCACTTTTATA | 4000 |
| 4001 | CTTCGGCTGCCGCCGCCCGGACCATGACGACCTTTACAGAGAAGAGCTGG | 4050 |
| 4051 | ATCAAGCGGAACAGGACGGTTTGGTCACAATCCGCCGATGCTACTCGCGC | 4100 |
| 4101 | GTCGAAAACGAACCAAAAGGATATGTCCAGCACTTGCTCAAGCAAGATAC | 4150 |
| 4151 | GCAGAAATTGATGACACTCATTGAAAAGGGGCTCATATTTACGTATGCG | 4200 |
| 4201 | GTGATGGATCGCAAATGGCTCCTGATGTAGAGAGAACTTTGCGATTGGCA | 4250 |
| 4251 | TATGAAGCTGAAAAAGCAGCAAGTCAGGAAGAATCAGCTGTATGGCTGCA | 4300 |
| 4301 | AAAGCTGCAAGATCAAAGACGTTATGTGAAAGACGTTTGGACAGGAATGT | 4350 |
| 4351 | AAAATATAAAATCCCGCCAATCTGATTGGCGGGATTGCTTTGCATATGAG | 4400 |
| 4401 | AAAACCGGCACGATAATGAAATCTACTGAAAAGGATGTTATAGGGAGTAT | 4450 |
| 4451 | CGCGCCGGCCTTATTATTCATATCGGCATGCAGAGGCAAAAGTTTAGTTC | 4500 |
| 4501 | TTTTTACCTTGTTTTTAAAAATAAATAGTCTGAAAGTCTTGTTTTTGATT | 4550 |
| 4551 | TTCGACTCAGGCTTTTGGCATTTTGTTCTTTCTTATTCCTTAAGATCAGT | 4600 |
| 4601 | CATCTGTTGAAGATTGATGCTTGAATTGCTGTTCCACATGCTTACGGTAA | 4650 |
| 4651 | TGAAAGTCATGAATCAGCCGAATGGTCGGCCTGATTAACAGCAGCAAACT | 4700 |
| 4701 | TCCGATCGCAAACAGCCATATCCCTGCCGACATTAACCGGTCATAAAAAA | 4750 |
| 4751 | AGAAAAAACTTCCAACGAGAAACATAGCACCGATGATAAAATCGTTTACT | 4800 |
| 4801 | GTATAAAGAACCTTATATCGTTTTTTGAAAAAAAGCTCATATCGTTTCAA | 4850 |
| 4851 | CTCTTTTTGGATGTCATGTTCTTCATTTCCTTTCATTATCATCCCTCCAT | 4900 |
| 4901 | TCAATTTTGGCTTACCCTTACGTAAACGGCATGTAAACATAAGGGCTGCC | 4950 |
| 4951 | TTGCTGAAAGAAGACATAATCAACGATCAGAAACTAAAGTAAAAAAGTGA | 5000 |
| 5001 | TCTGTATAGGATCTCTTTTTTACGATTTCATCGCCTGAACAATAAGAGCA | 5050 |
| 5051 | GTCAAAGTTTTTGCCCCTTTAGGAACCAAGTGAACACCATCAGGGGTAAA | 5100 |
| 5101 | ATATTCCGGATGCTGAAGAGCTTCTGTATGCCAGTCAACTAACGTAACAT | 5150 |
| 5151 | TTTGATGTGCGTGGGCCTGTTGCTGCAAAGATTCATTTACCTTGCTTTCC | 5200 |
| 5201 | CATTGGCGGGAACCCGTGTATTGACAAGATAAATATGAGCTTTTGAGAA | 5250 |
| 5251 | AGATTGAAGCAGTTGTTCGATTTGGCTGTTTGTAAAATAGCCATTGGTTC | 5300 |

-continued

| cypB-bs168-inter-1-pUC19c |
|---|
| 5301 CAAGCTCAATGATGACAGCCTTGTTCGGCTGATTAAAAGACTTGTATTCC 5350 |
| 5351 CTGCGGTGTGAAATACCGCACAGATGCGTAAGGAGAAAATACCGCATCAG 5400 |
| 5401 GCGCCATTCGCCATTCAGGCTGCGCAACTGTTGGGAAGGGCGATCGGTGC 5450 |
| 5451 GGGCCTCTTCGCTATTACGCCAGCTGGCGAAAGGGGGATGTGCTGCAAGG 5500 |
| 5501 CGATTAAGTTGGGTAACGCCAGGGTTTTCCCAGTCACGACGTTGTAAAAC 5550 |
| 5551 GACGGCCAGTGAATTCGAGCTCGGTACCCGGGGATCCTCTAGAGTCGACC 5600 |
| 5601 TGCAGGCATGCAAGCTTGGCGTAATCATGGTCATAGCTGTTTCCTGTGTG 5650 |
| 5651 AAATTGTTATCCGCTCACAATTCCACACAACATACGAGCCGGAAGCATAA 5700 |
| 5701 AGTGTAAAGCCTGGGGTGCCTAATGAGTGAGCTAACTCACATTAATTGCG 5750 |
| 5751 TTGCGCTCACTGCCCGCTTTCCAGTCGGGAAACCTGTCGTGCCAGCTGCA 5800 |
| 5801 TTAATGAATCGGCCAACGCGCGGGGAGAGGCGGTTTGCGTATTGGGCGCT 5850 |
| 5851 CTTCCGCTTCCTCGCTCACTGACTCGCTGCGCTCGGTCGTTCGGCTGCGG 5900 |
| 5901 CGAGCGGTATCAGCTCACTCAAAGGCGGTAATACGGTTATCCACAGAATC 5950 |
| 5951 AGGGGATAACGCAGGAAAGAACATGTGAGCAAAAGGCCAGCAAAAGGCCA 6000 |
| 6001 GGAACCGTAAAAAGGCCGCGTTGCTGGCGTTTTTCCATAGGCTCCGCCCC 6050 |
| 6051 CCTGACGAGCATCACAAAAATCGACGCTCAAGTCAGAGGTGGCGAAACCC 6100 |
| 6101 GACAGGACTATAAAGATACCAGGCGTTTCCCCCTGGAAGCTCCCTCGTGC 6150 |
| 6151 GCTCTCCTGTTCCGACCCTGCCGCTTACCGGATACCTGTCCGCCTTTCTC 6200 |
| 6201 CCTTCGGGAAGCGTGGCGCTTTCTCATAGCTCACGCTGTAGGTATCTCAG 6250 |
| 6251 TTCGGTGTAGGTCGTTCGCTCCAAGCTGGGCTGTGTGCACGAACCCCCCG 6300 |
| 6301 TTCAGCCCGACCGCTGCGCCTTATCCGGTAACTATCGTCTTGAGTCCAAC 6350 |
| 6351 CCGGTAAGACACGACTTATCGCCACTGGCAGCAGCCACTGGTAACAGGAT 6400 |
| 6401 TAGCAGAGCGAGGTATGTAGGCGGTGCTACAGAGTTCTTGAAGTGGTGGC 6450 |
| 6451 CTAACTACGGCTACACTAGAAGAACAGTATTTGGTATCTGCGCTCTGCTG 6500 |
| 6501 AAGCCAGTTACCTTCGGAAAAAGAGTTGGTAGCTCTTGATCCGGCAAACA 6550 |
| 6551 AACCACCGCTGGTAGCGGTGGTTTTTTTGTTTGCAAGCAGCAGATTACGC 6600 |
| 6601 GCAGAAAAAAAGGATCTCAAGAAGATCCTTTGATCTTTTCTACGGGGTCT 6650 |
| 6651 GACGCTCAGTGGAACGAAAACTCACGTTAAGGGATTTTGGTCATGAGATT 6700 |
| 6701 ATCAAAAAGGATCTTCACCTAGATCCTTTTAAATTAAAAATGAAGTTTTA 6750 |
| 6751 AATCAATCTAAAGTATATATGAGTAAACTTGGTCTGACAGTTACCAATGC 6800 |
| 6801 TTAATCAGTGAGGCACCTATCTCAGCGATCTGTCTATTTCGTTCATCCAT 6850 |
| 6851 AGTTGCCTGACTCCCCGTCGTGTAGATAACTACGATACGGGAGGGCTTAC 6900 |
| 6901 CATCTGGCCCCAGTGCTGCAATGATACCGCGAGACCCACGCTCACCGGCT 6950 |
| 6951 CCAGATTTATCAGCAATAAACCAGCCAGCCGGAAGGGCCGAGCGCAGAAG 7000 |
| 7001 TGGTCCTGCAACTTTATCCGCCTCCATCCAGTCTATTAATTGTTGCCGGG 7050 |
| 7051 AAGCTAGAGTAAGTAGTTCGCCAGTTAATAGTTTGCGCAACGTTGTTGCC 7100 |
| 7101 ATTGCTACAGGCATCGTGGTGTCACGCTCGTCGTTTGGTATGGCTTCATT 7150 |
| 7151 CAGCTCCGGTTCCCAACGATCAAGGCGAGTTACATGATCCCCCATGTTGT 7200 |
| 7201 GCAAAAAAGCGGTTAGCTCCTTCGGTCCTCCGATCGTTGTCAGAAGTAAG 7250 |

| cypB-bs168-inter-1-pUC19c | |
|---|---|
| 7251 TTGGCCGCAGTGTTATCACTCATGGTTATGGCAGCACTGCATAATTCTCT | 7300 |
| 7301 TACTGTCATGCCATCCGTAAGATGCTTTTCTGTGACTGGTGAGTACTCAA | 7350 |
| 7351 CCAAGTCATTCTGAGAATAGTGTATGCGGCGACCGAGTTGCTCTTGCCCG | 7400 |
| 7401 GCGTCAATACGGGATAATACCGCGCCACATAGCAGAACTTTAAAAGTGCT | 7450 |
| 7451 CATCATTGGAAAACGTTCTTCGGGGCGAAAACTCTCAAGGATCTTACCGC | 7500 |
| 7501 TGTTGAGATCCAGTTCGATGTAACCCACTCGTGCACCCAACTGATCTTCA | 7550 |
| 7551 GCATCTTTTACTTTCACCAGCGTTTCTGGGTGAGCAAAAACAGGAAGGCA | 7600 |
| 7601 AAATGCCGCAAAAAAGGGAATAAGGGCGACACGGAAATGTTGAATACTCA | 7650 |
| 7651 TACTCTTCCTTTTTCAATATTATTGAAGCATTTATCAGGGTTATTGTCTC | 7700 |
| 7701 ATGAGCGGATACATATTTGAATGTATTTAGAAAAATAAACAAATAGGGGT | 7750 |
| 7751 TCCGCGCACATTTCCCCGAAAAGTGCCACCTGACGTCTAAGAAACCATTA | 7800 |
| 7801 TTATCATGACATTAACCTATAAAAATAGGCGTATCACGAGGCCCTTTCGT | 7850 |
| 7851 C | 7851 |

The plasmid cypB-bs168-inter-1-pUC19c was subsequently amplified with primers 55791 (5'-CGCAACTGTCCATACTCTgAATATAAAATCCCGCCAATCT-3') and 55792 (5'-GAACATCGTCAAAAAACCcTAACATCTCCCTTTCCTATTTTT-3') to produce a cypB knockout vector. The cypB knockout vector was annealed to a PCR product obtained from amplifying upp-kan from plasmid upp-kan-pUC19, for example, using primers 50374 (5'-GGGTTTTTTGACGATGTTcTTGAAACTCAATGTCTTTTTTT-3') and 50371 (5'-CAGAGTATGGACAGTTGCgGATGTACTTCAGAAAAGATTAGATG-3'). The annealed mixture was transformed into cells (e.g., AbleK cells) to produce the plasmid cypB-bs168-precursor-pUC19c, the nucleotide sequence of which is shown below:

| cypB-bs168-precursor-pUC19c | |
|---|---|
| 1 TCGCGCGTTTCGGTGATGACGGTGAAAACCTCTGACACATGCAGCTCCCG | 50 |
| 51 GAGACGGTCACAGCTTGTCTGTAAGCGGATGCCGGGAGCAGACAAGCCCG | 100 |
| 101 TCAGGGCGCGTCAGCGGGTGTTGGCGGGTGTCGGGGCTGGCTTAACTATG | 150 |
| 151 CGGCATCAGAGCAGATTGTACTGAGAGTGCACCATATGCTTGCATTAAGA | 200 |
| 201 GAAATTTACAGGGTGCTTCAAATTGACGGCCGGTTTTATATCAGTATTGA | 250 |
| 251 CACAAATACCGGTGAAAAAGAGAAAACGTATATTCAACTGCTGAAAGACC | 300 |
| 301 AGCATTTCAGGGATCTTTCTGTTATCAGGCGTGCTTCCTGTCTATGTATT | 350 |
| 351 GTGGCTGTTAAATAAAAAATTTCTCGGGAAATATATCCAAGATCCTCGTA | 400 |
| 401 TTAGGATTTGGGTATATTTTCTTAATTTTTATTTTTGCATATACTTTA | 450 |
| 451 TATTAAAAAAAGTTTTTTCATATAAACTTATAACAGAAGAAAGAACAAA | 500 |
| 501 GAGGTGATATCAGACAGGGCAGACATTCTTTGTGAACAAAAGGAATGAAT | 550 |
| 551 ATTCATTCCGTAAACGAATCGGAGGTTGTCAGATTACATGATATCCGCAT | 600 |
| 601 CCAGCAGTAAATACGACATGATTATGAAAGCGTCAGTCTCACTTTTTACG | 650 |
| 651 GAAAGGGGTTTTGACGCTACCACTATTCCTATGATAGCTGAACGTGCTCA | 700 |
| 701 TGTAGGGACAGGAACGATCTATCGTTATTTTGACAGCAAAGAAACACTCG | 750 |
| 751 TTAACGTACTGTTTCAAGAAAGCATCCAGCGATTTACGGAAAAACTGAAG | 800 |
| 801 CAAGACGTTTCAGAATTGCCTGTCAGAGAAGGCTTTCACCACGTATTTTG | 850 |
| 851 CTGTCTCGTTCAGTTTACGAAAGAGAGCGACTATGCGCTTTTTTTTCTTG | 900 |

-continued

| cypB-bs168-precursor-pUC19c | | |
|---|---|---|
| 901 | AAACCAAAAAAGACGCTCATTACTTAAATCATACAAGCAAAAAAATGATA | 950 |
| 951 | GAAAATCTGACTCAAATGCTTGATGACTATTTTAATAAGGGAAAAGCGGA | 1000 |
| 1001 | AGGCGTGATTCGCAGCCTGCCCTCTAATGTGTTAATTGCGATTGTATTAG | 1050 |
| 1051 | GGGCGTTTCTCAAGATATATCAGCTCGTTCAAACAGGTGATATAGAGATG | 1100 |
| 1101 | GACACTGATTTAATTACTGAATTGGAACAATGCTGCTGGGACGCCATTAA | 1150 |
| 1151 | GCTTCATTCATCACAAAAATAGGAAAGGGAGATGTTAGGGTTTTTTGACG | 1200 |
| 1201 | ATGTTCTTGAAACTCAATGTCTTTTTTTGTAGAATCAATAGAAGTGTGTA | 1250 |
| 1251 | ATTGTTGATGGGACAATAAAAAAGGAGCTGAAACACAGTATGGGAAAGGT | 1300 |
| 1301 | TTATGTATTTGATCATCCTTTAATTCAGCACAAGCTGACATATATACGGA | 1350 |
| 1351 | ATGAAAATACAGGTACGAAGGATTTTAGAGAGTTAGTAGATGAAGTGGCT | 1400 |
| 1401 | ACACTCATGGCATTTGAAATTACCCGCGATCTTCCTCTGGAAGAAGTGGA | 1450 |
| 1451 | TATCAATACACCGGTTCAGGCTGCGAAATCGAAAGTCATCTCAGGGAAAA | 1500 |
| 1501 | AACTCGGAGTGGTTCCTATCCTCAGAGCAGGATTGGGAATGGTTGACGGC | 1550 |
| 1551 | ATTTTAAAGCTGATTCCTGCGGCAAAAGTGGGACATGTCGGCCTTTACCG | 1600 |
| 1601 | TGATCCAGAAACCTTAAAACCCGTGGAATACTATGTCAAGCTTCCTTCTG | 1650 |
| 1651 | ATGTGGAAGAGCGTGAATTCATCGTGGTTGACCCGATGCTCGCTACAGGC | 1700 |
| 1701 | GGTTCCGCAGTTGAAGCCATTCACAGCCTTAAAAAACGCGGTGCGAAAAA | 1750 |
| 1751 | TATCCGTTTCATGTGTCTTGTAGCAGCGCCGGAGGGTGTGGAAGAATTGC | 1800 |
| 1801 | AGAAGCATCATTCGGACGTTGATATTTACATTGCGGCGCTAGATGAAAAA | 1850 |
| 1851 | TTAAATGAAAAAGGATATATTGTTCCAGGTCTCGGAGATGCGGGTGACCG | 1900 |
| 1901 | CATGTTTGGAACAAAATAAAAAATGAAATCCCCAAAAGGGGGTTTCATTT | 1950 |
| 1951 | TTTTATCCAGTTTTTTGCTATTCGGTGAATCTGTATACAATTATAGGTGA | 2000 |
| 2001 | AAATGTGAACATTCTGGGATCCGATAAACCCAGCGAACCATTTGAGGTGA | 2050 |
| 2051 | TAGGTAAGATTATACCGAGGTATGAAAACGAGAATTGGACCTTTACAGAA | 2100 |
| 2101 | TTACTCTATGAAGCGCCATATTTAAAAAGCTACCAAGACGAAGAGGATGA | 2150 |
| 2151 | AGAGGATGAGGAGGCAGATTGCCTTGAATATATTGACAATACTGATAAGA | 2200 |
| 2201 | TAATATATCTTTTATATAGAAGATATCGCCGTATGTAAGGATTTCAGGGG | 2250 |
| 2251 | GCAAGGCATAGGCAGCGCGCTTATCAATATATCTATAGAATGGGCAAAGC | 2300 |
| 2301 | ATAAAAACTTGCATGGACTAATGCTTGAAACCCAGGACAATAACCTTATA | 2350 |
| 2351 | GCTTGTAAATTCTATCATAATTGTGGTTTCAAAATCGGCTCCGTCGATAC | 2400 |
| 2401 | TATGTTATACGCCAACTTTCAAAACAACTTTGAAAAAGCTGTTTTCTGGT | 2450 |
| 2451 | ATTTAAGGTTTTAGAATGCAAGGAACAGTGAATTGGAGTTCGTCTTGTTA | 2500 |
| 2501 | TAATTAGCTTCTTGGGGTATCTTTAAATACTGTAGAAAAGAGGAAGGAAA | 2550 |
| 2551 | TAATAAATGGCTAAAATGAGAATATCACCGGAATTGAAAAAACTGATCGA | 2600 |
| 2601 | AAAATACCGCTGCGTAAAAGATACGGAAGGAATGTCTCCTGCTAAGGTAT | 2650 |
| 2651 | ATAAGCTGGTGGGAGAAAATGAAAACCTATATTTAAAAATGACGGACAGC | 2700 |
| 2701 | CGGTATAAAGGGACCACCTATGATGTGGAACGGGAAAAGGACATGATGCT | 2750 |
| 2751 | ATGGCTGGAAGGAAAGCTGCCTGTTCCAAAGGTCCTGCACTTTGAACGGC | 2800 |

| cypB-bs168-precursor-pUC19c | | |
|---|---|---|
| 2801 | ATGATGGCTGGAGCAATCTGCTCATGAGTGAGGCCGATGGCGTCCTTTGC | 2850 |
| 2851 | TCGGAAGAGTATGAAGATGAACAAAGCCCTGAAAAGATTATCGAGCTGTA | 2900 |
| 2901 | TGCGGAGTGCATCAGGCTCTTTCACTCCATCGACATATCGGATTGTCCCT | 2950 |
| 2951 | ATACGAATAGCTTAGACAGCCGCTTAGCCGAATTGGATTACTTACTGAAT | 3000 |
| 3001 | AACGATCTGGCCGATGTGGATTGCGAAAACTGGGAAGAAGACACTCCATT | 3050 |
| 3051 | TAAAGATCCGCGCGAGCTGTATGATTTTTTAAAGACGGAAAAGCCCGAAG | 3100 |
| 3101 | AGGAACTTGTCTTTTCCCACGGCGACCTGGAGACAGCAACATCTTTGTG | 3150 |
| 3151 | AAAGATGGCAAAGTAAGTGGCTTTATTGATCTTGGGAGAAGCGGCAGGGC | 3200 |
| 3201 | GGACAAGTGGTATGACATTGCCTTCTGCGTCCGGTCGATCAGGGAGGATA | 3250 |
| 3251 | TCGGGAAGAACAGTATGTCGAGCTATTTTTTGACTTACTGGGGATCAAG | 3300 |
| 3301 | CCTGATTGGGAGAAAATAAAATATTATATTTTACTGGATGAATTGTTTTA | 3350 |
| 3351 | GTACCTAGATTTAGATGTCTAAAAAGCTTTAACTACAAGCTTTTTAGACA | 3400 |
| 3401 | TCTAATCTTTTCTGAAGTACATCCGCAACTGTCCATACTCTGAATATAAA | 3450 |
| 3451 | ATCCCGCCAATCTGATTGGCGGGATTGCTTTGCATATGAGAAAACCGGCA | 3500 |
| 3501 | CGATAATGAAATCTACTGAAAAGGATGTTATAGGGAGTATCGCGCCGGCC | 3550 |
| 3551 | TTATTATTCATATCGGCATGCAGAGGCAAAGTTTAGTTCTTTTTACCTT | 3600 |
| 3601 | GTTTTTAAAAATAAATAGTCTGAAAGTCTTGTTTTTGATTTTCGACTCAG | 3650 |
| 3651 | GCTTTTGGCATTTTGTTCTTTCTTATTCCTTAAGATCAGTCATCTGTTGA | 3700 |
| 3701 | AGATTGATGCTTGAATTGCTGTTCCACATGCTTACGGTAATGAAAGTCAT | 3750 |
| 3751 | GAATCAGCCGAATGGTCGGCCTGATTAACAGCAGCAAACTTCCGATCGCA | 3800 |
| 3801 | AACAGCCATATCCCTGCCGACATTAACCGGTCATAAAAAAGAAAAAACT | 3850 |
| 3851 | TCCAACGAGAAACATAGCACCGATGATAAAATCGTTTACTGTATAAAGAA | 3900 |
| 3901 | CCTTATATCGTTTTTTGAAAAAAAGCTCATATCGTTTCAACTCTTTTTGG | 3950 |
| 3951 | ATGTCATGTTCTTCATTTCCTTTCATTATCATCCCTCCATTCAATTTTGG | 4000 |
| 4001 | CTTACCCTTACGTAAACGGCATGTAAACATAAGGGCTGCCTTGCTGAAAG | 4050 |
| 4051 | AAGACATAATCAACGATCAGAAACTAAAGTAAAAAAGTGATCTGTATAGG | 4100 |
| 4101 | ATCTCTTTTTTACGATTTCATCGCCTGAACAATAAGAGCAGTCAAAGTTT | 4150 |
| 4151 | TTGCCCCTTTAGGAACCAAGTGAACACCATCAGGGGTAAAATATTCCGGA | 4200 |
| 4201 | TGCTGAAGAGCTTCTGTATGCCAGTCAACTAACGTAACATTTTGATGTGC | 4250 |
| 4251 | GTGGGCCTGTTGCTGCAAAGATTCATTTACCTTGCTTTCCCATTGGCGGG | 4300 |
| 4301 | GAACCCGTGTATTGACAAGATAAATATGAGCTTTTGAGAAAGATTGAAGC | 4350 |
| 4351 | AGTTGTTCGATTTGGCTGTTTGTAAAATAGCCATTGGTTCCAAGCTCAAT | 4400 |
| 4401 | GATGACAGCCTTGTTCGGCTGATTAAAAGACTTGTATTCCCTGCGGTGTG | 4450 |
| 4451 | AAATACCGCACAGATGCGTAAGGAGAAAATACCGCATCAGGCGCCATTCG | 4500 |
| 4501 | CCATTCAGGCTGCGCAACTGTTGGGAAGGGCGATCGGTGCGGGCCTCTTC | 4550 |
| 4551 | GCTATTACGCCAGCTGGCGAAAGGGGGATGTGCTGCAAGGCGATTAAGTT | 4600 |
| 4601 | GGGTAACGCCAGGGTTTTCCCAGTCACGACGTTGTAAAACGACGGCCAGT | 4650 |
| 4651 | GAATTCGAGCTCGGTACCCGGGGATCCTCTAGAGTCGACCTGCAGGCATG | 4700 |
| 4701 | CAAGCTTGGCGTAATCATGGTCATAGCTGTTTCCTGTGTGAAATTGTTAT | 4750 |

| cypB-bs168-precursor-pUC19c | | |
|---|---|---|
| 4751 | CCGCTCACAATTCCACACAACATACGAGCCGGAAGCATAAAGTGTAAAGC | 4800 |
| 4801 | CTGGGGTGCCTAATGAGTGAGCTAACTCACATTAATTGCGTTGCGCTCAC | 4850 |
| 4851 | TGCCCGCTTTCCAGTCGGGAAACCTGTCGTGCCAGCTGCATTAATGAATC | 4900 |
| 4901 | GGCCAACGCGCGGGAGAGGCGGTTTGCGTATTGGGCGCTCTTCCGCTTC | 4950 |
| 4951 | CTCGCTCACTGACTCGCTGCGCTCGGTCGTTCGGCTGCGGCGAGCGGTAT | 5000 |
| 5001 | CAGCTCACTCAAAGGCGGTAATACGGTTATCCACAGAATCAGGGGATAAC | 5050 |
| 5051 | GCAGGAAAGAACATGTGAGCAAAAGGCCAGCAAAAGGCCAGGAACCGTAA | 5100 |
| 5101 | AAAGGCCGCGTTGCTGGCGTTTTTCCATAGGCTCCGCCCCCTGACGAGC | 5150 |
| 5151 | ATCACAAAAATCGACGCTCAAGTCAGAGGTGGCGAAACCCGACAGGACTA | 5200 |
| 5201 | TAAAGATACCAGGCGTTTCCCCCTGGAAGCTCCCTCGTGCGCTCTCCTGT | 5250 |
| 5251 | TCCGACCCTGCCGCTTACCGGATACCTGTCCGCCTTTCTCCCTTCGGGAA | 5300 |
| 5301 | GCGTGGCGCTTTCTCATAGCTCACGCTGTAGGTATCTCAGTTCGGTGTAG | 5350 |
| 5351 | GTCGTTCGCTCCAAGCTGGGCTGTGTGCACGAACCCCCCGTTCAGCCCGA | 5400 |
| 5401 | CCGCTGCGCCTTATCCGGTAACTATCGTCTTGAGTCCAACCCGGTAAGAC | 5450 |
| 5451 | ACGACTTATCGCCACTGGCAGCAGCCACTGGTAACAGGATTAGCAGAGCG | 5500 |
| 5501 | AGGTATGTAGGCGGTGCTACAGAGTTCTTGAAGTGGTGGCCTAACTACGG | 5550 |
| 5551 | CTACACTAGAAGAACAGTATTTGGTATCTGCGCTCTGCTGAAGCCAGTTA | 5600 |
| 5601 | CCTTCGGAAAAAGAGTTGGTAGCTCTTGATCCGGCAAACAAACCACCGCT | 5650 |
| 5651 | GGTAGCGGTGGTTTTTTGTTTGCAAGCAGCAGATTACGCGCAGAAAAAA | 5700 |
| 5701 | AGGATCTCAAGAAGATCCTTTGATCTTTTCTACGGGGTCTGACGCTCAGT | 5750 |
| 5751 | GGAACGAAAACTCACGTTAAGGGATTTTGGTCATGAGATTATCAAAAAGG | 5800 |
| 5801 | ATCTTCACCTAGATCCTTTTAAATTAAAAATGAAGTTTTAAATCAATCTA | 5850 |
| 5851 | AAGTATATATGAGTAAACTTGGTCTGACAGTTACCAATGCTTAATCAGTG | 5900 |
| 5901 | AGGCACCTATCTCAGCGATCTGTCTATTTCGTTCATCCATAGTTGCCTGA | 5950 |
| 5951 | CTCCCCGTCGTGTAGATAACTACGATACGGGAGGGCTTACCATCTGGCCC | 6000 |
| 6001 | CAGTGCTGCAATGATACCGCGAGACCCACGCTCACCGGCTCCAGATTTAT | 6050 |
| 6051 | CAGCAATAAACCAGCCAGCCGGAAGGGCCGAGCGCAGAAGTGGTCCTGCA | 6100 |
| 6101 | ACTTTATCCGCCTCCATCCAGTCTATTAATTGTTGCCGGGAAGCTAGAGT | 6150 |
| 6151 | AAGTAGTTCGCCAGTTAATAGTTTGCGCAACGTTGTTGCCATTGCTACAG | 6200 |
| 6201 | GCATCGTGGTGTCACGCTCGTCGTTTGGTATGGCTTCATTCAGCTCCGGT | 6250 |
| 6251 | TCCCAACGATCAAGGCGAGTTACATGATCCCCCATGTTGTGCAAAAAAGC | 6300 |
| 6301 | GGTTAGCTCCTTCGGTCCTCCGATCGTTGTCAGAAGTAAGTTGGCCGCAG | 6350 |
| 6351 | TGTTATCACTCATGGTTATGGCAGCACTGCATAATTCTCTTACTGTCATG | 6400 |
| 6401 | CCATCCGTAAGATGCTTTTCTGTGACTGGTGAGTACTCAACCAAGTCATT | 6450 |
| 6451 | CTGAGAATAGTGTATGCGGCGACCGAGTTGCTCTTGCCCGGCGTCAATAC | 6500 |
| 6501 | GGGATAATACCGCGCCACATAGCAGAACTTTAAAAGTGCTCATCATTGGA | 6550 |
| 6551 | AAACGTTCTTCGGGGCGAAAACTCTCAAGGATCTTACCGCTGTTGAGATC | 6600 |
| 6601 | CAGTTCGATGTAACCCACTCGTGCACCCAACTGATCTTCAGCATCTTTTA | 6650 |

| cypB-bs168-precursor-pUC19c | |
|---|---|
| 6651 CTTTCACCAGCGTTTCTGGGTGAGCAAAAACAGGAAGGCAAAATGCCGCA | 6700 |
| 6701 AAAAAGGGAATAAGGGCGACACGGAAATGTTGAATACTCATACTCTTCCT | 6750 |
| 6751 TTTTCAATATTATTGAAGCATTTATCAGGGTTATTGTCTCATGAGCGGAT | 6800 |
| 6801 ACATATTTGAATGTATTTAGAAAAATAAACAAATAGGGGTTCCGCGCACA | 6850 |
| 6851 TTTCCCCGAAAAGTGCCACCTGACGTCTAAGAAACCATTATTATCATGAC | 6900 |
| 6901 ATTAACCTATAAAAATAGGCGTATCACGAGGCCCTTTCGTC | 6941 |

The plasmid cypB-bs168-precursor-pUC19c was used to transform 59196-A8 OKB105-sfp+, phe+, upp::spc, amyE: Psrf-comS-PgroEL-sfp-srfD, srf::psrf-FA-Glu, maf:psrf-FA-Glu, eps::psrf-FA-Glu, rapC::psrf-FA-Glu, yngF::psrf-FA-Glu, pps::CAM, lacA:xyIR-pxylA-comK-ermR, spoIIAC:ko, degU::ko. A resulting strain was named "strain 61000-A5."

Cultures of strain 61000-AS were inoculated (e.g., from glycerol scraping) into cell culture media (e.g., 10 mL S7(Phos7.5) media) and grown in shaking incubator for an appropriate period of time (e.g., 4 days). An aliquot of culture (e.g., 1 mL of culture) was then sampled for characterization and analysis, for example, by liquid chromatography-mass spectrometry (LC-MS). For example, an aliquot of culture was centrifuged at 13,500 RPM for 5 minutes and supernatant was filtered through 0.45 µM DURAPORE™ (polyvinylidene fluoride membrane filter) columns at 7000 g for 1 minute and filtrate was diluted 1:200 for LC-MS analysis.

Results and Discussion: Analysis of production of FA-Glu by strain 61000-A5 shows that strain 61000-A5 was able to produce FA-Glu with no additional hydroxyl groups. Such data was obtained using LC-MS analysis. In some embodiments, an acyl amino acid composition comprising substantially 100% FA-Glu with substantially no additional hydroxyl groups (except that in some embodiments, FA-Glu may comprise a β-hydroxyl group). This Example shows that inactivation of a gene encoding a fatty acid hydroxylase (e.g., cypB gene) reduced the level of modification (hydroxylation) of acyl amino acids, e.g., FA-Gly and FA-Glu, to very low-nearly undetectable-levels. Therefore, one aspect of the present disclosure encompasses the insight that acyl amino acid-producing cells with a modification that modulates hydroxylation of a fatty acid portion of an acyl amino acid (e.g., by inactivating one or more genes encoding a fatty acid hydroxylase such as, e.g., cypB gene) can be useful to production of surfactants and fatty acids for commercial purposes. The present disclosure provides, among others, insights that fatty acid hydroxylation by a cypB enzyme expressed by acyl amino acid-producing cells can be undesirable in certain circumstances where desirable surfactants and/or fatty acid do not comprise additional hydroxyl groups (except that in some embodiments, such desirable surfactants and/or fatty acid may have a β-hydroxyl), and that the presence of such hydroxylated products may lower the yield of the desired surfactants and/or fatty acid. The present inventors demonstrated that inactivation of a fatty acid hydroxylase (e.g., by inactivating a gene encoding cypB) in acyl amino acid-producing cells increased yield of the desired surfactant and/or fatty acids. Accordingly, one aspect of the present disclosure provides technologies for increasing yield of surfactants and/or fatty acids of interest (e.g., without ω-n hydroxyl groups, where n≥1).

Example 3: Production of Acyl Amino Acids Using a Microbial Catalyst (with or without a Modification that Modulates Hydroxylation of a Fatty Acid Portion of Acyl Amino Acids)

Surfactants such as acyl amino acids, e.g., capryloyl glycine, lauroyl glycinate, myristoyl glycinate, and cocoyl glycinate, are typically manufactured using hazardous chemical processes, such as chlorination of fatty acids (as described in U.S. Pat. No. 8,338,483). Disclosed herein are methods for producing acyl amino acid-based surfactants using a microbial catalysis. For example, in some embodiments, microbial cells (e.g., Bacillus subtilis) are cultured or grown in a culture medium containing a carbon source, such as, e.g., glucose, a fatty acid (which is selected to form a fatty acid portion of an acyl amino acid), and an amino acid (which is selected to form an amino acid portion of an acyl amino acid) in the presence of an enzyme that covalently links a fatty acid to an amino acid under conditions and for a time sufficient for an acyl amino acid position to be made. In some embodiments, glycine may be selected as an amino acid provided in a culture medium. Substrates are converted by microbial cells (e.g., Bacillus cells) into desired acyl amino acid surfactants depending on the selection of fatty acids and amino acid. By way of example only, lauroyl glycinate is produced when lauric acid and glycine are provided in a culture medium, in which microbial cells are culture or grown in the presence of an enzyme that covalently links a fatty acid to an amino acid under conditions and for a time sufficient for an acyl amino acid position to be made. In some embodiments, such microbial cells may be engineered to comprise modification that modulates hydroxylation of a fatty acid portion of an acyl amino acid (e.g., as described in Example 2).

In some embodiments, strains were inoculated (e.g., from glycerol scraping) into 10 mL cultures containing LB+Ery (LB media with erythromycin). Cultures were grown for ~20 hrs at 37° C. with 200 RPM agitation. 100 uL of this seed culture was then used to inoculate flasks containing 50 mL S7(Phos7.5)Gly+Ery. Cultures were grown as described herein for ~24 hrs before being split into 4×10 mL cultures. These split cultures were each supplemented with no fatty acid or a fatty acid as indicated: (a) no fatty acid, (b) octanoic acid (e.g., 5 µL 200 mM; diluted from 98% stock Sigma W279900), (c) lauric acid (e.g., 5 µL 200 mM; Sigma W261408 resuspended in 200 proof ethanol), or (d) myristic acid (e.g., 5 µL 200 mM; Sigma 70082 resuspended in 200 proof ethanol). Supplemented cultures were grown as above for ~6 hrs before a 0.5 mL sample removed and frozen at −20° C. Cultures were returned to an incubator. Cultures were sampled again as described above at ~24 hrs post-supplementation. Frozen samples were thawed and centrifuged at 13,500 RPM×5 min. 250 uL supernatant was filtered through 0.45 uM filter plate at 5000 g×10 min. Filtrate was diluted 1:20 for LCMS analysis.

Figure 3:
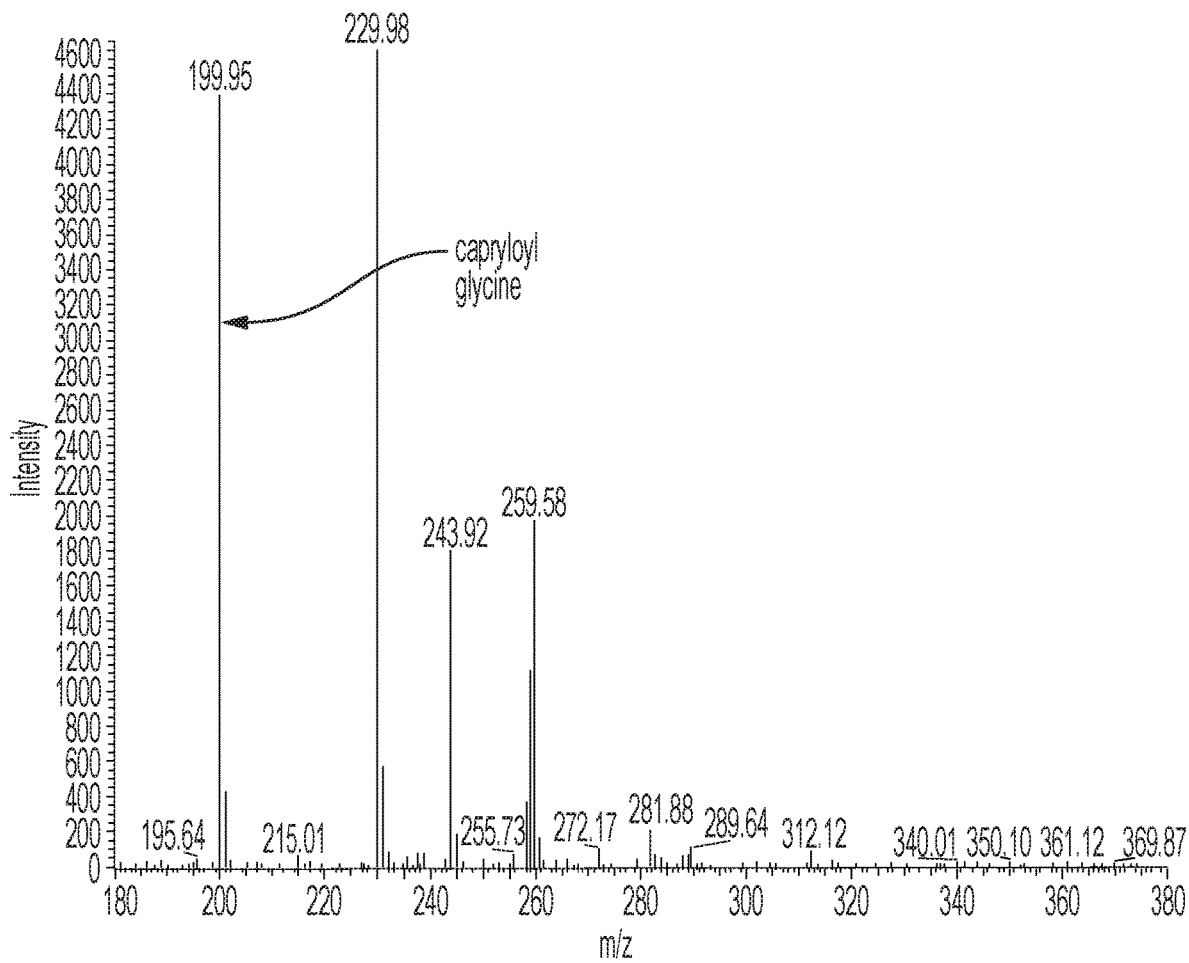
FIG. 3 depicts LC-MS analysis of an exemplary acyl acid composition produced by fermentation supplemented with glycine and caprylic acid.

Octanoic acid: Analysis of cultures supplemented with octanoic acid showed a unique peak at ~200 Da corresponding to C8-Glycine (FIG. 3). This peak eluted at about the same retention time as capryloyl glycine (Carbosynth FC15595). As discussed herein, the present disclosure recognizes that surfactants produced in *Bacillus* are often modified by hydroxylation. A peak corresponding to a higher molecular weight synthesis product with a mass of about 230 Dalton was also detected. It was contemplated that such a higher molecular weight synthesis product may be resulted from both hydroxylation and methylation of C8-glycine. See, e.g., Sun et al. Sci Total Environ (2018) 613-614: 54-61. Both peak signals were strongest in cultures collected at T=6 hr; and were weaker at 24 hours post-addition of substrates. Significantly, both peak signals remained strong, even after 24 hours of incubation in a strain in which a fatty acid hydroxylase is inactivated (e.g., as described in Example 1), e.g., by knocking out cypB gene, which indicates that cypB plays a role in hydroxylation of the C8-glycine, converting it into higher molecule weight modified (hydroxylated) forms. In some embodiments, production of acyl amino acid with one or more ω-n hydroxyl groups (where n ≥1) can be reduced or eliminated by deletion of one or more genes encoding a fatty acid hydroxylase, such as cypB. Other peak signals were observed with masses of 244, 259, and 272 Dalton.

Lauric acid: Analysis of cultures supplemented with lauric acid showed a small unique peak at ~272 Dalton, which is contemplated to be corresponding to C12-Glycine-OH. An additional unique peak at ~302 Da, which is contemplated to be corresponding to C12-Me-2(OH)-glycine, was stable over time. Other peak signals correspond to species with a mass of 316 Dalton.

Myristic acid: Analysis of the cultures supplemented with myristic acid supplemented showed a unique peak at ~330 Dalton, which is contemplated to be corresponding to C14-2(Me)-OH-glycine, was stable over time. Other peak signals correspond to species with a mass of 344, 360 and 374 Dalton.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

LISTING OF CERTAIN SEQUENCES

>CAB12544.1-CYP102A2 Bifunctional P-450/NADPH-P450 Reductase 1 [*Bacillus subtilis* Subsp. *Subtilis* Str. 168]

```
                                              (SEQ ID NO: 1)
MKETSPIPQPKTFGPLGNLPLIDKDKPTLSLIKLAEEQGPIFQIHTPAG

TTIVVSGHELVKEVCDEEREDKSIEGALEKVRAFSGDGLFTSWTHEPNW

RKAHNILMPTFSQRAMKDYHEKMVDIAVQLIQKWARLNPNEAVDVPGDM

TRLTLDTIGLCGENYRFNSYYRETPHPFINSMVRALDEAMHQMQRLDVQ

DKLMVRTKRQFRYDIQTMFSLVDSIIAERRANGDQDEKDLLARMLNVED

PETGEKLDDENIRFQIITFLIAGHETTSGLLSFATYFLLKHPDKLKKAY

EEVDRVLTDAAPTYKQVLELTYIRMILNESLRLWPTAPAFSLYPKEDTV

IGGKFPITTNDRISVLIPQLHRDRDAWGKDAEEFRPERFEHQDQVPHHA

YKPFGNGQRACIGMQFALHEATLVLGMILKYFTLIDHENYELDIKQTLT

LKPGDFHISVQSRHQEAIHADVQAAEKAAPDEQKEKTEAKGASVIGLNN

RPLLVLYGSDTGTAEGVARELADTASLHGVRTKTAPLNDRIGKLPKEGA

VVIVTSSYNGKPPSNAGQFVQWLQEIKPGELEGVHYAVFGCGDHNWAST
```

YQYVPRFIDEQLAEKGATRFSARGEGDVSGDFEGQLDEWKKSMWADAIK

AFGLELNENADKERSTLSLQFVRGLGESPLARSYEASHASIAENRELQS

ADSDRSTRHIEIALPPDVEYQEGDHLGVLPKNSQTNVSRILHRFGLKGT

DQVTLSASGRSAGHLPLGRPVSLHDLLSYSVEVQEAATRAQIRELASFT

VCPPHRRELEELSAEGVYQEQILKKRISMLDLLEKYEACDMPFERFLEL

LRPLKPRYYSISSSPRVNPRQASITVGVVRGPAWSGRGEYRGVASNDLA

ERQAGDDVVMFIRTPESRFQLPKDPETPIIMVGPGTGVAPFRGFLQARD

VLKREGKTLGEAHLYFGCRNDRDFIYRDELERFEKDGIVTVHTAFSRKE

GMPKTYVQHLMADQADTLISILDRGGRLYVCGDGSKMAPDVEAALQKAY

QAVHGTGEQEAQNWLRHLQDTGMYAKDVWAGI

>CAB14658.1-CYP102A3 Cytochrome P450 CYP102A3 [*Bacillus subtilis* Subsp. *Subtilis* Str. 168]

(SEQ ID NO: 2)
MKQASAIPQPKTYGPLKNLPHLEKEQLSQSLWRIADELGPIFRFDFPGV

SSVFVSGHNLVAEVCDEKREDKNLGKGLQKVREFGGDGLFTSWTHEPNW

QKAHRILLPSFSQKAMKGYHSMMLDIATQLIQKWSRLNPNEEIDVADDM

TRLTLDTIGLCGENYRENSFYRDSQHPFITSMLRALKEAMNQSKRLGLQ

DKMMVKTKLQFQKDIEVMNSLVDRMIAERKANPDENIKDLLSLMLYAKD

PVTGETLDDENIRYQIITFLIAGHETTSGLLSFAIYCLLTHPEKLKKAQ

EEADRVLTDDTPEYKQIQQLKYIRMVLNETLRLYPTAPAFSLYAKEDTV

LGGEYPISKGQPVTVLIPKLHRDQNAWGPDAEDFRPERFEDPSSIPHHA

YKPFGNGQRACIGMQFALQEATMVLGLVLKHFELINHTGYELKIKEALT

IKPDDFKITVKPRKTAAINVQRKEQADIKAETKPKETKPKHGTPLLVLF

GSNLGTAEGIAGELAAQGRQMGFTAETAPLDDYIGKLPEEGAVVIVTAS

YNGAPPDNAAGFVEWLKELEEGQLKGVSYAVFGCGNRSWASTYQRIPRL

IDDMMKAKGASRLTAIGEGDAADDFESHRESWENRFWKETMDAFDINEI

AQKEDRPSLSITFLSEATETPVAKAYGAFEGIVLENRELQTAASTRSTR

HIELEIPAGKTYKEGDHIGILPKNSRELVQRVLSRFGLQSNHVIKVSGS

AHMAHLPMDRPIKVVDLLSSYVELQEPASRLQLRELASYTVCPPHQKEL

EQLVSDDGIYKEQVLAKRLTMLDFLEDYPACEMPFERFLALLPSLKPRY

YSISSSPKVHANIVSMTVGVVKASAWSGRGEYRGVASNYLAELNTGDAA

ACFIRTPQSGFQMPNDPETPMIMVGPGTGIAPFRGFIQARSVLKKEGST

LGEALLYFGCRRPDHDDLYREELDQAEQDGLVTIRRCYSRVENEPKGYV

QHLLKQDTQKLMTLIEKGAHIYVCGDGSQMAPDVERTLRLAYEAEKAAS

QEESAVWLQKLQDQRRYVKDVWTGM

>CAB14997.1-CYP107H1 Cytochrome P450 for Pimelic Acid Formation for Biotin Biosynthesis [*Bacillus subtilis* Subsp. *Subtilis* Str. 168]

(SEQ ID NO: 3)
MTIASSTASSEFLKNPYSFYDTLRAVHPIYKGSFLKYPGWYVTGYEETA

AILKDARFKVRTPLPESSTKYQDLSHVQNQMMLFQNQPDHRRLRTLASG

AFTPRTTESYQPYIIETVHHLLDQVQGKKKMEVISDFAFPLASFVIANI

IGVPEEDREQLKEWAASLIQTIDFTRSRKALTEGNIMAVQAMAYFKELI

QKRKRHPQQDMISMLLKGREKDKLTEEEAASTCILLAIAGHETTVNLIS

NSVLCLLQHPEQLLKLRENPDLIGTAVEECLRYESPTQMTARVASEDID

ICGVTIRQGEQVYLLLGAANRDPSIFTNPDVFDITRSPNPHLSFGHGHH

VCLGSSLARLEAQIAINTLLQRMPSLNLADFEWRYRPLFGFRALEELPV

TFE

>CAB14615.1-CYP107J1 Cytochrome P450 [*Bacillus subtilis* Subsp. *Subtilis* Str. 168]

(SEQ ID NO: 4)
MSSKEKKSVTILTESQLSSRAFKDEAYEFYKELRKSQALYPLSLGALGK

GWLISRYDDAIHLLKNEKLKKNYENVFTAKEKRPALLKNEETLTKHMLN

SDPPDHNRLRTLVQKAFTHRMILQLEDKIQHIADSLLDKVQPNKFMNLV

DDYAFPLPIIVISEMLGIPLEDRQKFRVWSQAIIDESDAPERLQENDHL

LGEFVEYLESLVRKKRREPAGDLISALIQAESEGTQLSTEELYSMIMLL

IVAGHETTVNLITNMTYALMCHHDQLEKLRQQPDLMNSAIEEALRFHSP

VELTTIRWTAEPFILHGQEIKRKDVIIISLASANRDEKIFPNADIFDIE

RKNNRHIAFGHGNHFCLGAQLARLEAKIAISTLLRRCPNIQLKGEKKQM

KWKGNFLMRALEELPISF

>ABQ22962.1-CYP107K1 Cytochrome P450 [*Bacillus subtilis* Subsp. *Subtilis* Str. 168]

(SEQ ID NO: 5)
MQMEKLMFHPHGKEFHHNPFSVLGRFREEEPIHRFELKRFGATYPAWLI

TRYDDCMAFLKDNRITRDVKNVMNQEQIKMLNVSEDIDFVSDHMLAKDT

PDHTRLRSLVHQAFTPRTIENLRGSIEQIAEQLLDEMEKENKADIMKSF

ASPLPFIVISELMGIPKEDRSQFQIWTNAMVDTSEGNRELTNQALREFK

DYIAKLIHDRRIKPKDDLISKLVHAEENGSKLSEKELYSMLFLLVVAGL

ETTVNLLGSGTLALLQHKKECEKLKQQPEMIATAVEELLRYTSPVVMMA

NRWAIEDFTYKGHSIKRGDMIFIGIGSANRDPNFFENPEILNINRSPNR

HISFGFGIHFCLGAPLARLEGHIAFKALLKRFPDIELAVAPDDIQWRKN

VFLRGLESLPVSLSK

>CAB13078.1-CYP109B1 Cytochrome P450 CYP109B1, Monooxygenase [*Bacillus subtilis* Subsp. *Subtilis* Str. 168]

(SEQ ID NO: 6)
MNVLNRRQALQRALLNGKNKQDAYHPFPWYESMRKDAPVSFDEENQVWS

VFLYDDVKKVVGDKELFSSCMPQQTSSIGNSIINMDPPKHTKIRSVVNK

AFTPRVMKQWEPRIQEITDELIQKFQGRSEFDLVHDFSYPLPVIVISEL

LGVPSAHMEQFKAWSDLLVSTPKDKSEEAEKAFLEERDKCEEELAAFFA

GIIEEKRNKPEQDIISILVEAEETGEKLSGEELIPFCTLLLVAGNETTT

NLISNAMYSILETPGVYEELRSHPELMPQAVEEALRFRAPAPVLRRIAK

-continued

RDTEIGGHLIKEGDMVLAFVASANRDEAKFDRPHMEDIRRHPNPHIAFG

HGIHFCLGAPLARLEANIALTSLISAFPHMECVSITPIENSVIYGLKSF

RVKM

>CAB15511.1-CYP134A1 Cyclo-L-Leucyl-L-Leucyl Dipeptide Oxidase, Pulcheriminic Synthase [*Bacillus subtilis* Subsp. *Subtilis* Str. 168]

(SEQ ID NO: 7)
MSQSIKLFSVLSDQFQNNPYAYFSQLREEDPVHYEESIDSYFISRYHDV

RYILQHPDIFTTKSLVERAEPVMRGPVLAQMHGKEHSAKRRIVVRSFIG

DALDHLSPLIKQNAENLLAPYLERGKSDLVNDFGKTFAVCVTMDMLGLD

KRDHEKISEWHSGVADFITSISQSPEARAHSLWCSEQLSQYLMPVIKER

RVNPGSDLISILCTSEYEGMALSDKDILALILNVLLAATEPADKTLALM

IYHLLNNPEQMNDVLADRSLVPRAIAETLRYKPPVQLIPRQLSQDTVVG

GMEIKKDTIVFCMIGAANRDPEAFEQPDVENIHREDLGIKSAFSGAARH

LAFGSGIHNCVGAAFAKNEIEIVANIVLDKMRNIRLEEDFCYAESGLYT

RGPVSLLVAFDGA

>CAB12004.1-CYP152A1 Fatty Acid Beta-Hydroxylating Cytochrome P450 [*Bacillus subtilis* Subsp. *Subtilis* Str. 168]

(SEQ ID NO: 8)
MNEQIPHDKSLDNSLTLLKEGYLFIKNRTERYNSDLFQARLLGKNFICM

TGAEAAKVFYDTDRFQRQNALPKRVQKSLFGVNAIQGMDGSAHIHRKML

FLSLMTPPHQKRLAELMTEEWKAAVTRWEKADEVVLFEEAKEILCRVAC

YWAGVPLKETEVKERADDFIDMVDAFGAVGPRHWKGRRARPRAEEWIEV

MIEDARAGLLKTTSGTALHEMAFHTQEDGSQLDSRMAAIELINVLRPIV

AISYFLVFSALALHEHPKYKEWLRSGNSREREMFVQEVRRYYPFGPFLG

ALVKKDFVWNNCEFKKGTSVLLDLYGTNHDPRLWDHPDEFRPERFAERE

ENLEDMIPQGGGHAEKGHRCPGEGITIEVMKASLDFLVHQIEYDVPEQS

LHYSLARMPSLPESGFVMSGIRRKS

---

What is claimed is:

1. An engineered *Bacillus subtilis* cell that: (i) expresses at least one peptide synthetase, which peptide synthetase synthesizes an acyl amino acid, and (ii) comprises a modification that comprises deletion of a fatty acid hydroxylase gene, wherein the modification results in a reduction in the number of hydroxyl groups of a fatty acid portion of the acyl amino acid, as compared to when the modification is absent.

2. The engineered *Bacillus subtilis* cell of claim 1, wherein the peptide synthetase is an engineered peptide synthetase.

3. The engineered *Bacillus subtilis* cell of claim 1, wherein the peptide synthetase is heterologous to the *Bacillus subtilis* cell.

4. The engineered *Bacillus subtilis* cell of claim 1, wherein the *Bacillus subtilis* cell has been engineered to express the peptide synthetase.

5. The engineered *Bacillus subtilis* cell of claim 4, wherein the *Bacillus subtilis* cell has been engineered to contain a polynucleotide encoding the peptide synthetase.

6. The engineered *Bacillus subtilis* cell of claim 1, wherein the fatty acid hydroxylase-gene is selected from the group consisting of bioI, Cyp107h, cyp107J1, cyp134A1, cyp109B1, cyp152A1, cyp 102A2, cyp 102A3, cyp107K1, and combinations thereof.

7. The engineered *Bacillus subtilis* cell of claim 1, wherein a fatty acid hydroxylase encoded by the fatty acid hydroxylase gene hydroxylates a branched fatty acid.

8. The engineered *Bacillus subtilis* cell of claim 1, wherein a fatty acid hydroxylase encoded by the fatty acid hydroxylase gene hydroxylates an unbranched fatty acid.

9. The engineered *Bacillus subtilis* cell of claim 1, wherein a fatty acid hydroxylase encoded by the fatty acid hydroxylase gene hydroxylates a fatty acid selected from a group consisting of caproic acid, caprylic acid, lauric acid, and myristic acid.

10. The engineered *Bacillus subtilis* cell of claim 1, wherein the acyl amino acid is acyl glycinate.

11. The engineered *Bacillus subtilis* cell of claim 1, wherein the acyl amino acid is acyl glutamate.

12. The engineered *Bacillus subtilis* cell of claim 1, wherein the acyl amino acid is acyl sarconsinate.

13. A method of making an acyl amino acid composition, the method comprising a step of: culturing the engineered cell of claim 1 under conditions and for a time sufficient for an acyl amino acid composition to be made.

14. A composition comprising (a) the *Bacillus subtilis* cell of claim 1; and (b) an acyl glycinate comprising a fatty acid covalently linked to amino acid, wherein the fatty acid (i) is a straight chain fatty acid and/or (ii) consists of an even number of carbons.

* * * * *

SEQUENCE LISTING

<160> NUMBER OF SEQ ID NOS: 20

<210> SEQ ID NO 1
<211> LENGTH: 1061
<212> TYPE: PRT
<213> ORGANISM: Bacillus subtilis

<400> SEQUENCE: 1

```
Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
            20                  25                  30

Lys Leu Ala Glu Glu Gln Gly Pro Ile Phe Gln Ile His Thr Pro Ala
        35                  40                  45

Gly Thr Thr Ile Val Val Ser Gly His Glu Leu Val Lys Glu Val Cys
    50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Phe Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Val Gln Leu
        115                 120                 125

Ile Gln Lys Trp Ala Arg Leu Asn Pro Asn Glu Ala Val Asp Val Pro
    130                 135                 140

Gly Asp Met Thr Arg Leu Thr Leu Asp Thr Ile Gly Leu Cys Gly Phe
145                 150                 155                 160

Asn Tyr Arg Phe Asn Ser Tyr Tyr Arg Glu Thr Pro His Pro Phe Ile
                165                 170                 175

Asn Ser Met Val Arg Ala Leu Asp Glu Ala Met His Gln Met Gln Arg
            180                 185                 190
```

```
Leu Asp Val Gln Asp Lys Leu Met Val Arg Thr Lys Arg Gln Phe Arg
        195                 200                 205

Tyr Asp Ile Gln Thr Met Phe Ser Leu Val Asp Ser Ile Ile Ala Glu
        210                 215                 220

Arg Arg Ala Asn Gly Asp Gln Asp Glu Lys Asp Leu Leu Ala Arg Met
225                 230                 235                 240

Leu Asn Val Glu Asp Pro Glu Thr Gly Glu Lys Leu Asp Asp Glu Asn
        245                 250                 255

Ile Arg Phe Gln Ile Ile Thr Phe Leu Ile Ala Gly His Glu Thr Thr
        260                 265                 270

Ser Gly Leu Leu Ser Phe Ala Thr Tyr Phe Leu Leu Lys His Pro Asp
        275                 280                 285

Lys Leu Lys Lys Ala Tyr Glu Glu Val Asp Arg Val Leu Thr Asp Ala
        290                 295                 300

Ala Pro Thr Tyr Lys Gln Val Leu Glu Leu Thr Tyr Ile Arg Met Ile
305                 310                 315                 320

Leu Asn Glu Ser Leu Arg Leu Trp Pro Thr Ala Pro Ala Phe Ser Leu
        325                 330                 335

Tyr Pro Lys Glu Asp Thr Val Ile Gly Gly Lys Phe Pro Ile Thr Thr
        340                 345                 350

Asn Asp Arg Ile Ser Val Leu Ile Pro Gln Leu His Arg Asp Arg Asp
        355                 360                 365

Ala Trp Gly Lys Asp Ala Glu Glu Phe Arg Pro Glu Arg Phe Glu His
        370                 375                 380

Gln Asp Gln Val Pro His His Ala Tyr Lys Pro Phe Gly Asn Gly Gln
385                 390                 395                 400

Arg Ala Cys Ile Gly Met Gln Phe Ala Leu His Glu Ala Thr Leu Val
                    405                 410                 415

Leu Gly Met Ile Leu Lys Tyr Phe Thr Leu Ile Asp His Glu Asn Tyr
        420                 425                 430

Glu Leu Asp Ile Lys Gln Thr Leu Thr Leu Lys Pro Gly Asp Phe His
        435                 440                 445

Ile Ser Val Gln Ser Arg His Gln Glu Ala Ile His Ala Asp Val Gln
        450                 455                 460

Ala Ala Glu Lys Ala Ala Pro Asp Glu Gln Lys Glu Lys Thr Glu Ala
465                 470                 475                 480

Lys Gly Ala Ser Val Ile Gly Leu Asn Asn Arg Pro Leu Leu Val Leu
                    485                 490                 495

Tyr Gly Ser Asp Thr Gly Thr Ala Glu Gly Val Ala Arg Glu Leu Ala
        500                 505                 510

Asp Thr Ala Ser Leu His Gly Val Arg Thr Lys Thr Ala Pro Leu Asn
        515                 520                 525

Asp Arg Ile Gly Lys Leu Pro Lys Glu Gly Ala Val Val Ile Val Thr
        530                 535                 540

Ser Ser Tyr Asn Gly Lys Pro Pro Ser Asn Ala Gly Gln Phe Val Gln
545                 550                 555                 560

Trp Leu Gln Glu Ile Lys Pro Gly Glu Leu Glu Gly Val His Tyr Ala
        565                 570                 575

Val Phe Gly Cys Gly Asp His Asn Trp Ala Ser Thr Tyr Gln Tyr Val
                    580                 585                 590

Pro Arg Phe Ile Asp Glu Gln Leu Ala Glu Lys Gly Ala Thr Arg Phe
        595                 600                 605
```

```
Ser Ala Arg Gly Glu Gly Asp Val Ser Gly Asp Phe Glu Gly Gln Leu
610                 615                 620

Asp Glu Trp Lys Lys Ser Met Trp Ala Asp Ala Ile Lys Ala Phe Gly
625                 630                 635                 640

Leu Glu Leu Asn Glu Asn Ala Asp Lys Glu Arg Ser Thr Leu Ser Leu
                645                 650                 655

Gln Phe Val Arg Gly Leu Gly Glu Ser Pro Leu Ala Arg Ser Tyr Glu
                660                 665                 670

Ala Ser His Ala Ser Ile Ala Glu Asn Arg Glu Leu Gln Ser Ala Asp
                675                 680                 685

Ser Asp Arg Ser Thr Arg His Ile Glu Ile Ala Leu Pro Pro Asp Val
690                 695                 700

Glu Tyr Gln Glu Gly Asp His Leu Gly Val Leu Pro Lys Asn Ser Gln
705                 710                 715                 720

Thr Asn Val Ser Arg Ile Leu His Arg Phe Gly Leu Lys Gly Thr Asp
                725                 730                 735

Gln Val Thr Leu Ser Ala Ser Gly Arg Ser Ala Gly His Leu Pro Leu
                740                 745                 750

Gly Arg Pro Val Ser Leu His Asp Leu Leu Ser Tyr Ser Val Glu Val
                755                 760                 765

Gln Glu Ala Ala Thr Arg Ala Gln Ile Arg Glu Leu Ala Ser Phe Thr
770                 775                 780

Val Cys Pro Pro His Arg Arg Glu Leu Glu Glu Leu Ser Ala Glu Gly
785                 790                 795                 800

Val Tyr Gln Glu Gln Ile Leu Lys Lys Arg Ile Ser Met Leu Asp Leu
                805                 810                 815

Leu Glu Lys Tyr Glu Ala Cys Asp Met Pro Phe Glu Arg Phe Leu Glu
                820                 825                 830

Leu Leu Arg Pro Leu Lys Pro Arg Tyr Tyr Ser Ile Ser Ser Ser Pro
                835                 840                 845

Arg Val Asn Pro Arg Gln Ala Ser Ile Thr Val Gly Val Val Arg Gly
850                 855                 860

Pro Ala Trp Ser Gly Arg Gly Glu Tyr Arg Gly Val Ala Ser Asn Asp
865                 870                 875                 880

Leu Ala Glu Arg Gln Ala Gly Asp Asp Val Val Met Phe Ile Arg Thr
                885                 890                 895

Pro Glu Ser Arg Phe Gln Leu Pro Lys Asp Pro Glu Thr Pro Ile Ile
                900                 905                 910

Met Val Gly Pro Gly Thr Gly Val Ala Pro Phe Arg Gly Phe Leu Gln
                915                 920                 925

Ala Arg Asp Val Leu Lys Arg Glu Gly Lys Thr Leu Gly Glu Ala His
930                 935                 940

Leu Tyr Phe Gly Cys Arg Asn Asp Arg Asp Phe Ile Tyr Arg Asp Glu
945                 950                 955                 960

Leu Glu Arg Phe Glu Lys Asp Gly Ile Val Thr Val His Thr Ala Phe
                965                 970                 975

Ser Arg Lys Glu Gly Met Pro Lys Thr Tyr Val Gln His Leu Met Ala
                980                 985                 990

Asp Gln Ala Asp Thr Leu Ile Ser Ile Leu Asp Arg Gly Gly Arg Leu
                995                 1000                1005

Tyr Val Cys Gly Asp Gly Ser Lys Met Ala Pro Asp Val Glu Ala
                1010                1015                1020
```

Ala Leu Gln Lys Ala Tyr Gln Ala Val His Gly Thr Gly Glu Gln
       1025                1030                1035

Glu Ala Gln Asn Trp Leu Arg His Leu Gln Asp Thr Gly Met Tyr
       1040                1045                1050

Ala Lys Asp Val Trp Ala Gly Ile
       1055                1060

<210> SEQ ID NO 2
<211> LENGTH: 1054
<212> TYPE: PRT
<213> ORGANISM: Bacillus subtilis

<400> SEQUENCE: 2

Met Lys Gln Ala Ser Ala Ile Pro Gln Pro Lys Thr Tyr Gly Pro Leu
1               5                   10                  15

Lys Asn Leu Pro His Leu Glu Lys Glu Gln Leu Ser Gln Ser Leu Trp
            20                  25                  30

Arg Ile Ala Asp Glu Leu Gly Pro Ile Phe Arg Phe Asp Phe Pro Gly
        35                  40                  45

Val Ser Ser Val Phe Val Ser Gly His Asn Leu Val Ala Glu Val Cys
    50                  55                  60

Asp Glu Lys Arg Phe Asp Lys Asn Leu Gly Lys Gly Leu Gln Lys Val
65                  70                  75                  80

Arg Glu Phe Gly Gly Asp Gly Leu Phe Thr Ser Trp Thr His Glu Pro
                85                  90                  95

Asn Trp Gln Lys Ala His Arg Ile Leu Leu Pro Ser Phe Ser Gln Lys
            100                 105                 110

Ala Met Lys Gly Tyr His Ser Met Met Leu Asp Ile Ala Thr Gln Leu
        115                 120                 125

Ile Gln Lys Trp Ser Arg Leu Asn Pro Asn Glu Glu Ile Asp Val Ala
    130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Ser Gln His Pro Phe Ile
                165                 170                 175

Thr Ser Met Leu Arg Ala Leu Lys Glu Ala Met Asn Gln Ser Lys Arg
            180                 185                 190

Leu Gly Leu Gln Asp Lys Met Met Val Lys Thr Lys Leu Gln Phe Gln
        195                 200                 205

Lys Asp Ile Glu Val Met Asn Ser Leu Val Asp Arg Met Ile Ala Glu
    210                 215                 220

Arg Lys Ala Asn Pro Asp Glu Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

```
Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Glu Tyr Pro Ile Ser Lys
                340                 345                 350

Gly Gln Pro Val Thr Val Leu Ile Pro Lys Leu His Arg Asp Gln Asn
                355                 360                 365

Ala Trp Gly Pro Asp Ala Glu Asp Phe Arg Pro Glu Arg Phe Glu Asp
370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu Gln Glu Ala Thr Met Val
                405                 410                 415

Leu Gly Leu Val Leu Lys His Phe Glu Leu Ile Asn His Thr Gly Tyr
                420                 425                 430

Glu Leu Lys Ile Lys Glu Ala Leu Thr Ile Lys Pro Asp Asp Phe Lys
                435                 440                 445

Ile Thr Val Lys Pro Arg Lys Thr Ala Ala Ile Asn Val Gln Arg Lys
                450                 455                 460

Glu Gln Ala Asp Ile Lys Ala Glu Thr Lys Pro Lys Glu Thr Lys Pro
465                 470                 475                 480

Lys His Gly Thr Pro Leu Leu Val Leu Phe Gly Ser Asn Leu Gly Thr
                485                 490                 495

Ala Glu Gly Ile Ala Gly Glu Leu Ala Ala Gln Gly Arg Gln Met Gly
                500                 505                 510

Phe Thr Ala Glu Thr Ala Pro Leu Asp Asp Tyr Ile Gly Lys Leu Pro
                515                 520                 525

Glu Glu Gly Ala Val Val Ile Val Thr Ala Ser Tyr Asn Gly Ala Pro
530                 535                 540

Pro Asp Asn Ala Ala Gly Phe Val Glu Trp Leu Lys Glu Leu Glu Glu
545                 550                 555                 560

Gly Gln Leu Lys Gly Val Ser Tyr Ala Val Phe Gly Cys Gly Asn Arg
                565                 570                 575

Ser Trp Ala Ser Thr Tyr Gln Arg Ile Pro Arg Leu Ile Asp Asp Met
                580                 585                 590

Met Lys Ala Lys Gly Ala Ser Arg Leu Thr Ala Ile Gly Glu Gly Asp
                595                 600                 605

Ala Ala Asp Asp Phe Glu Ser His Arg Glu Ser Trp Glu Asn Arg Phe
610                 615                 620

Trp Lys Glu Thr Met Asp Ala Phe Asp Ile Asn Glu Ile Ala Gln Lys
625                 630                 635                 640

Glu Asp Arg Pro Ser Leu Ser Ile Thr Phe Leu Ser Glu Ala Thr Glu
                645                 650                 655

Thr Pro Val Ala Lys Ala Tyr Gly Ala Phe Glu Gly Ile Val Leu Glu
                660                 665                 670

Asn Arg Glu Leu Gln Thr Ala Ala Ser Thr Arg Ser Thr Arg His Ile
                675                 680                 685

Glu Leu Glu Ile Pro Ala Gly Lys Thr Tyr Lys Glu Gly Asp His Ile
                690                 695                 700

Gly Ile Leu Pro Lys Asn Ser Arg Glu Leu Val Gln Arg Val Leu Ser
705                 710                 715                 720

Arg Phe Gly Leu Gln Ser Asn His Val Ile Lys Val Ser Gly Ser Ala
                725                 730                 735
```

```
His Met Ala His Leu Pro Met Asp Arg Pro Ile Lys Val Val Asp Leu
            740                 745                 750

Leu Ser Ser Tyr Val Glu Leu Gln Glu Pro Ala Ser Arg Leu Gln Leu
            755                 760                 765

Arg Glu Leu Ala Ser Tyr Thr Val Cys Pro Pro His Gln Lys Glu Leu
770                 775                 780

Glu Gln Leu Val Ser Asp Asp Gly Ile Tyr Lys Glu Gln Val Leu Ala
785                 790                 795                 800

Lys Arg Leu Thr Met Leu Asp Phe Leu Glu Asp Tyr Pro Ala Cys Glu
                805                 810                 815

Met Pro Phe Glu Arg Phe Leu Ala Leu Leu Pro Ser Leu Lys Pro Arg
            820                 825                 830

Tyr Tyr Ser Ile Ser Ser Ser Pro Lys Val His Ala Asn Ile Val Ser
            835                 840                 845

Met Thr Val Gly Val Val Lys Ala Ser Ala Trp Ser Gly Arg Gly Glu
            850                 855                 860

Tyr Arg Gly Val Ala Ser Asn Tyr Leu Ala Glu Leu Asn Thr Gly Asp
865                 870                 875                 880

Ala Ala Ala Cys Phe Ile Arg Thr Pro Gln Ser Gly Phe Gln Met Pro
                885                 890                 895

Asn Asp Pro Glu Thr Pro Met Ile Met Val Gly Pro Gly Thr Gly Ile
            900                 905                 910

Ala Pro Phe Arg Gly Phe Ile Gln Ala Arg Ser Val Leu Lys Lys Glu
            915                 920                 925

Gly Ser Thr Leu Gly Glu Ala Leu Leu Tyr Phe Gly Cys Arg Arg Pro
930                 935                 940

Asp His Asp Asp Leu Tyr Arg Glu Glu Leu Asp Gln Ala Glu Gln Asp
945                 950                 955                 960

Gly Leu Val Thr Ile Arg Arg Cys Tyr Ser Arg Val Glu Asn Glu Pro
                965                 970                 975

Lys Gly Tyr Val Gln His Leu Leu Lys Gln Asp Thr Gln Lys Leu Met
            980                 985                 990

Thr Leu Ile Glu Lys Gly Ala His Ile Tyr Val Cys Gly Asp Gly Ser
            995                1000                1005

Gln Met Ala Pro Asp Val Glu Arg Thr Leu Arg Leu Ala Tyr Glu
           1010                1015                1020

Ala Glu Lys Ala Ala Ser Gln Glu Glu Ser Ala Val Trp Leu Gln
           1025                1030                1035

Lys Leu Gln Asp Gln Arg Arg Tyr Val Lys Asp Val Trp Thr Gly
           1040                1045                1050

Met

<210> SEQ ID NO 3
<211> LENGTH: 395
<212> TYPE: PRT
<213> ORGANISM: Bacillus subtilis

<400> SEQUENCE: 3

Met Thr Ile Ala Ser Ser Thr Ala Ser Ser Glu Phe Leu Lys Asn Pro
1               5                  10                  15

Tyr Ser Phe Tyr Asp Thr Leu Arg Ala Val His Pro Ile Tyr Lys Gly
                20                  25                  30

Ser Phe Leu Lys Tyr Pro Gly Trp Tyr Val Thr Gly Tyr Glu Glu Thr
            35                  40                  45
```

```
Ala Ala Ile Leu Lys Asp Ala Arg Phe Lys Val Arg Thr Pro Leu Pro
    50                  55                  60

Glu Ser Ser Thr Lys Tyr Gln Asp Leu Ser His Val Gln Asn Gln Met
 65                  70                  75                  80

Met Leu Phe Gln Asn Gln Pro Asp His Arg Arg Leu Arg Thr Leu Ala
                 85                  90                  95

Ser Gly Ala Phe Thr Pro Arg Thr Thr Glu Ser Tyr Gln Pro Tyr Ile
                100                 105                 110

Ile Glu Thr Val His His Leu Leu Asp Gln Val Gln Gly Lys Lys Lys
            115                 120                 125

Met Glu Val Ile Ser Asp Phe Ala Phe Pro Leu Ala Ser Phe Val Ile
130                 135                 140

Ala Asn Ile Ile Gly Val Pro Glu Glu Asp Arg Glu Gln Leu Lys Glu
145                 150                 155                 160

Trp Ala Ala Ser Leu Ile Gln Thr Ile Asp Phe Thr Arg Ser Arg Lys
                165                 170                 175

Ala Leu Thr Glu Gly Asn Ile Met Ala Val Gln Ala Met Ala Tyr Phe
                180                 185                 190

Lys Glu Leu Ile Gln Lys Arg Lys Arg His Pro Gln Gln Asp Met Ile
            195                 200                 205

Ser Met Leu Leu Lys Gly Arg Glu Lys Asp Lys Leu Thr Glu Glu Glu
210                 215                 220

Ala Ala Ser Thr Cys Ile Leu Leu Ala Ile Ala Gly His Glu Thr Thr
225                 230                 235                 240

Val Asn Leu Ile Ser Asn Ser Val Leu Cys Leu Leu Gln His Pro Glu
                245                 250                 255

Gln Leu Leu Lys Leu Arg Glu Asn Pro Asp Leu Ile Gly Thr Ala Val
                260                 265                 270

Glu Glu Cys Leu Arg Tyr Glu Ser Pro Thr Gln Met Thr Ala Arg Val
            275                 280                 285

Ala Ser Glu Asp Ile Asp Ile Cys Gly Val Thr Ile Arg Gln Gly Glu
290                 295                 300

Gln Val Tyr Leu Leu Leu Gly Ala Ala Asn Arg Asp Pro Ser Ile Phe
305                 310                 315                 320

Thr Asn Pro Asp Val Phe Asp Ile Thr Arg Ser Pro Asn Pro His Leu
                325                 330                 335

Ser Phe Gly His Gly His His Val Cys Leu Gly Ser Ser Leu Ala Arg
                340                 345                 350

Leu Glu Ala Gln Ile Ala Ile Asn Thr Leu Leu Gln Arg Met Pro Ser
            355                 360                 365

Leu Asn Leu Ala Asp Phe Glu Trp Arg Tyr Arg Pro Leu Phe Gly Phe
370                 375                 380

Arg Ala Leu Glu Glu Leu Pro Val Thr Phe Glu
385                 390                 395

<210> SEQ ID NO 4
<211> LENGTH: 410
<212> TYPE: PRT
<213> ORGANISM: Bacillus subtilis

<400> SEQUENCE: 4

Met Ser Ser Lys Glu Lys Lys Ser Val Thr Ile Leu Thr Glu Ser Gln
 1               5                  10                  15

Leu Ser Ser Arg Ala Phe Lys Asp Glu Ala Tyr Glu Phe Tyr Lys Glu
                20                  25                  30
```

Leu Arg Lys Ser Gln Ala Leu Tyr Pro Leu Ser Leu Gly Ala Leu Gly
         35                  40                  45

Lys Gly Trp Leu Ile Ser Arg Tyr Asp Asp Ala Ile His Leu Leu Lys
 50                  55                  60

Asn Glu Lys Leu Lys Lys Asn Tyr Glu Asn Val Phe Thr Ala Lys Glu
 65                  70                  75                  80

Lys Arg Pro Ala Leu Leu Lys Asn Glu Thr Leu Thr Lys His Met
             85                  90                  95

Leu Asn Ser Asp Pro Pro Asp His Asn Arg Leu Arg Thr Leu Val Gln
                100                 105                 110

Lys Ala Phe Thr His Arg Met Ile Leu Gln Leu Glu Asp Lys Ile Gln
             115                 120                 125

His Ile Ala Asp Ser Leu Leu Asp Lys Val Gln Pro Asn Lys Phe Met
        130                 135                 140

Asn Leu Val Asp Asp Tyr Ala Phe Pro Leu Pro Ile Ile Val Ile Ser
145                 150                 155                 160

Glu Met Leu Gly Ile Pro Leu Glu Asp Arg Gln Lys Phe Arg Val Trp
                165                 170                 175

Ser Gln Ala Ile Ile Asp Phe Ser Asp Ala Pro Glu Arg Leu Gln Glu
        180                 185                 190

Asn Asp His Leu Leu Gly Glu Phe Val Glu Tyr Leu Glu Ser Leu Val
            195                 200                 205

Arg Lys Lys Arg Arg Glu Pro Ala Gly Asp Leu Ile Ser Ala Leu Ile
    210                 215                 220

Gln Ala Glu Ser Glu Gly Thr Gln Leu Ser Thr Glu Leu Tyr Ser
225                 230                 235                 240

Met Ile Met Leu Leu Ile Val Ala Gly His Glu Thr Thr Val Asn Leu
                245                 250                 255

Ile Thr Asn Met Thr Tyr Ala Leu Met Cys His His Asp Gln Leu Glu
            260                 265                 270

Lys Leu Arg Gln Gln Pro Asp Leu Met Asn Ser Ala Ile Glu Glu Ala
    275                 280                 285

Leu Arg Phe His Ser Pro Val Glu Leu Thr Thr Ile Arg Trp Thr Ala
    290                 295                 300

Glu Pro Phe Ile Leu His Gly Gln Glu Ile Lys Arg Lys Asp Val Ile
305                 310                 315                 320

Ile Ile Ser Leu Ala Ser Ala Asn Arg Asp Glu Lys Ile Phe Pro Asn
            325                 330                 335

Ala Asp Ile Phe Asp Ile Glu Arg Lys Asn Asn Arg His Ile Ala Phe
            340                 345                 350

Gly His Gly Asn His Phe Cys Leu Gly Ala Gln Leu Ala Arg Leu Glu
        355                 360                 365

Ala Lys Ile Ala Ile Ser Thr Leu Leu Arg Arg Cys Pro Asn Ile Gln
    370                 375                 380

Leu Lys Gly Glu Lys Lys Gln Met Lys Trp Lys Gly Asn Phe Leu Met
385                 390                 395                 400

Arg Ala Leu Glu Glu Leu Pro Ile Ser Phe
                405                 410

<210> SEQ ID NO 5
<211> LENGTH: 407
<212> TYPE: PRT
<213> ORGANISM: Bacillus subtilis

<400> SEQUENCE: 5

Met Gln Met Glu Lys Leu Met Phe His Pro His Gly Lys Glu Phe His
1               5                   10                  15

His Asn Pro Phe Ser Val Leu Gly Arg Phe Glu Glu Pro Ile
            20                  25                  30

His Arg Phe Glu Leu Lys Arg Phe Gly Ala Thr Tyr Pro Ala Trp Leu
            35                  40                  45

Ile Thr Arg Tyr Asp Asp Cys Met Ala Phe Leu Lys Asp Asn Arg Ile
50                  55                  60

Thr Arg Asp Val Lys Asn Val Met Asn Gln Glu Gln Ile Lys Met Leu
65                  70                  75                  80

Asn Val Ser Glu Asp Ile Asp Phe Val Ser Asp His Met Leu Ala Lys
                85                  90                  95

Asp Thr Pro Asp His Thr Arg Leu Arg Ser Leu Val His Gln Ala Phe
                100                 105                 110

Thr Pro Arg Thr Ile Glu Asn Leu Arg Gly Ser Ile Glu Gln Ile Ala
            115                 120                 125

Glu Gln Leu Leu Asp Glu Met Glu Lys Glu Asn Lys Ala Asp Ile Met
130                 135                 140

Lys Ser Phe Ala Ser Pro Leu Pro Phe Ile Val Ile Ser Glu Leu Met
145                 150                 155                 160

Gly Ile Pro Lys Glu Asp Arg Ser Gln Phe Gln Ile Trp Thr Asn Ala
                165                 170                 175

Met Val Asp Thr Ser Glu Gly Asn Arg Glu Leu Thr Asn Gln Ala Leu
                180                 185                 190

Arg Glu Phe Lys Asp Tyr Ile Ala Lys Leu Ile His Asp Arg Arg Ile
            195                 200                 205

Lys Pro Lys Asp Asp Leu Ile Ser Lys Leu Val His Ala Glu Glu Asn
210                 215                 220

Gly Ser Lys Leu Ser Glu Lys Glu Leu Tyr Ser Met Leu Phe Leu Leu
225                 230                 235                 240

Val Val Ala Gly Leu Glu Thr Thr Val Asn Leu Leu Gly Ser Gly Thr
                245                 250                 255

Leu Ala Leu Leu Gln His Lys Lys Glu Cys Glu Lys Leu Lys Gln Gln
                260                 265                 270

Pro Glu Met Ile Ala Thr Ala Val Glu Glu Leu Leu Arg Tyr Thr Ser
            275                 280                 285

Pro Val Val Met Met Ala Asn Arg Trp Ala Ile Glu Asp Phe Thr Tyr
290                 295                 300

Lys Gly His Ser Ile Lys Arg Gly Asp Met Ile Phe Ile Gly Ile Gly
305                 310                 315                 320

Ser Ala Asn Arg Asp Pro Asn Phe Phe Glu Asn Pro Glu Ile Leu Asn
                325                 330                 335

Ile Asn Arg Ser Pro Asn Arg His Ile Ser Phe Gly Phe Gly Ile His
            340                 345                 350

Phe Cys Leu Gly Ala Pro Leu Ala Arg Leu Glu Gly His Ile Ala Phe
            355                 360                 365

Lys Ala Leu Leu Lys Arg Phe Pro Asp Ile Glu Leu Ala Val Ala Pro
370                 375                 380

Asp Asp Ile Gln Trp Arg Lys Asn Val Phe Leu Arg Gly Leu Glu Ser
385                 390                 395                 400

Leu Pro Val Ser Leu Ser Lys
                405

<210> SEQ ID NO 6
<211> LENGTH: 396
<212> TYPE: PRT
<213> ORGANISM: Bacillus subtilis

<400> SEQUENCE: 6

Met Asn Val Leu Asn Arg Arg Gln Ala Leu Gln Arg Ala Leu Leu Asn
1               5                   10                  15

Gly Lys Asn Lys Gln Asp Ala Tyr His Pro Phe Pro Trp Tyr Glu Ser
            20                  25                  30

Met Arg Lys Asp Ala Pro Val Ser Phe Asp Glu Glu Asn Gln Val Trp
        35                  40                  45

Ser Val Phe Leu Tyr Asp Asp Val Lys Lys Val Val Gly Asp Lys Glu
50                  55                  60

Leu Phe Ser Ser Cys Met Pro Gln Gln Thr Ser Ser Ile Gly Asn Ser
65                  70                  75                  80

Ile Ile Asn Met Asp Pro Pro Lys His Thr Lys Ile Arg Ser Val Val
                85                  90                  95

Asn Lys Ala Phe Thr Pro Arg Val Met Lys Gln Trp Glu Pro Arg Ile
            100                 105                 110

Gln Glu Ile Thr Asp Glu Leu Ile Gln Lys Phe Gln Gly Arg Ser Glu
        115                 120                 125

Phe Asp Leu Val His Asp Phe Ser Tyr Pro Leu Pro Val Ile Val Ile
    130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Glu Leu Ala
            180                 185                 190

Ala Phe Phe Ala Gly Ile Ile Glu Glu Lys Arg Asn Lys Pro Glu Gln
        195                 200                 205

Asp Ile Ile Ser Ile Leu Val Glu Ala Glu Thr Gly Glu Lys Leu
    210                 215                 220

Ser Gly Glu Glu Leu Ile Pro Phe Cys Thr Leu Leu Val Ala Gly
225                 230                 235                 240

Asn Glu Thr Thr Thr Asn Leu Ile Ser Asn Ala Met Tyr Ser Ile Leu
                245                 250                 255

Glu Thr Pro Gly Val Tyr Glu Glu Leu Arg Ser His Pro Glu Leu Met
            260                 265                 270

Pro Gln Ala Val Glu Glu Ala Leu Arg Phe Arg Ala Pro Ala Pro Val
        275                 280                 285

Leu Arg Arg Ile Ala Lys Arg Asp Thr Glu Ile Gly Gly His Leu Ile
    290                 295                 300

Lys Glu Gly Asp Met Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Gly His Gly Ile His Phe Cys Leu Gly Ala
            340                 345                 350

Pro Leu Ala Arg Leu Glu Ala Asn Ile Ala Leu Thr Ser Leu Ile Ser
        355                 360                 365

```
Ala Phe Pro His Met Glu Cys Val Ser Ile Thr Pro Ile Glu Asn Ser
    370                 375                 380

Val Ile Tyr Gly Leu Lys Ser Phe Arg Val Lys Met
385                 390                 395

<210> SEQ ID NO 7
<211> LENGTH: 405
<212> TYPE: PRT
<213> ORGANISM: Bacillus subtilis

<400> SEQUENCE: 7

Met Ser Gln Ser Ile Lys Leu Phe Ser Val Leu Ser Asp Gln Phe Gln
1               5                   10                  15

Asn Asn Pro Tyr Ala Tyr Phe Ser Gln Leu Arg Glu Glu Asp Pro Val
            20                  25                  30

His Tyr Glu Glu Ser Ile Asp Ser Tyr Phe Ile Ser Arg Tyr His Asp
        35                  40                  45

Val Arg Tyr Ile Leu Gln His Pro Asp Ile Phe Thr Thr Lys Ser Leu
    50                  55                  60

Val Glu Arg Ala Glu Pro Val Met Arg Gly Pro Val Leu Ala Gln Met
65                  70                  75                  80

His Gly Lys Glu His Ser Ala Lys Arg Ile Val Val Arg Ser Phe
                85                  90                  95

Ile Gly Asp Ala Leu Asp His Leu Ser Pro Leu Ile Lys Gln Asn Ala
            100                 105                 110

Glu Asn Leu Leu Ala Pro Tyr Leu Glu Arg Gly Lys Ser Asp Leu Val
        115                 120                 125

Asn Asp Phe Gly Lys Thr Phe Ala Val Cys Val Thr Met Asp Met Leu
130                 135                 140

Gly Leu Asp Lys Arg Asp His Glu Lys Ile Ser Glu Trp His Ser Gly
145                 150                 155                 160

Val Ala Asp Phe Ile Thr Ser Ile Ser Gln Ser Pro Glu Ala Arg Ala
                165                 170                 175

His Ser Leu Trp Cys Ser Glu Gln Leu Ser Gln Tyr Leu Met Pro Val
            180                 185                 190

Ile Lys Glu Arg Arg Val Asn Pro Gly Ser Asp Leu Ile Ser Ile Leu
        195                 200                 205

Cys Thr Ser Glu Tyr Glu Gly Met Ala Leu Ser Asp Lys Asp Ile Leu
210                 215                 220

Ala Leu Ile Leu Asn Val Leu Leu Ala Ala Thr Glu Pro Ala Asp Lys
225                 230                 235                 240

Thr Leu Ala Leu Met Ile Tyr His Leu Leu Asn Asn Pro Glu Gln Met
                245                 250                 255

Asn Asp Val Leu Ala Asp Arg Ser Leu Val Pro Arg Ala Ile Ala Glu
            260                 265                 270

Thr Leu Arg Tyr Lys Pro Pro Val Gln Leu Ile Pro Arg Gln Leu Ser
        275                 280                 285

Gln Asp Thr Val Val Gly Gly Met Glu Ile Lys Lys Asp Thr Ile Val
290                 295                 300

Phe Cys Met Ile Gly Ala Ala Asn Arg Asp Pro Glu Ala Phe Glu Gln
305                 310                 315                 320

Pro Asp Val Phe Asn Ile His Arg Glu Asp Leu Gly Ile Lys Ser Ala
                325                 330                 335
```

```
Phe Ser Gly Ala Ala Arg His Leu Ala Phe Gly Ser Gly Ile His Asn
                340                 345                 350

Cys Val Gly Ala Ala Phe Ala Lys Asn Glu Ile Glu Ile Val Ala Asn
                355                 360                 365

Ile Val Leu Asp Lys Met Arg Asn Ile Arg Leu Glu Glu Asp Phe Cys
370                 375                 380

Tyr Ala Glu Ser Gly Leu Tyr Thr Arg Gly Pro Val Ser Leu Leu Val
385                 390                 395                 400

Ala Phe Asp Gly Ala
                405

<210> SEQ ID NO 8
<211> LENGTH: 417
<212> TYPE: PRT
<213> ORGANISM: Bacillus subtilis

<400> SEQUENCE: 8

Met Asn Glu Gln Ile Pro His Asp Lys Ser Leu Asp Asn Ser Leu Thr
1               5                   10                  15

Leu Leu Lys Glu Gly Tyr Leu Phe Ile Lys Asn Arg Thr Glu Arg Tyr
                20                  25                  30

Asn Ser Asp Leu Phe Gln Ala Arg Leu Leu Gly Lys Asn Phe Ile Cys
            35                  40                  45

Met Thr Gly Ala Glu Ala Lys Val Phe Tyr Asp Thr Asp Arg Phe
        50                  55                  60

Gln Arg Gln Asn Ala Leu Pro Lys Arg Val Gln Lys Ser Leu Phe Gly
65                  70                  75                  80

Val Asn Ala Ile Gln Gly Met Asp Gly Ser Ala His Ile His Arg Lys
                85                  90                  95

Met Leu Phe Leu Ser Leu Met Thr Pro Pro His Gln Lys Arg Leu Ala
            100                 105                 110

Glu Leu Met Thr Glu Glu Trp Lys Ala Ala Val Thr Arg Trp Glu Lys
        115                 120                 125

Ala Asp Glu Val Val Leu Phe Glu Glu Ala Lys Glu Ile Leu Cys Arg
    130                 135                 140

Val Ala Cys Tyr Trp Ala Gly Val Pro Leu Lys Glu Thr Glu Val Lys
145                 150                 155                 160

Glu Arg Ala Asp Asp Phe Ile Asp Met Val Asp Ala Phe Gly Ala Val
                165                 170                 175

Gly Pro Arg His Trp Lys Gly Arg Arg Ala Arg Pro Arg Ala Glu Glu
            180                 185                 190

Trp Ile Glu Val Met Ile Glu Asp Ala Arg Ala Gly Leu Leu Lys Thr
        195                 200                 205

Thr Ser Gly Thr Ala Leu His Glu Met Ala Phe His Thr Gln Glu Asp
    210                 215                 220

Gly Ser Gln Leu Asp Ser Arg Met Ala Ala Ile Glu Leu Ile Asn Val
225                 230                 235                 240

Leu Arg Pro Ile Val Ala Ile Ser Tyr Phe Leu Val Phe Ser Ala Leu
                245                 250                 255

Ala Leu His Glu His Pro Lys Tyr Lys Glu Trp Leu Arg Ser Gly Asn
            260                 265                 270

Ser Arg Glu Arg Glu Met Phe Val Gln Glu Val Arg Arg Tyr Tyr Pro
        275                 280                 285
```

```
Phe Gly Pro Phe Leu Gly Ala Leu Val Lys Lys Asp Phe Val Trp Asn
    290                 295                 300

Asn Cys Glu Phe Lys Lys Gly Thr Ser Val Leu Leu Asp Leu Tyr Gly
305                 310                 315                 320

Thr Asn His Asp Pro Arg Leu Trp Asp His Pro Asp Glu Phe Arg Pro
                325                 330                 335

Glu Arg Phe Ala Glu Arg Glu Asn Leu Phe Asp Met Ile Pro Gln
            340                 345                 350

Gly Gly His Ala Glu Lys Gly His Arg Cys Pro Gly Glu Gly Ile
        355                 360                 365

Thr Ile Glu Val Met Lys Ala Ser Leu Asp Phe Leu Val His Gln Ile
    370                 375                 380

Glu Tyr Asp Val Pro Glu Gln Ser Leu His Tyr Ser Leu Ala Arg Met
385                 390                 395                 400

Pro Ser Leu Pro Glu Ser Gly Phe Val Met Ser Gly Ile Arg Arg Lys
                405                 410                 415

Ser

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaactaaaaa agggtagcct aaaaa                                          25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaagaagttt tagctatagg agattcc                                        27

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gattgtactg agagtgcacc atatgcttgc attaagagaa atttaca                  47

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcggtatttc acaccgcagg gaatacaagt cttttaatca g                        41
```

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggtgtgaa ataccgcaca gatgcgtaag gagaaaa                               37

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atatggtgca ctctcagtac aatctgctct gatgccgca                             39

<210> SEQ ID NO 15
<211> LENGTH: 7851
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgct tgcattaaga gaaatttaca gggtgcttca aattgacggc cggtttttata     240 tcagtattga cacaaatacc ggtgaaaaag agaaaacgta tattcaactg ctgaaagacc     300
agcatttcag ggatctttct gttatcaggc gtgcttcctg tctatgtatt gtggctgtta     360
aataaaaaat ttctcgggaa atatatccaa gatcctcgta ttaggatttg ggtatatttt     420
cttaattttt tattttttgc atatacttta tattaaaaaa agttttttc atataaactt     480 ataacagaag aaagaacaaa gaggtgatat cagacagggc agacattctt tgtgaacaaa     540
aggaatgaat attcattccg taaacgaatc ggaggttgtc agattacatg atatccgcat     600
ccagcagtaa atacgacatg attatgaaag cgtcagtctc acttttacg gaaggggggtt     660 ttgacgctac cactattcct atgatagctg aacgtgctca tgtagggaca ggaacgatct     720
atcgttattt tgacagcaaa gaaacactcg ttaacgtact gtttcaagaa agcatccagc     780
gatttacgga aaaactgaag caagacgttt cagaattgcc tgtcagagaa ggctttcacc     840
acgtattttg ctgtctcgtt cagtttacga aagagagcga ctatgcgctt ttttttcttg     900
aaaccaaaaa agacgctcat tacttaaatc atacaagcaa aaaatgata gaaaatctga     960 ctcaaatgct tgatgactat tttaataagg gaaaagcgga aggcgtgatt cgcagcctgc    1020
cctctaatgt gttaattgcg attgtattag gggcgtttct caagatatat cagctcgttc    1080
aaacaggtga tatagagatg gacactgatt taattactga attggaacaa tgctgctggg    1140
acgccattaa gcttcattca tcacaaaaat aggaaaggga gatgttaatg aaacaggcaa    1200
gcgcaatacc tcagcccaaa acatacggac ctttaaaaaa tcttccgcat ctggaaaaag    1260

```
aacagctttc tcaatcctta tggcggatag ctgatgaatt gggaccgatt ttccgttttg    1320
attttccggg agtatccagt gttttgtgt ccggccacaa tcttgtggct gaagtgtgtg     1380
atgaaaaacg ctttgacaag aaccttggca aaggcttgca aaaggtgcgt gagttcgggg   1440
gagatggctt atttacaagc tggacgcacg aaccgaactg gcaaaaagcc caccgcattt   1500
tgctgccgag ttttagtcaa aaagcgatga aaggctatca ttctatgatg ctggatatcg   1560
caacccagct gattcaaaag tggagccggt taaaccctaa tgaagaaatt gatgtagcgg   1620
acgatatgac acgtctgacg cttgatacga ttgggttatg cgggtttaac tatcgattca   1680
acagctttta ccgtgattca cagcatccgt ttatcaccag tatgctccgt gccttaaaag   1740
aggcgatgaa tcaatcgaaa agactgggcc tgcaagataa aatgatggtg aaaacgaagc   1800
tgcagttcca aaaggatata gaagtcatga actccctggt tgatagaatg atagcggagc   1860
gaaaggcgaa tccggatgaa aacattaagg atctcttgtc tctcatgctt tatgccaaag   1920
atccagtaac gggtgaaacg ctggatgacg aaaacattcg ataccaaatc atcacatttt   1980
taattgctgg acatgagaca acaagcgggt tgctatcctt tgcgatttat tgtctgctta   2040
cacatccgga aaaactgaaa aaagctcagg aggaagcgga tcgcgtgtta acggatgaca   2100
cgcctgaata taaacaaatc cagcagctca atacattcg gatggtttta aatgaaaccc    2160
tcagactgta tccaacagct ccggcttttt ctctatatgc gaaggaggat actgttctag   2220
gcggggaata tccgatcagc aaagggcagc cagtcactgt tttaattcca aaactgcacc   2280
gggatcaaaa cgcttgggga ccggatgcgg aagatttccg tccggaacgg tttgaggatc   2340
cttcaagtat ccctcaccat gcgtataagc cgtttggaaa cggacagcgc gcttgtattg   2400
gcatgcagtt tgctcttcaa gaagcgacaa tggttctcgg tcttgtatta aagcattttg   2460
aattgataaa ccatactggc tacgaactaa aaatcaaaga agcattaacg atcaagccgg   2520
atgattttaa aattactgtg aaaccgcgaa aaacagcggc aatcaatgta cagagaaaag   2580
aacaggcaga catcaaagca gaaacaaagc caaagaaaac caaacctaaa cacggcacac   2640
ctttacttgt tcttttggt tcaaatcttg ggacagctga gggaatagcc ggtgaactgg    2700
ctgctcaagg ccgccagatg ggctttacag ctgaaacggc tccgcttgat gattatatcg   2760
gcaagctccc tgaagaaggg gcagtcgtca ttgtaacggc ttcttataat ggggcgccgc   2820
ctgataatgc tgccggattt gtagagtggc tgaaagagct tgaggaaggc caattgaaag   2880
gtgtttccta tgcggtattc ggctgcggaa accggagctg ggccagcacg tatcagcgga   2940
ttccccgcct gattgatgac atgatgaaag caaaggggc atcgcgttta acagcgattg    3000
gggaaggtga cgccgccgat gattttgaaa gccaccgcga gtcttgggaa aaccgcttct   3060
ggaaggaaac gatggacgca tttgatatta cgaaatagc ccagaaagaa gacaggcctt    3120
cattatcgat tactttctc agtgaagcga cggaaacgcc ggttgctaaa gcatatggcg    3180
cgtttgaagg gattgtgtta gagaatcgag aactccagac agctgccagc acgcgttcaa   3240
cccgccatat tgaattggaa attccggctg gtaaaacata taagaaggc gatcatatcg    3300 gaatcctgcc aaagaacagc agggagcttg ttcagcgggt tctcagccga ttcggttttgc  3360 agtccaatca tgtgataaaa gtaagcgaa gcgctcatat ggctcatctg ccgatggatc    3420
ggccaatcaa agtagtggat ttattgtcgt cctatgtaga gctgcaggaa ccggcatcaa   3480
ggcttcagct tcgggagctg gcctcttata cagtttgtcc gccgcatcaa aaagagctgg   3540
aacagctcgt tcagatgat ggcatttaca aagagcaggg acttgcaaaa cgtcttacca    3600
tgcttgattt tttagaggat tatcctgctt gcgaaatgcc gtttgaacgg ttttagcac    3660
```

```
ttttgccatc actaaaaccg agatactatt ccatttcaag ctcaccgaaa gttcatgcaa    3720
atatcgtgag catgacggta ggagttgtga aagcctcagc atggagcggc cgaggtgaat    3780
accggggtgt cgcctctaat tatttagcag aattgaatac aggtgatgca gcagcttgct    3840
tcattcgtac gccgcagtcc ggatttcaga tgccgaatga tcctgaaacg cctatgatta    3900
tggtcgggcc gggcacagga attgcgccat tcagaggctt tattcaggca agatcggttt    3960
tgaagaagga aggaagcacc cttggtgaag cacttttata cttcggctgc cgccgcccgg    4020
accatgacga cctttacaga gaagagctgg atcaagcgga acaggacggt ttggtcacaa    4080
tccgccgatg ctactcgcgc gtcgaaaacg aaccaaaagg atatgtccag cacttgctca    4140
agcaagatac gcagaaattg atgacactca ttgaaaaagg ggctcatatt tacgtatgcg    4200
gtgatggatc gcaaatggct cctgatgtag agagaacttt gcgattggca tatgaagctg    4260
aaaaagcagc aagtcaggaa gaatcagctg tatggctgca aaagctgcaa gatcaaagac    4320
gttatgtgaa agacgtttgg acaggaatgt aaaatataaa atcccgccaa tctgattggc    4380
gggattgctt tgcatatgag aaaaccggca cgataatgaa atctactgaa aaggatgtta    4440
tagggagtat cgcgccggcc ttattattca tatcggcatg cagaggcaaa agtttagttc    4500
tttttacctt gttttttaaaa ataaatagtc tgaaagtctt gttttttgatt ttcgactcag    4560 gcttttggca ttttgttctt tcttattcct taagatcagt catctgttga agattgatgc    4620
ttgaattgct gttccacatg cttacggtaa tgaaagtcat gaatcagccg aatggtcggc    4680
ctgattaaca gcagcaaact tccgatcgca aacagccata tccctgccga cattaaccgg    4740
tcataaaaaa agaaaaaact tccaacgaga aacatagcac cgatgataaa atcgtttact    4800
gtataaagaa cctatatcg ttttttgaaa aaagctcat atcgtttcaa ctcttttgg    4860 atgtcatgtt cttcattcc tttcattatc atccctccat tcaattttgg cttacccttta    4920 cgtaaacggc atgtaaacat aagggctgcc ttgctgaaag aagacataat caacgatcag    4980
aaactaaagt aaaaaagtga tctgtatagg atctctttttt tacgatttca tcgcctgaac    5040
aataagagca gtcaaagttt ttgcccctttt aggaaccaag tgaacaccat caggggtaaa    5100
atattccgga tgctgaagag cttctgtatg ccagtcaact aacgtaacat tttgatgtgc    5160
gtgggcctgt tgctgcaaag attcatttac cttgcttttcc cattggcggg gaacccgtgt    5220
attgacaaga taaatatgag cttttgagaa agattgaagc agttgttcga tttggctgtt    5280
tgtaaaatag ccattggttc caagctcaat gatgacagcc ttgttcggct gattaaaaga    5340
cttgtattcc ctgcggtgtg aaataccgca cagatgcgta aggagaaaat accgcatcag    5400
gcgccattcg ccattcaggc tgcgcaactg ttgggaaggg cgatcggtgc gggcctcttc    5460
gctattacgc cagctggcga agggggatg tgctgcaagg cgattaagtt gggtaacgcc    5520
agggttttcc cagtcacgac gttgtaaaac gacggccagt gaattcgagc tcggtacccg    5580
gggatcctct agagtcgacc tgcaggcatg caagcttggc gtaatcatgg tcatagctgt    5640
ttcctgtgtg aaattgttat ccgctcacaa ttccacacaa catacgagcc ggaagcataa    5700
agtgtaaagc ctggggtgcc taatgagtga gctaactcac attaattgcg ttgcgctcac    5760
tgcccgcttt ccagtcggga aacctgtcgt gccagctgca ttaatgaatc ggccaacgcg    5820
cggggagagg cggtttgcgt attgggcgct cttccgcttc ctcgctcact gactcgctgc    5880
gctcggtcgt tcggctgcgg cgagcggtat cagctcactc aaaggcggta atacggttat    5940
ccacagaatc aggggataac gcaggaaaga acatgtgagc aaaaggccag caaaaggcca    6000
```

```
ggaaccgtaa aaaggccgcg ttgctggcgt ttttccatag gctccgcccc cctgacgagc    6060
atcacaaaaa tcgacgctca agtcagaggt ggcgaaaccc gacaggacta taaagatacc    6120
aggcgtttcc ccctggaagc tccctcgtgc gctctcctgt tccgaccctg ccgcttaccg    6180
gatacctgtc cgcctttctc ccttcgggaa gcgtggcgct ttctcatagc tcacgctgta    6240
ggtatctcag ttcggtgtag gtcgttcgct ccaagctggg ctgtgtgcac gaaccccccg    6300
ttcagcccga ccgctgcgcc ttatccggta actatcgtct tgagtccaac ccggtaagac    6360
acgacttatc gccactggca gcagccactg gtaacaggat tagcagagcg aggtatgtag    6420
gcggtgctac agagttcttg aagtggtggc ctaactacgg ctacactaga agaacagtat    6480
ttggtatctg cgctctgctg aagccagtta ccttcggaaa aagagttggt agctcttgat    6540
ccggcaaaca aaccaccgct ggtagcggtg gttttttttgt ttgcaagcag cagattacgc    6600
gcagaaaaaa aggatctcaa gaagatcctt tgatcttttc tacggggtct gacgctcagt    6660
ggaacgaaaa ctcacgttaa gggattttgg tcatgagatt atcaaaaagg atcttcacct    6720
agatcctttt aaattaaaaa tgaagtttta atcaatcta aagtatatat gagtaaactt    6780
ggtctgacag ttaccaatgc ttaatcagtg aggcacctat ctcagcgatc tgtctatttc    6840
gttcatccat agttgcctga ctccccgtcg tgtagataac tacgatacgg gagggcttac    6900
catctggccc cagtgctgca atgataccgc gagacccacg ctcaccggct ccagatttat    6960
cagcaataaa ccagccagcc ggaagggccg agcgcagaag tggtcctgca actttatccg    7020
cctccatcca gtctattaat tgttgccggg aagctagagt aagtagttcg ccagttaata    7080
gtttgcgcaa cgttgttgcc attgctacag gcatcgtggt gtcacgctcg tcgtttggta    7140
tggcttcatt cagctccggt tcccaacgat caaggcgagt tacatgatcc cccatgttgt    7200
gcaaaaaagc ggttagctcc ttcggtcctc cgatcgttgt cagaagtaag ttggccgcag    7260
tgttatcact catggttatg gcagcactgc ataattctct tactgtcatg ccatccgtaa    7320
gatgcttttc tgtgactggt gagtactcaa ccaagtcatt ctgagaatag tgtatgcggc    7380
gaccgagttg ctcttgcccg gcgtcaatac gggataatac cgcgccacat agcagaactt    7440
taaaagtgct catcattgga aaacgttctt cggggcgaaa actctcaagg atcttaccgc    7500
tgttgagatc cagttcgatg taacccactc gtgcacccaa ctgatcttca gcatctttta    7560
ctttcaccag cgtttctggg tgagcaaaaa caggaaggca aaatgccgca aaaaagggaa    7620
taagggcgac acggaaatgt tgaatactca tactcttcct ttttcaatat tattgaagca    7680
tttatcaggg ttattgtctc atgagcggat acatatttga atgtatttag aaaaataaac    7740
aaatagggt tccgcgcaca tttccccgaa aagtgccacc tgacgtctaa gaaaccatta    7800
ttatcatgac attaacctat aaaaataggc gtatcacgag gcccttcgt c             7851
```

<210> SEQ ID NO 16  
<211> LENGTH: 40  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 16
cgcaactgtc catactctga atataaaatc ccgccaatct                           40

<210> SEQ ID NO 17  
<211> LENGTH: 42  
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 17
gaacatcgtc aaaaaaccct aacatctccc tttcctattt tt                       42

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggttttttg acgatgttct tgaaactcaa tgtcttttt t                         41

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagagtatgg acagttgcgg atgtacttca gaaaagatta gatg                     44

<210> SEQ ID NO 20
<211> LENGTH: 6941
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgct tgcattaaga gaaatttaca gggtgcttca aattgacggc cggttttata   240
tcagtattga cacaaatacc ggtgaaaaag agaaaacgta tattcaactg ctgaaagacc   300
agcatttcag ggatctttct gttatcaggc gtgcttcctg tctatgtatt gtggctgtta   360
aataaaaaat ttctcgggaa atatatccaa gatcctcgta ttaggatttg ggtatatttt   420 cttaatttt tatttttgc atatacttta tattaaaaaa agtttttttc atataaactt    480
ataacagaag aaagaacaaa gaggtgatat cagacagggc agacattctt tgtgaacaaa   540
aggaatgaat attcattccg taaacgaatc ggaggttgtc agattacatg atatccgcat   600
ccagcagtaa atacgacatg attatgaaag cgtcagtctc actttttacg gaaagggggtt  660 ttgacgctac cactattcct atgatagctg aacgtgctca tgtagggaca ggaacgatct   720
atcgttattt tgacagcaaa gaaacactcg ttaacgtact gtttcaagaa agcatccagc   780
gatttacgga aaaactgaag caagacgttt cagaattgcc tgtcagagaa gctttcacc    840 acgtattttg ctgtctcgtt cagtttacga aagagagcga ctatgcgctt ttttttcttg    900
aaaccaaaaa agacgctcat tacttaaatc atacaagcaa aaaatgata gaaaatctga   960 ctcaaatgct tgatgactat tttaataagg gaaaagcgga aggcgtgatt cgcagcctgc   1020
```

```
cctctaatgt gttaattgcg attgtattag gggcgtttct caagatatat cagctcgttc    1080
aaacaggtga tatagagatg acactgatt  taattactga attggaacaa tgctgctggg    1140
acgccattaa gcttcattca tcacaaaaat aggaaaggga gatgttaggg ttttttgacg    1200
atgttcttga aactcaatgt cttttttgt  agaatcaata gaagtgtgta attgttgatg    1260
ggacaataaa aaaggagctg aaacacagta tgggaaaggt ttatgtattt gatcatcctt    1320
taattcagca caagctgaca tatatacgga atgaaaatac aggtacgaag gattttagag    1380
agttagtaga tgaagtggct acactcatgg catttgaaat tacccgcgat cttcctctgg    1440
aagaagtgga tatcaataca ccggttcagg ctgcgaaatc gaaagtcatc tcagggaaaa    1500
aactcggagt ggttcctatc ctcagagcag gattgggaat ggttgacggc attttaaagc    1560
tgattcctgc ggcaaaagtg ggacatgtcg gcctttaccg tgatccagaa accttaaaac    1620
ccgtggaata ctatgtcaag cttccttctg atgtggaaga gcgtgaattc atcgtggttg    1680
acccgatgct cgctacaggc ggttccgcag ttgaagccat tcacagcctt aaaaaacgcg    1740
gtgcgaaaaa tatccgtttc atgtgtcttg tagcagcgcc ggagggtgtg aagaattgc     1800 agaagcatca ttcggacgtt gatatttaca ttgcggcgct agatgaaaaa ttaaatgaaa    1860
aaggatatat tgttccaggt ctcggagatg cgggtgaccg catgtttgga acaaaataaa    1920
aaatgaaatc cccaaaaggg ggtttcattt ttttatccag ttttttgcta ttcggtgaat    1980
ctgtatacaa ttataggtga aaatgtgaac attctgggat ccgataaacc cagcgaacca    2040
tttgaggtga taggtaagat tataccgagg tatgaaaacg agaattggac ctttacagaa    2100
ttactctatg aagcgccata tttaaaaagc taccaagacg aagaggatga agaggatgag    2160
gaggcagatt gccttgaata tattgacaat actgataaga taatatatct tttatataga    2220
agatatcgcc gtatgtaagg atttcagggg gcaaggcata ggcagcgcgc ttatcaatat    2280
atctatagaa tgggcaaagc ataaaaaactt gcatggacta atgcttgaaa cccaggacaa    2340
taaccttata gcttgtaaat tctatcataa ttgtggtttc aaaatcggct ccgtcgatac    2400
tatgttatac gccaactttc aaaacaactt tgaaaaagct gttttctggt atttaaggtt    2460
ttagaatgca aggaacagtg aattggagtt cgtcttgtta taattagctt cttggggtat    2520
ctttaaatac tgtagaaaag aggaaggaaa taataaatgg ctaaaatgag aatatcaccg    2580
gaattgaaaa aactgatcga aaaataccgc tgcgtaaaag atacgaaagg aatgtctcct    2640
gctaaggtat ataagctggt gggagaaaat gaaaacctat atttaaaaat gacggacagc    2700
cggtataaag ggaccaccta tgatgtgaaa cgggaaaagg acatgatgct atggctggaa    2760
ggaaagctgc ctgttccaaa ggtcctgcac tttgaacggc atgatggctg agcaatctg     2820 ctcatgagtg aggccgatgg cgtcctttgc tcggaagagt atgaagatga acaaagccct    2880
gaaaagatta tcgagctgta tgcggagtgc atcaggctct ttcactccat cgacatatcg    2940
gattgtccct atacgaatag cttagacagc cgcttagccg aattggatta cttactgaat    3000
aacgatctgg ccgatgtgga ttgcgaaaac tgggaagaag acactccatt taaagatccg    3060
cgcgagctgt atgatttttt aaagacgaa  aagcccgaag aggaacttgt cttttcccac    3120
ggcgacctgg gagacagcaa catctttgtg aaagatggca agtaagtgg  ctttattgat    3180 cttgggagaa gcggcaggggc ggacaagtgg tatgacattg ccttctgcgt ccggtcgatc    3240
agggaggata tcggggaaga acagtatgtc gagctatttt ttgacttact ggggatcaag    3300
cctgattggg agaaaataaa atattatatt ttactggatg aattgtttta gtacctagat    3360
```

```
ttagatgtct aaaaagcttt aactacaagc ttttagaca tctaatctttt tctgaagtac    3420
atccgcaact gtccatactc tgaatataaa atcccgccaa tctgattggc gggattgctt    3480
tgcatatgag aaaccggca cgataatgaa atctactgaa aaggatgtta tagggagtat    3540
cgcgccggcc ttattattca tatcggcatg cagaggcaaa agtttagttc ttttttacctt   3600
gttttttaaaa ataaatagtc tgaaagtctt gttttttgatt ttcgactcag gcttttggca  3660
ttttgttctt tcttattcct taagatcagt catctgttga agattgatgc ttgaattgct    3720
gttccacatg cttacggtaa tgaaagtcat gaatcagccg aatggtcggc ctgattaaca   3780
gcagcaaact tccgatcgca aacagccata tccctgccga cattaaccgg tcataaaaaa    3840
agaaaaaact tccaacgaga aacatagcac cgatgataaa atcgtttact gtataaagaa    3900
ccttatatcg ttttttgaaa aaaagctcat atcgtttcaa ctcttttttgg atgtcatgtt   3960
cttcatttcc tttcattatc atccctccat tcaattttgg cttacccctta cgtaaacggc   4020
atgtaaacat aagggctgcc ttgctgaaag aagacataat caacgatcag aaactaaagt    4080
aaaaaagtga tctgtatagg atctcttttt tacgatttca tcgcctgaac aataagagca    4140
gtcaaagttt tgccccttt aggaaccaag tgaacaccat caggggtaaa atattccgga    4200
tgctgaagag cttctgtatg ccagtcaact aacgtaacat tttgatgtgc gtgggcctgt    4260
tgctgcaaag attcatttac cttgctttcc cattggcggg gaacccgtgt attgacaaga    4320
taaatatgag cttttgagaa agattgaagc agttgttcga tttggctgtt tgtaaaatag   4380
ccattggttc caagctcaat gatgacagcc ttgttcggct gattaaaaga cttgtattcc    4440
ctgcggtgtg aaataccgca cagatgcgta aggagaaaat accgcatcag cgcccattcg   4500
ccattcaggc tgcgcaactg ttgggaaggg cgatcggtgc gggcctcttc gctattacgc    4560
cagctggcga aggggggatg tgctgcaagg cgattaagtt gggtaacgcc agggttttcc    4620
cagtcacgac gttgtaaaac gacggccagt gaattcgagc tcggtacccg ggatcctct    4680
agagtcgacc tgcaggcatg caagcttggc gtaatcatgg tcatagctgt ttcctgtgtg   4740
aaattgttat ccgctcacaa ttccacacaa catacgagcc ggaagcataa agtgtaaagc    4800
ctggggtgcc taatgagtga gctaactcac attaattgcg ttgcgctcac tgcccgcttt    4860
ccagtcggga aacctgtcgt gccagctgca ttaatgaatc ggccaacgcg cggggagagg   4920
cggtttgcgt attgggcgct cttccgcttc ctcgctcact gactcgctgc gctcggtcgt    4980
tcggctgcgg cgagcggtat cagctcactc aaaggcggta atacggttat ccacagaatc    5040
agggggataac gcaggaaaga acatgtgagc aaaaggccag caaaaggcca ggaaccgtaa    5100
aaaggccgcg ttgctggcgt ttttccatag gctccgcccc cctgacgagc atcacaaaaa   5160
tcgacgctca gtcagaggt ggcgaaaccc gacaggacta taaagatacc aggcgtttcc    5220
ccctggaagc tccctcgtgc gctctcctgt tccgaccctg ccgcttaccg gatacctgtc    5280
cgcctttctc ccttcgggaa gcgtggcgct ttctcatagc tcacgctgta ggtatctcag    5340
ttcggtgtag tcgttcgct ccaagctggg ctgtgtgcac gaacccccccg ttcagcccga    5400
ccgctgcgcc ttatccggta actatcgtct tgagtccaac ccggtaagac acgacttatc    5460
gccactggca gcagccactg gtaacaggat tagcagagcg aggtatgtag gcggtgctac    5520
agagttcttg aagtggtggc ctaactacgg ctacactaga agaacagtat ttggtatctg    5580
cgctctgctg aagccagtta ccttcggaaa aagagttggt agctcttgat ccggcaaaca    5640
aaccaccgct ggtagcggtg gtttttttgt ttgcaagcag cagattacgc gcagaaaaaa    5700
aggatctcaa gaagatcctt tgatcttttc tacggggtct gacgctcagt ggaacgaaaa    5760
```

-continued

```
ctcacgttaa gggattttgg tcatgagatt atcaaaaagg atcttcacct agatcctttt    5820
aaattaaaaa tgaagtttta aatcaatcta aagtatatat gagtaaactt ggtctgacag    5880
ttaccaatgc ttaatcagtg aggcacctat ctcagcgatc tgtctatttc gttcatccat    5940
agttgcctga ctccccgtcg tgtagataac tacgatacgg gagggcttac catctggccc    6000
cagtgctgca atgataccgc gagacccacg ctcaccggct ccagatttat cagcaataaa    6060
ccagccagcc ggaagggccg agcgcagaag tggtcctgca actttatccg cctccatcca    6120
gtctattaat tgttgccggg aagctagagt aagtagttcg ccagttaata gtttgcgcaa    6180
cgttgttgcc attgctacag gcatcgtggt gtcacgctcg tcgtttggta tggcttcatt    6240
cagctccggt tcccaacgat caaggcgagt tacatgatcc cccatgttgt gcaaaaaagc    6300
ggttagctcc ttcggtcctc cgatcgttgt cagaagtaag ttggccgcag tgttatcact    6360
catggttatg gcagcactgc ataattctct tactgtcatg ccatccgtaa gatgcttttc    6420
tgtgactggt gagtactcaa ccaagtcatt ctgagaatag tgtatgcggc gaccgagttg    6480
ctcttgcccg gcgtcaatac gggataatac cgcgccacat agcagaactt taaaagtgct    6540
catcattgga aaacgttctt cggggcgaaa actctcaagg atcttaccgc tgttgagatc    6600
cagttcgatg taacccactc gtgcacccaa ctgatcttca gcatctttta ctttcaccag    6660
cgtttctggg tgagcaaaaa caggaaggca aaatgccgca aaaaagggaa taagggcgac    6720
acggaaatgt tgaatactca tactcttcct ttttcaatat tattgaagca tttatcaggg    6780
ttattgtctc atgagcggat acatatttga atgtatttag aaaaataaac aaatagggt     6840
tccgcgcaca tttccccgaa aagtgccacc tgacgtctaa gaaaccatta ttatcatgac    6900
attaacctat aaaaataggc gtatcacgag gccctttcgt c                         6941
```